US009388163B2

(12) United States Patent
Hecht et al.

(10) Patent No.: US 9,388,163 B2
(45) Date of Patent: Jul. 12, 2016

(54) MULTIFUNCTIONAL RADICAL QUENCHERS FOR THE TREATMENT OF MITOCHONDRIAL DYSFUNCTION

(71) Applicants: Sidney Hecht, Phoenix, AZ (US); Omar Khdour, Phoenix, AZ (US); Sandipan Roy Chowdhury, Tempe, AZ (US); Poulami Talukder, Tempe, AZ (US)

(72) Inventors: Sidney Hecht, Phoenix, AZ (US); Omar Khdour, Phoenix, AZ (US); Sandipan Roy Chowdhury, Tempe, AZ (US); Poulami Talukder, Tempe, AZ (US)

(73) Assignee: Arizona Board of Regents, a Body Corporate of the State of Arizona, Acting for and on Behalf of Arizona State University, Scottsdale, AZ (US)

(*) Notice: Subject to any disclaimer, the term of this patent is extended or adjusted under 35 U.S.C. 154(b) by 0 days.

(21) Appl. No.: 14/731,950

(22) Filed: Jun. 5, 2015

(65) Prior Publication Data
US 2015/0266851 A1 Sep. 24, 2015

Related U.S. Application Data

(63) Continuation of application No. 14/009,437, filed as application No. PCT/US2012/032108 on Apr. 4, 2012, now Pat. No. 9,102,626.

(60) Provisional application No. 61/471,346, filed on Apr. 4, 2011.

(51) Int. Cl.
*C07D 279/20* (2006.01)
*C07D 213/74* (2006.01)
*C07D 211/94* (2006.01)
*C07D 401/06* (2006.01)
*G01N 33/50* (2006.01)
*C07D 213/89* (2006.01)
*C07D 279/18* (2006.01)

(52) U.S. Cl.
CPC .......... *C07D 401/06* (2013.01); *C07D 211/94* (2013.01); *C07D 213/74* (2013.01); *C07D 213/89* (2013.01); *C07D 279/18* (2013.01); *C07D 279/20* (2013.01); *G01N 33/5079* (2013.01)

(58) Field of Classification Search
CPC .. C07D 211/94; C07D 213/74; C07D 279/20; C07D 401/06
USPC ........................................ 544/37; 514/226.2
See application file for complete search history.

(56) References Cited

FOREIGN PATENT DOCUMENTS

| JP | 2001209176 | 8/2001 |
| WO | 9631217 | 10/1996 |
| WO | 0200683 | 1/2002 |
| WO | 2005/034855 A2 | 4/2005 |
| WO | WO 2009142760 A1 * | 11/2009 |
| WO | 2011103536 | 8/2011 |

OTHER PUBLICATIONS

Alexadre, Bypasses of the Antomycin A block of mitochondrial electron transport in relation to ubisemiquinone function, Biochimica et Biophysica Acta, Apr. 1984, vol. 767, pp. 120-129, Elsevier.
Bencze, Human frataxin: iron and ferrochelatase binding surface, Chem Commun, May 2007, vol. 18, pp. 1798-1800.
Bindokas, Superoxide production in rat hippocampal neurons: selective imaging with hydroethidine, The Journal of Neuroscience, Feb. 1996, vol. 16, No. 4, pp. 1324-1336.
Bradley, Clinical, biochemical and molecular genetic correlations in Friedreich's ataxia, Human Molecular Genetics, 2000, vol. 9, No. 2, pp. 275-282, Oxford University Press.
Bulteau, Frataxin acts as an iron chaperone protein to modulate mitochondrial aconitase activity, Science, 2004, vol. 305, pp. 242-245.
Campuzano, Friedreich's ataxia: autosomal recessive disease caused by an intronic GAA triplet repeat expansion, Science, Mar. 1996, vol. 271, No. 5254.
Campuzano, Frataxin is reduced in Friedreich ataxia patients and is associated with mitochondrial membranes, Human Molecular Genetics, 1997, vol. 6, No. 11, pp. 1771-1780. Oxford University Press.
Dimauro, Mitochondrial DNA mutations in human disease, American Journal of Medical Genetics, 2001, vol. 106, pp. 18-26.
Drummen, C11-BODIPY, an oxidation-sensitive fluorescent lipid peroxidation probe: (micro)spectroscopic characterization and validation of methodology, Free Radical Biology and Medicine, 2002, vol. 33, No. 4, pp. 473-490, Elsevier.

(Continued)

*Primary Examiner* — Kahsay Habte
(74) *Attorney, Agent, or Firm* — McDonnell Boehnen Hulbert & Berghoff LLP

(57) ABSTRACT

The present disclosure provides methods for identifying therapeutic agents that are multifunctional radical quenchers. It also provides compounds of formula:

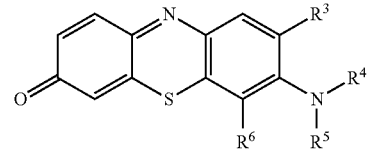

and pharmaceutically acceptable salts thereof, compositions comprising these compounds, and methods of using these compounds in a variety of applications, such as treatment or suppression of diseases associated with decreased mitochondrial function resulting in diminished ATP production and/or oxidative stress and/or lipid peroxidation.

19 Claims, 3 Drawing Sheets

(56) References Cited

OTHER PUBLICATIONS

Gonzalez-Cabo, Frataxin interacts functionally with mitochondrial electron transport chain proteins, Human Molecular Genetics, 2005, vol. 14, No. 15, pp. 2091-2098, Oxford University Press.

Griffith, Potent and specific inhibition of glutathione synthesis by buthionine sulfoximine (S-n-Butyl homocysteine sulfoximine), The Journal of Biological Chemistry, Aug. 1979, vol. 254, No. 16, pp. 7558-7560.

Hwan, Tiron, a ROS scavenger, protects human lung cancer Calu-6 cells against antimycin A-induced cell death, Oncology Reports, 2009, vol. 21, pp. 253-261.

James, Interactions of mitochondria-targeted and untargeted ubiquinones with the mitochondrial respiratory chain and reactive oxygen species, The Journal of Biological Chemistry, Jun. 2005, vol. 280, No. 22, pp. 21295-21312, JBC Papers.

Jauslin, A cellular model for Friedreich Ataxia reveals small-molecule glutathione peroxidase memetics as novel treatment strategy, Human Molecular Genetics, 2002, vol. 11, No. 24, pp. 3055-3063, Oxford University Press.

Katafias, Oxidation of phenothiazine dyes by manganese(III) in sulfuric acid solution, Transition Met Chem, 2011, vol. 36, pp. 801-809, Springer.

Kuypers, Parinaric acid as a sensitive fluorescent probe for the determination of lipid peroxidation, Biochimica et Biophysica Acta, Feb. 1987, vol. 921, pp. 266-274, Elsevier.

Lebel, Evaluation of the probe 2',7'-Dichlorofluorescin as an indicator of reactive oxygen species formation and oxidative stress, Chem Res Toxicol, 1992, vol. 5, pp. 227-231, American Chemistry Society.

Leonard, Mitochondrial respiratory chain disorders I: mitochondrial DNA defects, Lancet, 2000, vol. 355, pp. 299-304.

Matsuno, Studies of the mechanism of oxidative phosphorylation, The Journal of Biological Chemistry, Nov. 1985, vol. 260, No. 27, pp. 14424-14427, The American Society of Biological Chemists, Inc.

Pap, Ratio-fluorescence microscopy of lipid oxidation in living cells using C11-BODIPY, FEBS Letters, 1999, vol. 453, pp. 278-282, Federation of European Biochemical Societies.

Park, Yeast frataxin sequentially chaperones and stores iron by coupling protein assembly with iron oxidation, The Journal of Biological Chemistry, Aug. 2003, vol. 278, No. 33, pp. 31340-31351, The American Society for Biochemistry and Molecular Biology, Inc.

Quinzii, Respiratory chain dysfunction and oxidative stress correlate with severity of primary CoQ10 deficiency, FASEB, Jun. 2008, vol. 22, No. 6, pp. 1874-1885, FASEB.

Robinson, Nonviability of cells with oxidative defects in galactose medium: a screening test for affected patient fibroblasts, Biochemical Medicine and Metabolic Biology, 1992, vol. 48, pp. 122-126, Academic Press, Inc.

Vinod, Os(VIII) as an efficient homogeneous catalyst for the oxidative decolorization of methylene blue dye with alkaline chloramine-T: kinetic, mechanistic, and platinum metal ions reactivity studies, Ind Eng Chem Res, 2010, vol. 49, pp. 3137-3145, American Chemical Society.

Wilson, Respiratory deficiency due to loss of mitochondrial DNA in yeast lacking the frataxin homologue, Nature Genetics, Aug. 1997, vol. 16, pp. 352-357, Nature Publishing Group.

Wilson, Frataxin and frataxin deficiency in Friedreich's ataxia, Journal of the Neurological Sciences, 2003, vol. 207, pp. 103-105, Elsevier Science B.V.

Yamada, Immunochemical detection of a lipofuscin-like fluorophore derived from malondialdehyde and lysine, Journal of Lipid Research, 2001, vol. 42, pp. 1187-1196.

Yin, Biochemical basis of lipofuscin, ceroid, and age pigment-like fluorophores, Free Radical Biology & Medicine, 1996, vol. 21, No. 6, pp. 871-888, Elsevier Science Inc.

Yoon, Iron-sulfur cluster biosynthesis. characterization of frataxin as an iron donor for assembly of [2Fe-2S] clusters in ISU-type proteins, J Am Chem Soc, 2003, vol. 125, pp. 6078-6084, American Chemical Society.

Yoon, Frataxin-mediated iron delivery to ferrochelatase in the final step of heme biosynthesis, The Journal of Biological Chemistry, Jun. 2004, vol. 279, No. 25, pp. 25943-25946, The American Society for Biochemistry and Molecular Biology, Inc.

Wu, Autoxidation of phosphatidylcholine liposomes, Lipids, 1982, vol. 17, No. 6, pp. 403-413.

Lamarche, The cardiomyopathy of Friedreich's ataxia morphological observations in 3 cases, The Canadian Journal of Neurological Science, Nov. 1980, vol. 7, No. 4, pp. 389-396.

International Preliminary Report on Patentability for PCT/US2012/032108, mailed Oct. 17, 2013.

Robushi L., Sperimentale (1940), vol. 94, pp. 99-124.

* cited by examiner

MULTIFUNCTIONAL RADICAL QUENCHERS FOR THE TREATMENT OF MITOCHONDRIAL DYSFUNCTION

CROSS REFERENCE

This application is a continuation of U.S. patent application Ser. No. 14/009,437 filed Oct. 16, 2013, which is a national stage filing of PCT/US2012/032108 filed Apr. 4, 2012, which claims priority to 61/471,346 filed Apr. 4, 2011, all of which are incorporated by reference herein in its entirety.

FIELD OF THE INVENTION

The present disclosure provides methods for identifying therapeutic agents that are multifunctional radical quenchers. It also provides biologically active compounds multifunctional radical quenchers and pharmaceutically acceptable salts thereof, compositions comprising these compounds, and methods of using these compounds in a variety of applications, such as treatment or suppression of diseases associated with decreased mitochondrial function resulting in diminished ATP production and/or oxidative stress and/or lipid peroxidation.

SUMMARY OF THE INVENTION

Mitochondria are intracellular organelles responsible for a number of metabolic transformations and regulatory functions. They produce much of the ATP employed by eukaryotic cells. They are also the major source of free radicals and reactive oxygen species that cause oxidative stress. Consequently, mitochondrial defects are damaging, particularly to neural and muscle tissues which have high energy level demands. Thus, energetic defects have been implicated in forms of movement disorders, cardiomyopathy, myopathy, blindness, and deafness (DiMauro et al. (2001) Am. J. Med. Genet. 106, 18-26; Leonard et al. (2000) Lancet. 355, 299-304). There are a number of mitochondrial diseases resulting from both nuclear and mitochondrial genetic defects, and the underlying biochemistries of these diseases tend to be rather similar. They include increased lactate production, diminished respiration and ATP production, and reflect the consequences of oxidative stress. This invention describes novel compounds for the treatment or suppression of diseases associated with decreased mitochondrial function resulting in diminished ATP production and/or oxidative stress and/or lipid peroxidation. The invention also describes use of these compounds for the treatment of mitochondrial disorders, including but not limited to Friedreich's ataxia, Leber's Hereditary Optic Neuropathy, Kearns-Sayre Syndrome, Mitochondrial Encephalomyopathy with Lactic Acidosis and Stroke-Like Episodes and more generally, any disease associated with impairment of energy production and mitochondrial function. Aging may also involve decreased mitochondrial function and diminished ATP production, and the therapeutic agents described here may also find utility in mitigating the effects of aging.

Thus, in one aspect, the disclosure provides a method for identifying a therapeutic agent, comprising assaying a test compound for the ability to:
a) quench mitochondrially generated reactive oxygen species (ROS);
b) quench lipid radicals produced by mitochondrially generated ROS;
c) augment ATP production, and
d) afford cytoprotection to cells under oxidative stress, wherein such a test compound is a candidate therapeutic agent for treating or protecting mitochondria with respiratory chain lesions.

Another aspect of the disclosure provides compounds of formula (I)

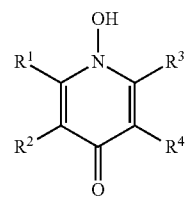

and pharmaceutically acceptable salts thereof.

Another aspect of the disclosure provides compounds of formula (II)

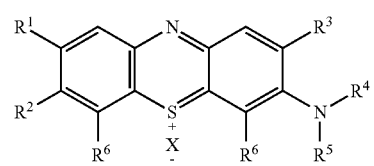

and pharmaceutically acceptable salts thereof.

Another aspect of the disclosure provides compounds of formula (II-A)

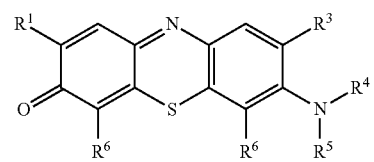

and pharmaceutically acceptable salts thereof.

Another aspect of the disclosure provides pharmaceutical compositions comprising the compounds and salts of the disclosure and an appropriate carrier, excipient or diluent. The exact nature of the carrier, excipient or diluent will depend upon the desired use for the composition, and may range from being suitable for veterinary uses to being suitable for human use. The compositions may optionally include one or more additional compounds suitable for a use.

Another aspect of the disclosure provides methods of treating or suppressing diseases associated with decreased mitochondrial function resulting in diminished ATP production and/or oxidative stress and/or lipid peroxidation, comprising administering an effective amount of the compound and salts of the disclosure.

Another aspect of the disclosure provides a method of treating or suppressing one or more of Friedreich's ataxia, Leber's Hereditary Optic Neuropathy, Kearns-Sayre Syndrome, Mitochondrial Encephalomyopathy with Lactic Acidosis and Stroke-Like Episodes, or Leigh syndrome, comprising administering an effective amount of the compound and salts of the disclosure.

Another aspect of the disclosure provides a method of treating or suppressing one or more of obesity, atherosclerosis, amyotrophic lateral sclerosis, Parkinson's Disease, cancer, heart failure, myocardial infarction (MI), Alzheimer's Disease, Huntington's Disease, schizophrenia, bipolar disorder, fragile X syndrome, chronic fatigue syndrome, and Leigh syndrome, comprising administering an effective amount of the compound and salts of the disclosure.

DESCRIPTION OF DRAWINGS

The results set forth herein, and the properties and characteristics of the compounds provided by the disclosure, can be advantageously understood with regard to the drawings.

DETAILED DESCRIPTION OF THE INVENTION

Figure 1:
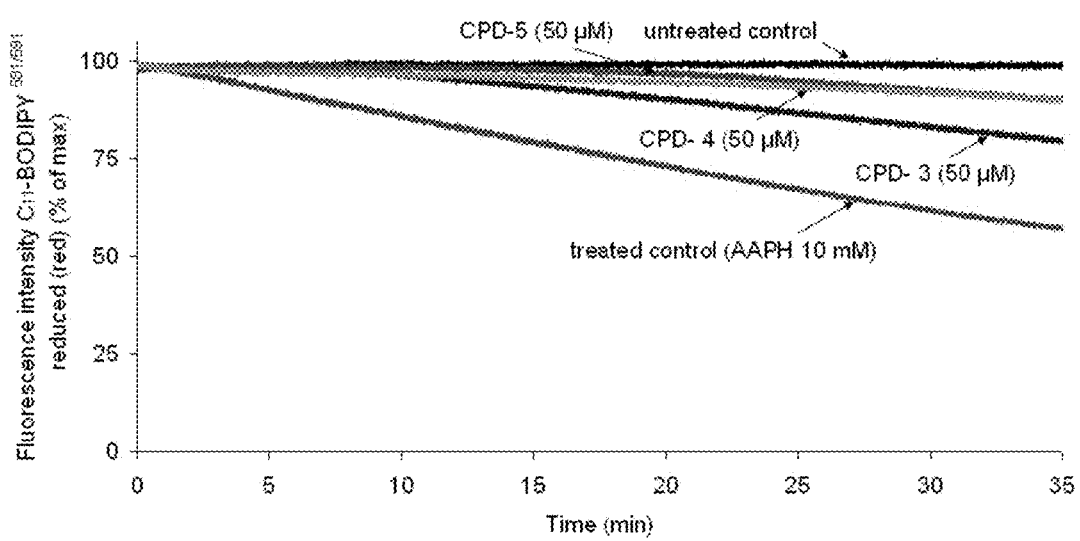
FIG. 1 shows effect of the compounds of the disclosure on lipid peroxidation induced by oxygen radicals generated from thermal decomposition of 2,2'-azobis(2-amidinopropane)dihydrochloride (AAPH) (10 mM) in phospholipids liposomes in Tris-HCl buffer containing $C_{11}$-BODIPY$^{581/591}$ (200 nM) at 40° C. The red fluorescence decay of the probe was monitored with time ($\lambda_{ex}$=570, $\lambda_{em}$=600 nm). Relative fluorescence units are normalized to 100% intensity. Identical results were obtained in replicate experiments.

In one aspect, the disclosure provides a method for identifying a therapeutic agent, comprising assaying a test compound for the ability to:
a) quench mitochondrially generated reactive oxygen species (ROS);
b) quench lipid radicals produced by mitochondrially generated ROS;
c) augment ATP production, and
d) afford cytoprotection to cells under oxidative stress,
wherein such a test compound is a candidate therapeutic agent for treating or protecting mitochondria with respiratory chain lesions.

In one embodiment, the disclosure provides the method wherein assaying the ability of the test compound to quench mitochondrially generated ROS comprises: a) pretreating test cells with the test compound; b) treating the test cells with an agent that depletes cellular glutathione; c) treating the test cells with a fluorescent stain; and d) measuring fluorescence from the test cells, wherein a decrease in fluorescence from the test cells compared to a control indicates that the test compound quenches ROS. In one embodiment, the disclosure provides the method wherein the agent that depletes cellular glutathione is diethyl maleate, (R,S)-3-Hydroxy-4-pentenoate, or N-ethylmaleimide. In another embodiment, the agent is diethyl maleate. In another embodiment, the disclosure provides the method wherein flow cytometry is used to measure fluorescence.

In one embodiment, the disclosure provides the method comprising identifying a test compound that reduces ROS production by at least 50% compared to control.

In one embodiment, the disclosure provides the method comprising identifying a test compound that reduces ROS production catalytically. Catalytic reduction of ROS production is determined by demonstrating that the quantitative reduction in ROS exceeds the amount of test compound employed.

In one embodiment, the disclosure provides the method wherein the ROS comprises superoxide, peroxide, hydroxyl radical, singlet oxygen or nitrogen oxides. In one embodiment, ROS is superoxide.

In one embodiment, the disclosure provides the method wherein quenching lipid radicals produced by mitochondrially generated ROS comprises measuring lipid peroxidation in a model membrane system. In one embodiment, the model membrane system comprises phosphotidylcholine liposomes, submitochondrial particles (SMP), mitochondrial membrane fractions. In one embodiment, the model membrane system comprises phosphotidylcholine liposomes.

In one embodiment, the disclosure provides the method wherein assaying the ability of the test compound to quench lipid radicals produced by mitochondrially generated ROS comprises: a) pretreating unilamellar phospholipid vesicles containing the embedded fluorophore with the test compound; b) treating the phospholipid vesicles with a free radical generator; and c) measuring fluorescence, wherein maintenance of fluorescence from the phospholipid vesicles compared to a control indicates that the test compound quenches lipid radicals produced by mitochondrially generated ROS. In one embodiment, the embedded fluorophore is $C_{11}$—BODIPY$^{581/591}$. In one embodiment, the free radical generator comprises 2,2'-azo-bis(2-amidinopropane), 2,2'-azobis(2-amidinopropane)dihydrochloride (AAPH), or 2,2'-azobis(2,4-dimethyl-valeronitrile) (AMVN). In one embodiment, the free radical generator is a combination of ferrous sulfate, ascorbic acid and hydrogen peroxide. In one embodiment, the free radical generator is 2,2'-azo-bis(2-amidinopropane). In one embodiment, measuring fluorescence is performed over a period of at least 20 minutes.

In one embodiment, the method comprises identifying a test compound that reduces lipid peroxidation in a model by at least 50% compared to a control.

In one embodiment, the method comprises identifying a test compound that reduces lipid peroxidation in a model system by donation of a hydrogen atom or its functional equivalent. This can be determined by also testing a closely related analog of the test compound, which is incapable of donating a hydrogen atom. The test compound, after donation of the hydrogen atom or its functional equivalent, is resonance stabilized. This can be determined by also testing a closely related analog of the test compound, which is incapable of comparable resonance stabilization.

In one embodiment, the method comprises identifying a test compound that reduces lipid peroxidation in a model system and participates in electron transfer reactions within the mitochondrial respiratory chain. This can be determined by testing electron donation to complex III, cytochrome c, or complex IV, or by demonstrating enhanced ATP production.

In one embodiment, the disclosure provides the method wherein assaying the ability of the test compound to augment ATP production comprises: a) treating coenzyme $Q_{10}$ ($CoQ_{10}$) deficient test cells with the test compound; b) incubating the test cells with the test compound; and c) measuring ATP levels in the test cells after incubation, wherein an increase in ATP levels for the test cells compared to a control indicates that the test compound augments ATP production.

In one embodiment, the method wherein assaying the ability of the test compound to augment ATP production comprises starving $CoQ_{10}$ deficient test cells for glucose prior to treatment with the test compound to limit non-mitochondrial ATP production.

In one embodiment, the method assaying the ability of the test compound to augment ATP production comprises wherein incubation of the test cells is over at least 48 hours.

In one embodiment, measuring ATP levels comprises treatment with reagents to support the luciferin-luciferase reaction, which produces luminescence.

In one embodiment, the disclosure provides the method comprising identifying a test compound that augments ATP production by at least 5% compared to control. In one embodiment, ATP production is augmented at least 10% compared to control.

In one embodiment, the method assaying the ability of the test compound to augment ATP production comprises identifying a test compound that augments ATP production by using electrons that have escaped from a mitochondrial electron transport chain. This can be determined by demonstrating that ROS decreases as ATP increases.

In one embodiment, the disclosure provides the method wherein assaying the test compound for the ability to protect the test cells from oxidative stress. In one embodiment, the test cells are Friedreich's ataxia fibroblasts. In another embodiment, the test cells are Friedreich's ataxia lymphocytes or CEM leukemia cells. In yet another embodiment, the test cells are from a broad range of inherited mitochondrial diseases, including Friedreich's ataxia, Leber's Hereditary Optic Neuropathy, Kearns-Sayre Syndrome, Mitochondrial Encephalomyopathy with Lactic Acidosis and Stroke-Like Episodes, or Leigh syndrome. In another embodiment, the test cells are from diseases that have a significant mitochondrial component or diseases in which the tissues are known to be under stress, including, but not limited to obesity, atherosclerosis, Parkinson's Disease, cancer, heart failure, myocardial infarction (MI), Alzheimer's Disease, Huntington's Disease, schizophrenia, bipolar disorder, fragile X syndrome, and chronic fatigue syndrome.

In one embodiment, the disclosure provides the method wherein assaying the ability to protect the test cells from oxidative stress comprises: a) pretreating the test cells with the test compound; b) treating the test cells with an inhibitor of glutathione biosynthesis, or a compound that otherwise reduces the availability of reduced glutathione; c) incubating the test cells; and d) measuring cell viability of the test cells, wherein an increase in number of viable test cells compared to a control indicates that the test compound protects the cells from oxidative stress. In one embodiment, the inhibitor of glutathione biosynthesis is L-buthionine (S,R)-sulfoximine. In another embodiment, the inhibitor of glutathione biosynthesis is N,N,N',N'-tetramethyldiazene-1,2-dicarboxamide. In one embodiment, measuring mitochondrial membrane potential is used to assess the viability of the test cells.

In one embodiment, the disclosure provides the method wherein the test compound is a candidate therapeutic agent for treating or protecting mitochondria with respiratory chain lesions in concentration of less than 10 μM. In another embodiment, the concentration is less than 1 μM.

Another aspect of the disclosure provides compounds of formula (I)

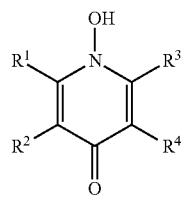

(I)

or a pharmaceutically acceptable salt thereof, wherein
$R^1$ is $C_1$-$C_6$ alkyl, $C_2$-$C_6$ alkenyl, $C_2$-$C_6$ alkynyl, —$OR^5$, —$SR^5$, —$NHR^5$, or —$N(R^5)_2$, each optionally substituted with one to four substituents selected from halogen, —CN, —$NO_2$, —$N_3$, $C_1$-$C_6$ alkyl, halo($C_1$-$C_6$ alkyl), —$OR^6$, —$NR^6_2$, —$CO_2R^6$, and —$CONR^6_2$;
where each $R^5$ independently is hydrogen, $C_1$-$C_6$ alkyl, or halo($C_1$-$C_6$ alkyl);
where each $R^6$ independently is hydrogen or $C_1$-$C_6$ alkyl;
$R^2$ is hydrogen, halogen, $C_1$-$C_6$ alkyl, $C_2$-$C_6$ alkenyl, $C_2$-$C_6$ alkynyl, —$OR^5$, —$SR^5$, —$NHR^5$, or —$N(R^5)_2$, each optionally substituted with one to four substituents selected from halogen, —CN, —$NO_2$, —$N_3$, $C_1$-$C_6$ alkyl, halo($C_1$-$C_6$ alkyl), —$OR^6$, —$NR^6_2$, —$CO_2R^6$, and —$CONR^6_2$;
$R^3$ is $C_1$-$C_{20}$ alkyl, $C_2$-$C_{20}$ alkenyl, $C_2$-$C_{20}$ alkynyl, —$OR^5$, —$SR^5$, —$NHR^5$, —$N(R^5)_2$, each optionally substituted with one to four substituents selected from halogen, —CN, —$NO_2$, —$N_3$, $C_1$-$C_6$ alkyl, halo($C_1$-$C_6$ alkyl), —$OR^7$, —$NR^7_2$, —$CO_2R^7$, —$OC(O)R^7$, —$CON(R^7)_2$, —$OC(O)N(R^7)_2$, —$NHC(O)N(R^7)_2$, —$NHC(NH)N(R^7)_2$, $C_3$-$C_8$ cycloalkyl, $C_3$-$C_8$ cycloalkenyl, aryl, heteroaryl, and heterocycle, wherein each cycloalkyl, cycloalkenyl, aryl, heteroaryl, and heterocycle are optionally substituted with $R^8$;
where each $R^7$ independently is hydrogen, $C_1$-$C_6$ alkyl, halo($C_1$-$C_6$ alkyl), $C_3$-$C_8$ cycloalkyl, aryl, heteroaryl, heterocycle, aryl($C_1$-$C_6$ alkyl), $C_3$-$C_8$ cycloalkyl($C_1$-$C_6$ alkyl), aryl($C_1$-$C_6$ alkyl), heteroaryl($C_1$-$C_6$ alkyl), or heterocycle($C_1$-$C_6$ alkyl), wherein each cycloalkyl, aryl, heteroaryl, and heterocycle are optionally substituted with $R^8$;
where each $R^8$ independently is halogen, —CN, —$NO_2$, —$N_3$, $C_1$-$C_6$ alkyl, halo($C_1$-$C_6$ alkyl), $C_1$-$C_6$ alkoxy, amino, $C_1$-$C_6$alkylamino, or di$C_1$-$C_6$alkylamino; and
$R^4$ is $C_1$-$C_{20}$ alkyl, $C_2$-$C_{20}$ alkenyl, $C_2$-$C_{20}$ alkynyl, —$OR^5$, —$SR^5$, —$NHR^5$, —$N(R^5)_2$, each optionally substituted with one to four substituents selected from halogen, —CN, —$NO_2$, —$N_3$, $C_1$-$C_6$ alkyl, halo($C_1$-$C_6$ alkyl), —$OR^7$, —$NR^7_2$, —$CO_2R^7$, —$OC(O)R^7$, —$CON(R^7)_2$, —$OC(O)N(R^7)_2$, —$NHC(O)N(R^7)_2$, —$NHC(NH)N(R^7)_2$, $C_3$-$C_8$ cycloalkyl, $C_3$-$C_8$ cycloalkenyl, aryl, heteroaryl, and heterocycle, wherein each cycloalkyl, cycloalkenyl, aryl, heteroaryl, and heterocycle are optionally substituted with $R^8$;
provided at least one of $R^3$ or $R^4$ is optionally substituted $C_4$-$C_{20}$ alkyl, optionally substituted $C_4$-$C_{20}$ alkenyl, or optionally substituted $C_4$-$C_{20}$ alkynyl.

In one embodiment, the disclosure provides compounds of formula (I), wherein
$R^1$ is $C_1$-$C_6$ alkyl, $C_2$-$C_6$ alkenyl, $C_2$-$C_6$ alkynyl, —$OR^5$, —$SR^5$, —$NHR^5$, or —$N(R^5)_2$, each optionally substituted with one to four substituents selected from halogen, —CN, —$NO_2$, —$N_3$, $C_1$-$C_6$ alkyl, halo($C_1$-$C_6$ alkyl), —$OR^6$, —$NR^6_2$, —$CO_2R^6$, and —$CONR^6_2$;
where each $R^5$ independently is hydrogen, $C_1$-$C_6$ alkyl, or halo($C_1$-$C_6$ alkyl);
where each $R^6$ independently is hydrogen or $C_1$-$C_6$ alkyl;
$R^2$ is $C_1$-$C_6$ alkyl, $C_2$-$C_6$ alkenyl, $C_2$-$C_6$ alkynyl, —$OR^5$, —$SR^5$, —$NHR^5$, or —$N(R^5)_2$, each optionally substituted with one to four substituents selected from halogen, —CN, —$NO_2$, —$N_3$, $C_1$-$C_6$ alkyl, halo($C_1$-$C_6$ alkyl), —$OR^6$, —$NR^6_2$, —$CO_2R^6$, and —$CONR^6_2$;
$R^3$ is $C_1$-$C_{20}$ alkyl, $C_2$-$C_{20}$ alkenyl, $C_2$-$C_{20}$ alkynyl, —$OR^5$, —$SR^5$, —$NHR^5$, —$N(R^5)_2$, each optionally substituted with one to four substituents selected from halogen, —CN, —$NO_2$, —$N_3$, $C_1$-$C_6$ alkyl, halo($C_1$-$C_6$ alkyl), —$OR^7$, —$NR^7_2$, —$CO_2R^7$, —$OC(O)R^7$, —$CON(R^7)_2$, —$OC(O)N(R^7)_2$, —$NHC(O)N(R^7)_2$, —$NHC(NH)N(R^7)_2$, $C_3$-$C_8$ cycloalkyl, $C_3$-$C_8$ cycloalkenyl, aryl, heteroaryl, and heterocycle, wherein each cycloalkyl, cycloalkenyl, aryl, heteroaryl, and heterocycle are optionally substituted with $R^8$;

where each $R^7$ independently is hydrogen, $C_1$-$C_6$ alkyl, halo($C_1$-$C_6$ alkyl), $C_3$-$C_8$ cycloalkyl, aryl, heteroaryl, heterocycle, aryl($C_1$-$C_6$ alkyl), $C_3$-$C_8$ cycloalkyl($C_1$-$C_6$ alkyl), aryl($C_1$-$C_6$ alkyl), heteroaryl($C_1$-$C_6$ alkyl), or heterocycle($C_1$-$C_6$ alkyl), wherein each cycloalkyl, aryl, heteroaryl, and heterocycle are optionally substituted with $R^8$;

where each $R^8$ independently is halogen, —CN, —NO$_2$, —N$_3$, $C_1$-$C_6$ alkyl, halo($C_1$-$C_6$ alkyl), $C_1$-$C_6$ alkoxy, amino, $C_1$-$C_6$alkylamino, or di$C_1$-$C_6$alkylamino; and $R^4$ is $C_1$-$C_{20}$ alkyl, $C_2$-$C_{20}$ alkenyl, $C_2$-$C_{20}$ alkynyl, —OR$^5$, —SR$^5$, —NHR$^5$, —N(R$^5$)$_2$, each optionally substituted with one to four substituents selected from halogen, —CN, —NO$_2$, —N$_3$, $C_1$-$C_6$ alkyl, halo($C_1$-$C_6$ alkyl), —OR$^7$, —NR$^7{}_2$, —CO$_2$R$^7$, —OC(O)R$^7$, —CON(R$^7$)$_2$, —OC(O)N(R$^7$)$_2$, —NHC(O)N(R$^7$)$_2$, —NHC(NH)N(R$^7$)$_2$, $C_3$-$C_8$ cycloalkyl, $C_3$-$C_8$ cycloalkenyl, aryl, heteroaryl, and heterocycle, wherein each cycloalkyl, cycloalkenyl, aryl, heteroaryl, and heterocycle are optionally substituted with $R^8$; provided at least one of $R^3$ or $R^4$ is optionally substituted $C_4$-$C_{20}$ alkyl, optionally substituted $C_4$-$C_{20}$ alkenyl, or optionally substituted $C_4$-$C_{20}$ alkynyl.

In one embodiment, the disclosure provides compounds of formula (I), wherein $R^1$ is $C_1$-$C_6$ alkyl. In another embodiment, $R^1$ is methyl.

In another embodiment, the disclosure provides compounds of formula (I), wherein $R^1$ is —OR$^5$, —SR$^5$, —NHR$^5$, or —N(R$^5$)$_2$.

In one embodiment, the disclosure provides compounds as described above with any reference to formula (I), wherein $R^2$ is $C_1$-$C_6$ alkyl or $C_1$-$C_6$ alkenyl. In another embodiment, the disclosure provides compounds as described above with any reference to formula (I), wherein $R^2$ is $C_1$-$C_6$ alkyl. In yet another embodiment, $R^2$ is methyl.

In one embodiment, the disclosure provides compounds as described above with any reference to formula (I), wherein $R^2$ is $C_1$-$C_6$ alkenyl. In another embodiment, $R^2$ is vinyl or allyl. In yet another embodiment, $R^2$ is vinyl.

In another embodiment, the disclosure provides compounds as described above with any reference to formula (I), wherein $R^2$ is —OR$^5$, —SR$^5$, —NHR$^5$, or —N(R$^5$)$_2$.

In yet another embodiment, the disclosure provides compounds as described above with any reference to formula (I), wherein $R^2$ is —OR$^5$. In one embodiment, $R^2$ is —OR$^5$ and $R^5$ is hydrogen or $C_1$-$C_6$ alkyl. In another embodiment, $R^2$ is —OH. In yet another embodiment, $R^2$ is —O($C_1$-$C_6$ alkyl). In yet another embodiment, $R^2$ is —OCH$_3$.

In one embodiment, the disclosure provides compounds as described above with any reference to formula (I), wherein $R^2$ is —NHR$^5$, or —N(R$^5$)$_2$. In one embodiment, $R^2$ is —NHR$^5$ and $R^5$ is hydrogen or $C_1$-$C_6$ alkyl. In another embodiment, $R^2$ is —NH$_2$. In yet another embodiment, $R^2$ is —NH($C_1$-$C_6$ alkyl). In yet another embodiment, $R^2$ is —NHCH$_3$. In another embodiment, $R^2$ is —N($C_1$-$C_6$ alkyl)$_2$. In yet another embodiment, $R^2$ is —N(CH$_3$)$_2$.

In one embodiment, the disclosure provides compounds as described above with any reference to formula (I), wherein $R^2$ is hydrogen or halogen.

In another embodiment, the disclosure provides compounds as described above with any reference to formula (I), wherein $R^2$ is hydrogen.

In yet another embodiment, the disclosure provides compounds as described above with any reference to formula (I), wherein $R^2$ is halogen. In one embodiment, $R^2$ is Br. In one embodiment, $R^2$ is Cl.

In one embodiment, the disclosure provides compounds of formula (I), wherein both $R^1$ and $R^2$ are $C_1$-$C_6$ alkyl. In another embodiment, both $R^1$ and $R^2$ are methyl.

In another embodiment, the disclosure provides compounds of formula (I), wherein $R^1$ is $C_1$-$C_6$ alkyl and $R^2$ is $C_1$-$C_6$ alkenyl. In another embodiment, $R^1$ is methyl and $R^2$ is vinyl.

In another embodiment, the disclosure provides compounds of formula (I), wherein $R^1$ is $C_1$-$C_6$ alkyl and $R^2$ is —NHR$^5$. In another embodiment, $R^1$ is methyl and $R^2$ is —NH$_2$.

In another embodiment, the disclosure provides compounds of formula (I), wherein $R^1$ is $C_1$-$C_6$ alkyl and $R^2$ is —OR$^5$. In another embodiment, $R^1$ is methyl and $R^2$ is —OCH$_3$.

In another embodiment, the disclosure provides compounds of formula (I), wherein $R^1$ is $C_1$-$C_6$ alkyl and $R^2$ is hydrogen. In another embodiment, $R^1$ is methyl and $R^2$ is hydrogen.

In another embodiment, the disclosure provides compounds of formula (I), wherein $R^1$ is $C_1$-$C_6$ alkyl and $R^2$ is halogen. In another embodiment, $R^1$ is methyl and $R^2$ is Br or Cl.

In one embodiment, the disclosure provides compounds as described above with any reference to formula (I), wherein $R^3$ is optionally substituted $C_1$-$C_3$ alkyl, optionally substituted $C_1$-$C_3$ alkenyl, or optionally substituted $C_1$-$C_3$ alkynyl. In one embodiment, $R^3$ is optionally substituted $C_1$-$C_3$ alkyl. In another embodiment, $R^3$ is methyl.

In one embodiment, the disclosure provides compounds as described above with any reference to formula (I), wherein $R^3$ is —OR$^5$, —SR$^5$, —NHR$^5$, or —N(R$^5$)$_2$.

In one embodiment, the disclosure provides compounds as described above with any reference to formula (I), wherein $R^4$ is optionally substituted $C_4$-$C_{20}$ alkyl, optionally substituted $C_4$-$C_{20}$ alkenyl, or optionally substituted $C_4$-$C_{20}$ alkynyl. In another embodiment, $R^4$ is optionally substituted $C_5$-$C_{20}$ alkyl.

In one embodiment, the disclosure provides compounds as described above with any reference to formula (I), wherein $R^4$ is optionally substituted $C_1$-$C_3$ alkyl, optionally substituted $C_1$-$C_3$ alkenyl, or optionally substituted $C_1$-$C_3$ alkynyl. In one embodiment, $R^4$ is optionally substituted $C_1$-$C_3$ alkyl. In another embodiment, $R^4$ is methyl.

In one embodiment, the disclosure provides compounds as described above with any reference to formula (I), wherein $R^4$ is —OR$^5$, —SR$^5$, —NHR$^5$, or —N(R$^5$)$_2$. In this embodiment, $R^3$ is optionally substituted $C_4$-$C_{20}$ alkyl, optionally substituted $C_4$-$C_{20}$ alkenyl, or optionally substituted $C_4$-$C_{20}$ alkynyl. In another embodiment, $R^4$ is optionally substituted $C_5$-$C_{20}$ alkyl.

Another aspect of the disclosure provides compounds of formula (II)

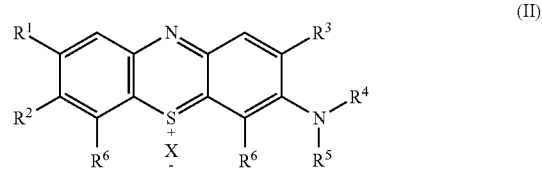

wherein

X is halogen;

$R^1$ is hydrogen, $C_1$-$C_{20}$ alkyl, $C_2$-$C_{20}$ alkenyl, $C_2$-$C_{20}$ alkynyl, —OR$^7$, —SR$^7$, —NHR$^7$, or —N(R$^7$)$_2$, each optionally substituted with one to four substituents selected from halogen, —CN, —NO$_2$, $C_1$-$C_6$ alkyl, halo($C_1$-$C_6$ alkyl), —$OR^8$, —$NR^8_2$, —$CO_2R^8$, —$CONR^8_2$, $C_3$-$C_8$ cycloalkyl, $C_3$-$C_8$ cycloalkenyl, aryl, heteroaryl, and heterocycle, wherein each cycloalkyl, cycloalkenyl, aryl, heteroaryl, and heterocycle are optionally substituted with $R^9$;
where each $R^7$ independently is hydrogen, $C_1$-$C_6$ alkyl, or halo($C_1$-$C_6$ alkyl);
where each $R^8$ independently is hydrogen, $C_1$-$C_6$ alkyl, halo($C_1$-$C_6$ alkyl), $C_3$-$C_8$ cycloalkyl, aryl, heteroaryl, heterocycle, aryl($C_1$-$C_6$ alkyl), $C_3$-$C_8$ cycloalkyl($C_1$-$C_6$ alkyl), aryl($C_1$-$C_6$ alkyl), heteroaryl($C_1$-$C_6$ alkyl), or heterocycle($C_1$-$C_6$ alkyl), wherein each cycloalkyl, aryl, heteroaryl, and heterocycle are optionally substituted with $R^9$;
where each $R^9$ independently is halogen, —CN, —$NO_2$, —$N_3$, $C_1$-$C_6$ alkyl, halo($C_1$-$C_6$ alkyl), $C_1$-$C_6$ alkoxy, amino, $C_1$-$C_6$alkylamino, or di$C_1$-$C_6$alkylamino;
$R^2$ is —$OR^{11}$, —$SR^{11}$, —$NHR^{11}$, or —$N(R^{11})_2$;
where each $R^{11}$ independently is hydrogen, $C_1$-$C_{20}$ alkyl, $C_2$-$C_{20}$ alkenyl, $C_2$-$C_{20}$ alkynyl, or halo($C_1$-$C_{20}$ alkyl);
$R^3$ is hydrogen, $C_1$-$C_{20}$ alkyl, $C_2$-$C_{20}$ alkenyl, $C_2$-$C_{20}$ alkynyl, or —$OR^7$, each optionally substituted with one to four substituents selected from halogen, —CN, —$NO_2$, $C_1$-$C_6$ alkyl, halo($C_1$-$C_6$ alkyl), —$OR^8$, —$NR^8_2$, —$CO_2R^8$, —$CONR^8_2$, $C_3$-$C_8$ cycloalkyl, $C_3$-$C_8$ cycloalkenyl, aryl, heteroaryl, and heterocycle, wherein each cycloalkyl, cycloalkenyl, aryl, heteroaryl, and heterocycle are optionally substituted with $R^9$;
$R^4$ and $R^5$ are independently $C_1$-$C_{20}$ alkyl, $C_2$-$C_{20}$ alkenyl, or $C_2$-$C_{20}$ alkynyl, each optionally substituted with one to four substituents selected from halogen, —CN, —$NO_2$, $C_1$-$C_6$ alkyl, halo($C_1$-$C_6$ alkyl), —$OR^8$, —$NR^8_2$, —$CO_2R^8$, —$CONR^8_2$, $C_3$-$C_8$ cycloalkyl, $C_3$-$C_8$ cycloalkenyl, aryl, heteroaryl, and heterocycle, wherein each cycloalkyl, cycloalkenyl, aryl, heteroaryl, and heterocycle are optionally substituted with $R^9$;
each $R^6$ is hydrogen, $C_1$-$C_{20}$ alkyl, $C_2$-$C_{20}$ alkenyl, $C_2$-$C_{20}$ alkynyl, $C_3$-$C_8$ cycloalkyl, $C_3$-$C_8$ cycloalkenyl, aryl, heteroaryl, heterocycle, or —$OR^{10}$, wherein each alkyl, alkenyl, and alkynyl are optionally substituted with one to four substituents selected from halogen, —CN, —$NO_2$, $C_1$-$C_6$ alkyl, halo($C_1$-$C_6$ alkyl), —$OR^8$, —$NR^8_2$, —$CO_2R^8$, —$CONR^8_2$, $C_3$-$C_8$ cycloalkyl optionally substituted with $R^9$, $C_3$-$C_8$ cycloalkenyl optionally substituted with $R^9$, aryl optionally substituted with $R^9$, heteroaryl optionally substituted with $R^9$, and heterocycle optionally substituted with $R^9$;
where $R^{10}$ is $C_1$-$C_6$ alkyl, halo($C_1$-$C_6$ alkyl), $C_3$-$C_8$ cycloalkyl, aryl, heteroaryl, heterocycle, aryl($C_1$-$C_6$ alkyl), $C_3$-$C_8$cycloalkyl($C_1$-$C_6$ alkyl), aryl($C_1$-$C_6$ alkyl), heteroaryl($C_1$-$C_6$ alkyl), or heterocycle($C_1$-$C_6$ alkyl), wherein each cycloalkyl, aryl, heteroaryl, and heterocycle are optionally substituted with $R^9$.

In one embodiment, the disclosure provides compounds of formula (II), wherein X is Br or Cl.

In one embodiment, the disclosure provides compounds as described above with reference to formula (II), wherein $R^1$ is hydrogen, optionally substituted $C_1$-$C_{20}$ alkyl, optionally substituted $C_2$-$C_{20}$ alkenyl, optionally substituted $C_2$-$C_{20}$ alkynyl, or —$OR^7$. In one embodiment, $R^1$ is hydrogen.

In one embodiment, the disclosure provides compounds as described above with any reference to formula (II), wherein $R^1$ is optionally substituted $C_1$-$C_{20}$ alkyl. In one embodiment, $C_1$-$C_{20}$ alkyl is optionally substituted with —$OR^8$, $C_3$-$C_8$ cycloalkyl, $C_3$-$C_8$ cycloalkenyl, or aryl, wherein each cycloalkyl, cycloalkenyl, and aryl are optionally substituted with $R^9$. In another embodiment, $R^1$ is $C_1$-$C_{20}$ alkyl optionally substituted with $C_3$-$C_8$ cycloalkyl, $C_3$-$C_8$ cycloalkenyl, or aryl, wherein each cycloalkyl, cycloalkenyl, and aryl are optionally substituted with $R^9$.

In one embodiment, the disclosure provides compounds as described above with any reference to formula (II), wherein $R^1$ is —$OR^7$ and $R^7$ is $C_1$-$C_6$ alkyl.

In one embodiment, the disclosure provides compounds as described above with any reference to formula (II), wherein $R^2$ is —$OR^{11}$. In another embodiment, $R^2$ is —$OR^{11}$, and $R^{11}$ is hydrogen, $C_1$-$C_6$ alkyl, or halo($C_1$-$C_6$ alkyl).

In one embodiment, the disclosure provides compounds as described above with any reference to formula (II), wherein $R^2$ is —OH.

In one embodiment, the disclosure provides compounds as described above with any reference to formula (II), wherein $R^2$ is —$NHR^{11}$, or —$N(R^{11})_2$. In another embodiment, $R^2$ is —$NHR^{11}$ or —$N(R^{11})_2$, and $R^{11}$ is hydrogen, $C_4$-$C_{20}$ alkyl, $C_4$-$C_{20}$ alkenyl, or $C_4$-$C_{20}$ alkynyl.

In another embodiment, the disclosure provides compounds as described above with any reference to formula (II), wherein $R^2$ is —$N(R^{11})_2$. In yet another embodiment, $R^2$ is —$N(R^{11})_2$, and $R^{11}$ is hydrogen, $C_4$-$C_{20}$ alkyl, $C_4$-$C_{20}$ alkenyl, or $C_4$-$C_{20}$ alkynyl. In a further embodiment, $R^2$ is —$N(R^{11})_2$, and $R^{11}$ is hydrogen or $C_4$-$C_{20}$ alkyl. Even further, $R^2$ is —$N(C_4$-$C_{20}$ alkyl$)_2$.

In another embodiment, the disclosure provides compounds as described above with any reference to formula (II), wherein $R^2$ is —$N(decyl)_2$.

In another embodiment, the disclosure provides compounds as described above with any reference to formula (II), wherein $R^2$ is —$N(pentyl)_2$.

In one embodiment, the disclosure provides compounds as described above with any reference to formula (II), wherein $R^3$ is hydrogen, optionally substituted $C_1$-$C_{20}$ alkyl, or —$OR^7$. In one embodiment, $R^3$ is hydrogen. In another embodiment $R^3$ is optionally substituted $C_1$-$C_{20}$ alkyl. In yet another embodiment, $C_1$-$C_{20}$ alkyl is optionally substituted with —$OR^8$, $C_3$-$C_8$ cycloalkyl, $C_3$-$C_8$ cycloalkenyl, or aryl, wherein each cycloalkyl, cycloalkenyl, and aryl are optionally substituted with $R^9$.

In one embodiment, the disclosure provides compounds as described above with any reference to formula (II), wherein $R^3$ is $C_1$-$C_{20}$ alkyl optionally substituted with $C_3$-$C_5$ cycloalkyl, $C_3$-$C_8$ cycloalkenyl, or aryl, wherein each cycloalkyl, cycloalkenyl, and aryl are optionally substituted with $R^9$.

In one embodiment, the disclosure provides compounds as described above with any reference to formula (II), wherein $R^3$ is —$OR^7$ and $R^7$ is $C_1$-$C_6$ alkyl.

In one embodiment, the disclosure provides compounds as described above with any reference to formula (II), wherein $R^4$ is optionally substituted $C_1$-$C_{20}$ alkyl. In one embodiment, $R^4$ is $C_1$-$C_{20}$ alkyl.

In one embodiment, the disclosure provides compounds as described above with any reference to formula (II), wherein $R^5$ is optionally substituted $C_1$-$C_{20}$ alkyl. In one embodiment, $R^5$ is $C_1$-$C_{20}$ alkyl.

In one embodiment, the disclosure provides compounds as described above with any reference to formula (II), wherein $R^6$ is hydrogen or optionally substituted $C_1$-$C_{20}$ alkyl. In one embodiment, $R^6$ is hydrogen. In another embodiment, $R^6$ is $C_1$-$C_{20}$ alkyl optionally substituted with —$OR^8$, $C_3$-$C_8$ cycloalkyl, $C_3$-$C_8$ cycloalkenyl, or aryl, wherein each cycloalkyl, cycloalkenyl, and aryl are optionally substituted with $R^9$. In yet another embodiment, $C_1$-$C_{20}$ alkyl is optionally substituted with $C_3$-$C_8$ cycloalkyl, $C_3$-$C_8$ cycloalkenyl, or aryl, wherein each cycloalkyl, cycloalkenyl, and aryl are optionally substituted with $R^9$.

In one embodiment, the disclosure provides compounds as described above with reference to formula (II), wherein $R^6$ is —$OR^{10}$, where $R^{10}$ is $C_1$-$C_6$ alkyl, $C_3$-$C_8$ cycloalkyl, aryl, heteroaryl, heterocycle, aryl($C_1$-$C_6$ alkyl), $C_3$-$C_8$ cycloalkyl ($C_1$-$C_6$ alkyl), aryl($C_1$-$C_6$ alkyl), heteroaryl($C_1$-$C_6$ alkyl), or heterocycle($C_1$-$C_6$ alkyl), wherein each cycloalkyl, aryl, heteroaryl, and heterocycle are optionally substituted with $R^9$. In another embodiment, $R^6$ is —$OR^{10}$, where $R^{10}$ is aryl or aryl($C_1$-$C_6$ alkyl), where each aryl is optionally substituted with $R^9$.

In one embodiment, the disclosure provides compounds as described above with reference to formula (II), wherein X is another anion other than halogen. Suitable anions include, but are not limited to, carbonate, hydrogen carbonate, hydroxide, nitrate, nitrite, cyanide, phosphate, sulfate, sulfite, acetate, formate, propionate, isopropionate, malonate, maleate, lacate, succiniate, tartrate, citrate and oxalate.

In one embodiment, the disclosure provides compounds of formula (II) wherein $R^2$ is —OH, and $R^3$-$R^6$ are as described above with any reference to formula (II). In another embodiment, these compounds can tautomerize as follows:

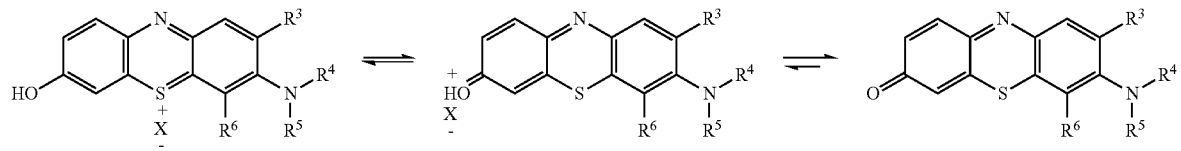

Therefore, another aspect of the disclosure provides compounds of formula (II-A)

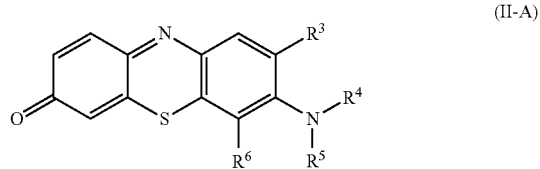

wherein $R^3$ is hydrogen, $C_1$-$C_{20}$ alkyl, $C_2$-$C_{20}$ alkenyl, $C_2$-$C_{20}$ alkynyl, or —$OR^7$, each optionally substituted with one to four substituents selected from halogen, —CN, —$NO_2$, $C_1$-$C_6$ alkyl, halo($C_1$-$C_6$ alkyl), —$OR^8$, —$NR^8{}_2$, —$CO_2R^8$, —$CONR^8{}_2$, $C_3$-$C_8$ cycloalkyl, $C_3$-$C_8$ cycloalkenyl, aryl, heteroaryl, and heterocycle, wherein each cycloalkyl, cycloalkenyl, aryl, heteroaryl, and heterocycle are optionally substituted with $R^9$;

where each $R^7$ independently is hydrogen, $C_1$-$C_6$ alkyl, or halo($C_1$-$C_6$ alkyl);

where each $R^8$ independently is hydrogen, $C_1$-$C_6$ alkyl, halo($C_1$-$C_6$ alkyl), $C_3$-$C_8$ cycloalkyl, aryl, heteroaryl, heterocycle, aryl($C_1$-$C_6$ alkyl), $C_3$-$C_8$ cycloalkyl($C_1$-$C_6$ alkyl), aryl($C_1$-$C_6$ alkyl), heteroaryl($C_1$-$C_6$ alkyl), or heterocycle($C_1$-$C_6$ alkyl), wherein each cycloalkyl, aryl, heteroaryl, and heterocycle are optionally substituted with $R^9$;

where each $R^9$ independently is halogen, —CN, —$NO_2$, —$N_3$, $C_1$-$C_6$ alkyl, halo($C_1$-$C_6$ alkyl), $C_1$-$C_6$ alkoxy, amino, $C_1$-$C_6$alkylamino, or di$C_1$-$C_6$alkylamino;

$R^4$ and $R^5$ are independently $C_1$-$C_{20}$ alkyl, $C_2$-$C_{20}$ alkenyl, or $C_2$-$C_{20}$ alkynyl, each optionally substituted with one to four substituents selected from halogen, —CN, —$NO_2$, $C_1$-$C_6$ alkyl, halo($C_1$-$C_6$ alkyl), —$OR^8$, —$NR^8{}_2$, —$CO_2R^8$, —$CONR^8{}_2$, $C_3$-$C_8$ cycloalkyl, $C_3$-$C_8$ cycloalkenyl, aryl, heteroaryl, and heterocycle, wherein each cycloalkyl, cycloalkenyl, aryl, heteroaryl, and heterocycle are optionally substituted with $R^9$;

each $R^6$ is hydrogen, $C_1$-$C_{20}$ alkyl, $C_2$-$C_{20}$ alkenyl, $C_2$-$C_{20}$ alkynyl, $C_3$-$C_8$ cycloalkyl, $C_3$-$C_8$ cycloalkenyl, aryl, heteroaryl, or heterocycle, wherein each alkyl, alkenyl, and alkynyl are optionally substituted with one to four substituents selected from halogen, —CN, —$NO_2$, $C_1$-$C_6$ alkyl, halo($C_1$-$C_6$ alkyl), —$OR^8$, —$NR^8{}_2$, —$CO_2R^8$, —$CONR^8{}_2$, $C_3$-$C_8$ cycloalkyl optionally substituted with $R^9$, $C_3$-$C_8$ cycloalkenyl optionally substituted with $R^9$, aryl optionally substituted with $R^9$, heteroaryl optionally substituted with $R^9$, and heterocycle optionally substituted with $R^9$.

In one embodiment, the disclosure provides compounds of formula (II-A), wherein $R^3$ is hydrogen, optionally substituted $C_1$-$C_{20}$ alkyl, or —$OR^7$. In one embodiment, $R^3$ is hydrogen. In another embodiment $R^3$ is optionally substituted $C_1$-$C_{20}$ alkyl. In yet another embodiment, $C_1$-$C_{20}$ alkyl is optionally substituted with —$OR^8$, $C_3$-$C_8$ cycloalkyl, $C_3$-$C_8$ cycloalkenyl, or aryl, wherein each cycloalkyl, cycloalkenyl, and aryl are optionally substituted with $R^9$.

In one embodiment, the disclosure provides compounds of formula (II-A), wherein $R^3$ is $C_1$-$C_{20}$ alkyl optionally substituted with $C_3$-$C_8$ cycloalkyl, $C_3$-$C_8$ cycloalkenyl, or aryl, wherein each cycloalkyl, cycloalkenyl, and aryl are optionally substituted with $R^9$.

In one embodiment, the disclosure provides compounds of formula (II-A), wherein $R^3$ is —$OR^7$ and $R^7$ is $C_1$-$C_6$ alkyl.

In one embodiment, the disclosure provides compounds as described above with any reference to formula (II-A), wherein $R^4$ is optionally substituted $C_1$-$C_{20}$ alkyl. In one embodiment, $R^4$ is $C_1$-$C_{20}$ alkyl.

In one embodiment, the disclosure provides compounds as described above with any reference to formula (II-A), wherein $R^5$ is optionally substituted $C_1$-$C_{20}$ alkyl. In one embodiment, $R^5$ is $C_1$-$C_{20}$ alkyl.

In one embodiment, the disclosure provides compounds as described above with any reference to formula (II-A), wherein $R^6$ is hydrogen or optionally substituted $C_1$-$C_{20}$ alkyl. In one embodiment, $R^6$ is hydrogen. In another embodiment, $R^6$ is $C_1$-$C_{20}$ alkyl optionally substituted with —$OR^8$, $C_3$-$C_8$ cycloalkyl, $C_3$-$C_8$ cycloalkenyl, or aryl, wherein each cycloalkyl, cycloalkenyl, and aryl are optionally substituted with $R^9$. In yet another embodiment, $C_1$-$C_{20}$ alkyl is optionally substituted with $C_3$-$C_8$ cycloalkyl, $C_3$-$C_8$ cycloalkenyl, or aryl, wherein each cycloalkyl, cycloalkenyl, and aryl are optionally substituted with $R^9$.

In one embodiment, the disclosure provides compounds as described above with reference to formula (I) or (II), which can exist as prodrugs. For example, —OH group in formula (I) and —$R^2$ in formula (II) can exist as prodrug. Suitable prodrugs include alkyl and aryl esters, acetates, carbamates, amino acid esters, such as glycine and alanine, and the like.

In another embodiment, the disclosure provides pharmaceutically acceptable salts of compounds of the disclosure. Generally, pharmaceutically acceptable salts are those salts that retain substantially one or more of the desired pharmacological activities of the parent compound and which are suitable for administration to humans. Pharmaceutically acceptable salts include acid addition salts formed with inorganic acids or organic acids. Inorganic acids suitable for forming pharmaceutically acceptable acid addition salts include, by way of example and not limitation, hydrohalide acids (e.g., hydrochloric acid, hydrobromic acid, hydriodic, etc.), sulfuric acid, nitric acid, phosphoric acid, and the like. Organic acids suitable for forming pharmaceutically acceptable acid addition salts include, by way of example and not limitation, acetic acid, monofluoroacetic acid, difluoroacetic acid, trifluoroacetic acid, propionic acid, hexanoic acid, cyclopentanepropionic acid, glycolic acid, oxalic acid, pyruvic acid, lactic acid, malonic acid, succinic acid, malic acid, maleic acid, fumaric acid, tartaric acid, citric acid, palmitic acid, benzoic acid, 3-(4-hydroxybenzoyl)benzoic acid, cinnamic acid, mandelic acid, alkylsulfonic acids (e.g., methanesulfonic acid, ethanesulfonic acid, 1,2-ethane-disulfonic acid, 2-hydroxyethanesulfonic acid, etc.), arylsulfonic acids (e.g., benzenesulfonic acid, 4-chlorobenzenesulfonic acid, 2-naphthalenesulfonic acid, 4-toluenesulfonic acid, camphorsulfonic acid, etc.), 4-methylbicyclo[2.2.2]-oct-2-ene-1-carboxylic acid, glucoheptonic acid, 3-phenylpropionic acid, trimethylacetic acid, tertiary butylacetic acid, lauryl sulfuric acid, gluconic acid, glutamic acid, hydroxynaphthoic acid, salicylic acid, stearic acid, muconic acid, and the like. For example, in one embodiment, the salt is a trifluoroacetic acid salt, p-toluenesulfonic acid salt, or hydrochloride salt.

Pharmaceutically acceptable salts also include salts formed when an acidic proton present in the parent compound is either replaced by an inorganic ion (e.g., an alkali metal ion such as $Na^+$, $K^+$ or $Li^+$, an alkaline earth ion such as $Ca^{2+}$ or $Mg^{2+}$, an aluminum ion, or an ammonium ion) or coordinates with an organic base (e.g., ethanolamine, diethanolamine, triethanolamine, N-methylglucamine, morpholine, piperidine, dimethylamine, diethylamine, etc.).

The compounds described herein, as well as the salts thereof, may also be in the form of hydrates, solvates and N-oxides, as are well-known in the art.

Therapeutic Applications

In one aspect, the disclosure provides a method for treating or protecting mitochondria with respiratory chain lesions, comprising administering to a subject in need of such treatment an effective amount of one or more compounds of the invention.

Compounds of the disclosure are useful, for example, for treating or suppressing diseases associated with decreased mitochondrial function resulting in diminished ATP production and/or oxidative stress and/or lipid peroxidation in a subject in need of treatment. The present disclosure provides methods of treating conditions including but not limited to Friedreich's ataxia, Leber's Hereditary Optic Neuropathy, Kearns-Sayre Syndrome, Mitochondrial Encephalomyopathy with Lactic Acidosis and Stroke-Like Episodes, and Leigh syndrome in a subject by administering an effective amount of a compound as described above with respect to any of formulae (I), (II), or (II-A), including a salt or solvate or stereoisomer thereof.

The disclosure also provides methods of treating conditions including but not limited to obesity, atherosclerosis, amyotrophic lateral sclerosis, Parkinson's Disease, cancer, heart failure, myocardial infarction (MI), Alzheimer's Disease, Huntington's Disease, schizophrenia, bipolar disorder, fragile X syndrome, chronic fatigue syndrome, and Leigh syndrome, in a subject by administering an effective amount of a compound as described above with respect to any of formulae (I), (II), or (II-A), including a salt or solvate or stereoisomer thereof.

In addition, the compounds of the invention can be used for prophylaxis of redox stress and enhancement of cellular function.

Friedreich's Ataxia

Friedreich's ataxia is a severe neurodegenerative and cardiodegenerative condition. It is characterized by progressive ataxia of the limbs, muscle weakness, dysarthria, skeletal deformities and cardiomyopathy. While the biochemical basis of the disease is still under investigation, it is strongly associated with insufficient frataxin (Wilson et al. (1997) *Nat. Genet.* 16, 352-357; Wilson et al. (2003) *J. Neurol. Sci.* 207, 103-105). In the majority of patients the insufficiency of frataxin is a consequence of an intronic GAA triplet repeat expansion in the gene for frataxin, which results in a significant decrease in its mRNA levels, and ultimately in protein levels as well (Campuzano et al. (1996) *Science* 271, 1423-1427; Campuzano et al. (1997) *Hum. Mol. Genet.* 6, 1771-1780). Frataxin acts as an iron chaperone during heme biosynthesis (Bencze et al. (2007) *J.C.S. Chem. Commun.* 1798-1800) and has been shown to be capable of stimulating the in vitro assembly of heme and Fe—S clusters (Park et al. (2003) *J. Biol. Chem.* 278, 31340-31351; Yoon et al. (2003) *J. Am Chem. Soc.* 125, 6078-6084; Yoon et al. (2004) *J. Biol. Chem.* 279, 25943-25946). Frataxin can interact physically with mitochondrial electron transport chain proteins, as well as with mitochondrial aconitase (which contains an Fe—S cluster) (Bulteau et al. (2004) *Science* 305, 242-245; Gonzalez-Cabo et al. (2005) *Hum. Mol. Genet.* 14, 2091-2098). Therefore, frataxin deficiency results in disruption of cellular iron homeostasis, with a progressive iron accumulation in the mitochondrion, and a deficiency in heme and Fe—S clusters.

It is believed that a deficiency in frataxin leads to compromised mitochondrial respiratory chain function through a failure to assemble one or more Fe-utilizing proteins; one or more Fe—S clusters in the mitochondrial respiratory complexes are likely to represent a critical locus. In fact, diminished function of these complexes has been noted in Friedreich's ataxia patients (Bradley et al. (2000) *Hum. Mol. Genet.* 9, 275-282). The loss of mitochondrial respiratory chain function can lead to diminished ATP production, while the accumulation of Fe in the mitochondria makes the organelle highly susceptible to oxidative damage by reactive oxygen species, whose concentration increases concomitant with the decrease in respiratory chain function. There is compelling evidence that while oxidative damage is not the primary lesion in Friedreich's ataxia, oxidative stress helps to drive disease progression. Therefore, strategies to overcome oxidative stress should blunt disease progression and provide effective therapy.

Other Exemplary Mitochondrial Diseases

Leber hereditary optic neuropathy is associated with degeneration of retinal ganglion cells and causes progressive loss of vision resulting in various degrees of blindness. Leber hereditary optic neuropathy primarily affects men over the age of 20 and is maternally transmitted due to mutations in the mitochondrial (not nuclear) genome.

Kearns-Sayre syndrome is a rare neuromuscular disorder typically with onset usually before the age of 20. It is characterized by progressive external ophthalmoplegia (paralysis of the eye muscles) and mild skeletal muscle weakness, hearing loss, loss of coordination, heart problems, and cognitive delays. There are many other names for the Kearns-Sayre syndrome including: Chronic progressive external ophthalmoplegia CPEO with myopathy; CPEO with ragged-red fibers; KSS; Mitochondrial cytopathy, Kearns-Sayre type; Oculocraniosomatic syndrome; Ophthalmoplegia-plus syndrome; Ophthalmoplegia with myopathy; and Ophthalmoplegia with ragged-red fibers.

Mitochondrial Encephalomyopathy with Lactic Acidosis and Stroke-Like Episodes is a progressive mitochondrial disease that involves multiple organ systems including the central nervous system, cardiac muscle, skeletal muscle, and gastrointestinal system. Symptoms include muscle weakness, stroke-like events, eye muscle paralysis, and cognitive impairment. Leigh syndrome is a degenerative brain disorder is usually diagnosed at a young age (e.g. before age two). Deterioration is often rapid with symptoms such as seizures, dementia, feeding and speech difficulties, respiratory dysfunction, heart problems, and muscle weakness. Prognosis is poor with death typically occurring within a few years of diagnosis.

Mitochondrial Energy Production

Energy released from the citric acid (Krebs) cycle in the mitochondrial matrix enters the mitochondrial electron transport chain as NADH (complex I) and $FADH_2$ (complex II). These are the first two of five protein complexes involved in ATP production, all of which are located in the inner mitochondrial membrane. Electrons derived from NADH (by oxidation with a NADH-specific dehydrogenase) and $FADH_2$ (by oxidation with succinate dehydrogenase) travel down the respiratory chain, releasing their energy in discrete steps by driving the active transport of protons from the mitochondrial matrix to the intermembrane space (i.e., through the inner mitochondrial membrane). The electron carriers in the respiratory chain include flavins, protein-bound iron-sulfur centers, quinones, cytochromes and copper. There are two molecules that transfer electrons between complexes: coenzyme Q (complex I→III, and complex II→III) and cytochrome c (complex III→IV). The final electron acceptor in the respiratory chain is $O_2$, which is converted to $H_2O$ in complex IV.

In a functional mitochondrion, transport of two electrons through complex I results in the transport of $4H^+$ into the intermembrane space. Two more $H^+$ transfers to the intermembrane space result from electron transport through complex III, and four more $H^+$ transfers from electron transport through complex IV. The 10 electrons transported to the intermembrane space create a proton electrochemical gradient; they can return to the mitochondrial matrix via complex V (ATP synthase), with the concomitant conversion of ADP to ATP. It is interesting that no $H^+$ is transferred to the intermembrane space as a consequence of electron transport through complex II. Therefore, $2e^-$ transfer from $FADH_2$ (complex II→complex III→complex IV) results in the transport of only 6 protons, compared with 10 protons resulting from $2e^-$ transfer from NADH (complex I→complex III→complex IV), with correspondingly less ATP produced. Each glucose molecule metabolized by glycolysis produces 12 electrons; these are converted to 5 NADH molecules and 1 $FADH_2$ via the Krebs cycle in the mitochondrial matrix. The 5 NADH molecules employed in mitochondrial electron transport produce about 25 ATPs, while the single $FADH_2$ affords only about 3 ATP molecules. (There are another 4 molecules of ATP derived from glucose metabolism—2 during glycolysis and 2 in the Krebs cycle). While this analysis underscores the importance of complex I involvement in normal ATP production, it also tends to obscure certain metabolic realities/uncertainties that may offer important opportunities for therapeutic intervention. One metabolic reality is that complex I, while important quantitatively for ATP production in normal mitochondria, is not essential for all mitochondrial ATP production. Electrons can enter the electron transport chain at the level of coenzyme Q (either from complex II or from fatty acid oxidation), producing about 60% as much ATP as would have resulted had they entered the electron transport chain at complex I). While the flux of electrons that normally enter the individual mitochondrial complexes, ultimately passing through coenzyme Q, is probably dictated largely by the availability of electrons derived from NADH, $FADH_2$ and fatty acid oxidation, the actual intrinsic capacity of the individual pathways does not appear to have been studied carefully.

In functional mitochondria, a few experimental parameters can be measured readily, reflecting mitochondrial respiration. These include NADH and $O_2$ consumption, and ATP production. Less readily measured are the electrons that flow through the electron transport chain, thereby consuming oxygen, and producing $H_2O$ and ATP. The electrons within the mitochondria can really only be measured when they are associated with one of the mitochondrial electron carriers such as coenzyme Q. In humans, this mitochondrial coenzyme is present as coenzyme $Q_{10}$, which has a 50-carbon C-substituent that renders the molecule virtually insoluble in water (calculated octanol-water partition coefficient $>10^{20}$) (James et al. (2005) *J Biol. Chem.* 280, 21295-21312).

In dysfunctional mitochondria, one can still carry out the same types of measurements as noted above for functioning mitochondria. If the flow of electrons through complex I is interrupted, several measured parameters should change. These include diminished consumption of NADH (measured as increased lactate through pyruvate reduction) and diminished ATP production. Since electrons will not flow as efficiently from complex I to coenzyme Q, the concentration of this reduced coenzyme will diminish. Interestingly, a new pathway for oxygen consumption is created. While oxygen is not converted as efficiently to water in complex IV (an overall four electron reduction of each oxygen molecule), much of the flow of electrons into a defective complex I is redirected to oxygen, with the production of superoxide (a one electron reduction of each oxygen). Thus, the stoichiometry of oxygen utilization is altered. The production of superoxide by mitochondria actually occurs to some extent even in normal mitochondria, but is a much more frequent event in mitochondria containing defects in the respiratory chain. Superoxide is one form of reactive oxygen species (ROS). Superoxide itself is not believed to react readily with biological molecules such as lipid membranes, proteins and DNA, and actually functions as a signaling molecule for the regulation of certain cellular processes. Biologically, the main fate of superoxide ($O^-{}_2$) is a disproportionation reaction with itself to produce peroxide ($H_2O_2$) and oxygen, i.e.

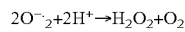

$$2O^-{}_2 + 2H^+ \rightarrow H_2O_2 + O_2$$

This reaction occurs spontaneously, and can also be catalyzed by superoxide dismutase. Superoxide can also be reduced to peroxide in a monovalent process. Like superoxide, hydrogen peroxide is also not intrinsically deleterious to cellular macromolecules, and is actually essential to the function of a number of enzymes. However, in the presence of metal ions such as iron and copper, hydrogen peroxide is converted to hydroxyl radical (HO.) and hydroxide ion ($OH^-$) according to the Fenton reaction, i.e.

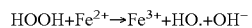

$$HOOH + Fe^{2+} \rightarrow Fe^{3+} + HO. + OH^-$$

Hydroxyl radicals are very highly reactive, capable of reacting with virtually any biological molecule, including DNA, proteins and lipids. Hydroxyl radicals can also diffuse through cells readily, and their ability to damage cells is limited only by the distance that they travel before they react. Hydroxyl radicals can also react with superoxide, producing singlet oxygen (($^1O_2$)+OH$^-$), another highly reactive form of ROS that damages cellular macromolecules and assemblies. One particularly deleterious and well-studied reaction mediated by hydroxyl radicals is the abstraction of hydrogen atoms (H.) from membrane lipids, forming a carbon-centered radical (R.). This radical HO.+RH(lipid)→R.+H$_2$O

R.+O$_2$→ROO.

ROO.+RH→ROOH+R.

can readily react with oxygen, forming a hydroperoxy radical (ROO.). The hydroperoxy radical is also highly reactive, and can abstract another hydrogen atom from the membrane lipid, producing another carbon-centered radical (which can undergo precisely the same chemistry), ultimately producing a chain reaction affording many oxidative lesions in the membrane lipids from a single hydroxyl radical (lipid peroxidation). It is for this reason that lipid peroxidation likely represents a major process by which cellular and mitochondrial membranes are degraded in cells containing (partially) dysfunctional mitochondria. The observed accumulation of lipofuscin in Friedreich's ataxia patients is fully consistent with the thesis that lipid peroxidation is a central process that drives disease progression (La Marche et al. (1980) *Can. J. Neurosci.* 7, 389-396; Yin, D. (1996) *Free Rad. Biol. Med.* 21, 871-888; Yamada et al. (2001) *J. Lipid Res.* 42, 1187-1196).

It may be noted that while all lesions in the mitochondrial electron transport chain that affect mitochondrial dysfunction will result in elevated levels of superoxide, some types of lesions may be expected to produce more functional damage. The latter would certainly include Friedreich's ataxia, in which suboptimal levels of the protein frataxin (which is responsible for cellular iron homeostasis; Park et al. (2003) *J. Biol. Chem.* 278, 31340-31351; Yoon et al. (2003) *J. Am. Chem. Soc.* 125, 6078-6084; Yoon et al. (2004) *J. Biol. Chem.* 279, 25943-25946; Bencze et al. (2007) *J.C.S. Chem. Commun.* 1798-1800) and assembly of FeS clusters in proteins results in an accumulation of Fe$^{2+/3+}$ within the mitochondria, and contributes instead to the Fenton chemistry noted above. Likewise, disorders such as amyotrophic lateral sclerosis are associated with a deficiency in the detoxifying enzyme superoxide dismutase, and will have greatly enhanced concentrations of the ROS discussed above.

One poorly studied parameter of mitochondrial electron transport is whether the process is best characterized as involving one or two electron transfers. The is important because NADH is an obligatory two-electron donor, and coenzyme Q and cytochrome c participate in two-electron redox cycles, as does FADH$_2$. Virtually all publications represent the processes in which these species participate as involving a net two electron change. However, FADH$_2$ may (and generally does) transfer its reducing equivalents as single electrons. Further, the Q cycle in complex III clearly involves single-electron transfers. Reduced cytochrome c is known to transfer electrons one at a time to cytochrome c oxidase, the enzyme responsible for the final step in respiration. Finally, the accumulation of electrons within dysfunctional mitochondria (producing reductive stress) is relieved substantially by (one-electron) reduction of oxygen to superoxide (vide supra). Thus, while the electron transport chain has the capacity to transfer two electrons by virtue of the redox cycles of most of its participants, it is not clear that it necessarily must do so to function.

Given that the reductive stress (build-up of electrons) encountered initially in mitochondrial dysfunction is a one electron process, as is lipid peroxidation, carriers of single electrons could find utility in dealing with reductive stress, e.g. molecules in which the one-electron reduced intermediate is stabilized by dipole interactions, substituent effects, resonance effects or captodative effects. Molecules designed to traffic single electrons, and which can (i) accept electrons from superoxide (ii) donate electrons to complex III and (iii) quench carbon-centered lipid radicals are especially useful. Multifunctional Radical Quenchers (MRQs) of the invention can effectively protect mitochondria, cells and organisms from oxidative stress.

Pharmaceutical Compositions

In another aspect, the present disclosure provides compositions comprising one or more of compounds as described above with respect to any of formulae (I), (II), or (II-A) and an appropriate carrier, excipient or diluent. The exact nature of the carrier, excipient or diluent will depend upon the desired use for the composition, and may range from being suitable or acceptable for veterinary uses to being suitable or acceptable for human use. The composition may optionally include one or more additional compounds.

When used to treat or prevent such diseases, the compounds described herein may be administered singly, as mixtures of one or more compounds or in mixture or combination with other agents useful for treating such diseases and/or the symptoms associated with such diseases. The compounds may also be administered in mixture or in combination with agents useful to treat other disorders or maladies, such as steroids, membrane stabilizers, 5LO inhibitors, leukotriene synthesis and receptor inhibitors, inhibitors of IgE isotype switching or IgE synthesis, IgG isotype switching or IgG synthesis, β-agonists, tryptase inhibitors, aspirin, COX inhibitors, methotrexate, anti-TNF drugs, retuxin, PD4 inhibitors, p38 inhibitors, PDE4 inhibitors, and antihistamines, to name a few. The compounds may be administered in the form of compounds per se, or as pharmaceutical compositions comprising a compound.

Pharmaceutical compositions comprising the compound(s) may be manufactured by means of conventional mixing, dissolving, granulating, dragee-making levigating, emulsifying, encapsulating, entrapping or lyophilization processes. The compositions may be formulated in conventional manner using one or more physiologically acceptable carriers, diluents, excipients or auxiliaries which facilitate processing of the compounds into preparations which can be used pharmaceutically.

The compounds may be formulated in the pharmaceutical composition per se, or in the form of a hydrate, solvate, N-oxide or pharmaceutically acceptable salt, as previously described. Typically, such salts are more soluble in aqueous solutions than the corresponding free acids and bases, but salts having lower solubility than the corresponding free acids and bases may also be formed.

Pharmaceutical compositions may take a form suitable for virtually any mode of administration, including, for example, topical, ocular, oral, buccal, systemic, nasal, injection, transdermal, rectal, vaginal, etc., or a form suitable for administration by inhalation or insufflation.

For topical administration, the compound(s) may be formulated as solutions, gels, ointments, creams, suspensions, etc. as are well-known in the art. Systemic formulations include those designed for administration by injection, e.g., subcutaneous, intravenous, intramuscular, intrathecal or intraperitoneal injection, as well as those designed for transdermal, transmucosal oral or pulmonary administration.

Useful injectable preparations include sterile suspensions, solutions or emulsions of the active compound(s) in aqueous or oily vehicles. The compositions may also contain formulating agents, such as suspending, stabilizing and/or dispersing agent. The formulations for injection may be presented in unit dosage form, e.g., in ampules or in multidose containers, and may contain added preservatives. Alternatively, the injectable formulation may be provided in powder form for reconstitution with a suitable vehicle, including but not limited to sterile pyrogen free water, buffer, dextrose solution, etc., before use. To this end, the active compound(s) may be dried by any art-known technique, such as lyophilization, and reconstituted prior to use.

For transmucosal administration, penetrants appropriate to the barrier to be permeated are used in the formulation. Such penetrants are known in the art.

For oral administration, the pharmaceutical compositions may take the form of, for example, lozenges, tablets or capsules prepared by conventional means with pharmaceutically acceptable excipients such as binding agents (e.g., pregelatinised maize starch, polyvinylpyrrolidone or hydroxypropyl methylcellulose); fillers (e.g., lactose, microcrystalline cellulose or calcium hydrogen phosphate); lubricants (e.g., magnesium stearate, talc or silica); disintegrants (e.g., potato starch or sodium starch glycolate); or wetting agents (e.g., sodium lauryl sulfate). The tablets may be coated by methods well known in the art with, for example, sugars, films or enteric coatings.

Liquid preparations for oral administration may take the form of, for example, elixirs, solutions, syrups or suspensions, or they may be presented as a dry product for constitution with water or other suitable vehicle before use. Such liquid preparations may be prepared by conventional means with pharmaceutically acceptable additives such as suspending agents (e.g., sorbitol syrup, cellulose derivatives or hydrogenated edible fats); emulsifying agents (e.g., lecithin or acacia); non-aqueous vehicles (e.g., almond oil, oily esters, ethyl alcohol, Cremophore™ or fractionated vegetable oils); and preservatives (e.g., methyl or propyl-p-hydroxybenzoates or sorbic acid). The preparations may also contain buffer salts, preservatives, flavoring, coloring and sweetening agents as appropriate.

Preparations for oral administration may be suitably formulated to give controlled release of the compound, as is well known.

For buccal administration, the compositions may take the form of tablets or lozenges formulated in conventional manner.

For rectal and vaginal routes of administration, the compound(s) may be formulated as solutions (for retention enemas) suppositories or ointments containing conventional suppository bases such as cocoa butter or other glycerides.

For nasal administration or administration by inhalation or insufflation, the compound(s) can be conveniently delivered in the form of an aerosol spray from pressurized packs or a nebulizer with the use of a suitable propellant, e.g., dichlorodifluoromethane, trichlorofluoromethane, dichlorotetrafluoroethane, fluorocarbons, carbon dioxide or other suitable gas. In the case of a pressurized aerosol, the dosage unit may be determined by providing a valve to deliver a metered amount. Capsules and cartridges for use in an inhaler or insufflator (for example capsules and cartridges comprised of gelatin) may be formulated containing a powder mix of the compound and a suitable powder base such as lactose or starch.

For ocular administration, the compound(s) may be formulated as a solution, emulsion, suspension, etc. suitable for administration to the eye. A variety of vehicles suitable for administering compounds to the eye are known in the art.

For prolonged delivery, the compound(s) can be formulated as a depot preparation for administration by implantation or intramuscular injection. The compound(s) may be formulated with suitable polymeric or hydrophobic materials (e.g., as an emulsion in an acceptable oil) or ion exchange resins, or as sparingly soluble derivatives, e.g., as a sparingly soluble salt. Alternatively, transdermal delivery systems manufactured as an adhesive disc or patch which slowly releases the compound(s) for percutaneous absorption may be used. To this end, permeation enhancers may be used to facilitate transdermal penetration of the compound(s).

Alternatively, other pharmaceutical delivery systems may be employed. Liposomes and emulsions are well-known examples of delivery vehicles that may be used to deliver compound(s). Certain organic solvents such as dimethylsulfoxide (DMSO) may also be employed, although usually at the cost of greater toxicity.

The pharmaceutical compositions may, if desired, be presented in a pack or dispenser device which may contain one or more unit dosage forms containing the compound(s). The pack may, for example, comprise metal or plastic foil, such as a blister pack. The pack or dispenser device may be accompanied by instructions for administration.

The compound(s) described herein, or compositions thereof, will generally be used in an amount effective to achieve the intended result, for example in an amount effective to treat or prevent the particular disease being treated. By therapeutic benefit is meant eradication or amelioration of the underlying disorder being treated and/or eradication or amelioration of one or more of the symptoms associated with the underlying disorder such that the patient reports an improvement in feeling or condition, notwithstanding that the patient may still be afflicted with the underlying disorder. Therapeutic benefit also generally includes halting or slowing the progression of the disease, regardless of whether improvement is realized.

The amount of compound(s) administered will depend upon a variety of factors, including, for example, the particular indication being treated, the mode of administration, whether the desired benefit is prophylactic or therapeutic, the severity of the indication being treated and the age and weight of the patient, the bioavailability of the particular compound(s) the conversation rate and efficiency into active drug compound under the selected route of administration, etc.

Determination of an effective dosage of compound(s) for a particular use and mode of administration is well within the capabilities of those skilled in the art. Effective dosages may be estimated initially from in vitro activity and metabolism assays. For example, an initial dosage of compound for use in animals may be formulated to achieve a circulating blood or serum concentration of the metabolite active compound that is at or above an $IC_{50}$ of the particular compound as measured in as in vitro assay. Calculating dosages to achieve such circulating blood or serum concentrations taking into account the bioavailability of the particular compound via the desired route of administration is well within the capabilities of skilled artisans. Initial dosages of compound can also be estimated from in vivo data, such as animal models. Animal models useful for testing the efficacy of the active metabolites to treat or prevent the various diseases described above are well-known in the art Animal models suitable for testing the bioavailability and/or metabolism of compounds into active metabolites are also well-known. Ordinarily skilled artisans can routinely adapt such information to determine dosages of particular compounds suitable for human administration.

Dosage amounts will typically be in the range of from about 0.0001 mg/kg/day, 0.001 mg/kg/day or 0.01 mg/kg/day to about 100 mg/kg/day, but may be higher or lower, depending upon, among other factors, the activity of the active metabolite compound, the bioavailability of the compound, its metabolism kinetics and other pharmacokinetic properties, the mode of administration and various other factors, discussed above. Dosage amount and interval may be adjusted individually to provide plasma levels of the compound(s) and/or active metabolite compound(s) which are sufficient to maintain therapeutic or prophylactic effect. For example, the compounds may be administered once per week, several times per week (e.g., every other day), once per day or multiple times per day, depending upon, among other things, the mode of administration, the specific indication being treated and the judgment of the prescribing physician. In cases of local administration or selective uptake, such as local topical administration, the effective local concentration of compound(s) and/or active metabolite compound(s) may not be related to plasma concentration. Skilled artisans will be able to optimize effective local dosages without undue experimentation.

DEFINITIONS

The following terms and expressions used herein have the indicated meanings.

Terms used herein may be preceded and/or followed by a single dash, "-", or a double dash, "=", to indicate the bond order of the bond between the named substituent and its parent moiety; a single dash indicates a single bond and a double dash indicates a double bond. In the absence of a single or double dash it is understood that a single bond is formed between the substituent and its parent moiety; further, substituents are intended to be read "left to right" unless a dash indicates otherwise. For example, $C_1$-$C_6$alkoxycarbonyloxy and —OC(O)$C_1$-$C_6$alkyl indicate the same functionality; similarly arylalkyl and -alkylaryl indicate the same functionality.

The term "alkenyl" as used herein, means a straight or branched chain hydrocarbon containing from 2 to 10 carbons, unless otherwise specified, and containing at least one carbon-carbon double bond. Representative examples of alkenyl include, but are not limited to, ethenyl, 2-propenyl, 2-methyl-2-propenyl, 3-butenyl, 4-pentenyl, 5-hexenyl, 2-heptenyl, 2-methyl-1-heptenyl, 3-decenyl, and 3,7-dimethylocta-2,6-dienyl.

The term "alkoxy" as used herein, means an alkyl group, as defined herein, appended to the parent molecular moiety through an oxygen atom. Representative examples of alkoxy include, but are not limited to, methoxy, ethoxy, propoxy, 2-propoxy, butoxy, tert-butoxy, pentyloxy, and hexyloxy.

The term "alkyl" as used herein, means a straight or branched chain hydrocarbon containing from 1 to 10 carbon atoms unless otherwise specified. Representative examples of alkyl include, but are not limited to, methyl, ethyl, n-propyl, iso-propyl, n-butyl, sec-butyl, iso-butyl, tert-butyl, n-pentyl, isopentyl, neopentyl, n-hexyl, 3-methylhexyl, 2,2-dimethylpentyl, 2,3-dimethylpentyl, n-heptyl, n-octyl, n-nonyl, and n-decyl. When an "alkyl" group is a linking group between two other moieties, then it may also be a straight or branched chain; examples include, but are not limited to —$CH_2$—, —$CH_2CH_2$—, —$CH_2CH_2CHC(CH_3)$—, —$CH_2CH(CH_2CH_3)CH_2$—.

The term "alkynyl" as used herein, means a straight or branched chain hydrocarbon group containing from 2 to 10 carbon atoms and containing at least one carbon-carbon triple bond. Representative examples of alkynyl include, but are not limited, to acetylenyl, 1-propynyl, 2-propynyl, 3-butynyl, 2-pentynyl, and 1-butynyl.

The term "aryl," as used herein, means a phenyl (i.e., monocyclic aryl), or a bicyclic ring system containing at least one phenyl ring or an aromatic bicyclic ring containing only carbon atoms in the aromatic bicyclic ring system. The bicyclic aryl can be azulenyl, naphthyl, or a phenyl fused to a monocyclic cycloalkyl, a monocyclic cycloalkenyl, or a monocyclic heterocyclyl. The bicyclic aryl is attached to the parent molecular moiety through any carbon atom contained within the phenyl portion of the bicyclic system, or any carbon atom with the napthyl or azulenyl ring. The fused monocyclic cycloalkyl or monocyclic heterocyclyl portions of the bicyclic aryl are optionally substituted with one or two oxo and/or thia groups. Representative examples of the bicyclic aryls include, but are not limited to, azulenyl, naphthyl, dihydroinden-1-yl, dihydroinden-2-yl, dihydroinden-3-yl, dihydroinden-4-yl, 2,3-dihydroindol-4-yl, 2,3-dihydroindol-5-yl, 2,3-dihydroindol-6-yl, 2,3-dihydroindol-7-yl, inden-1-yl, inden-2-yl, inden-3-yl, inden-4-yl, dihydronaphthalen-2-yl, dihydronaphthalen-3-yl, dihydronaphthalen-4-yl, dihydronaphthalen-1-yl, 5,6,7,8-tetrahydronaphthalen-1-yl, 5,6,7,8-tetrahydronaphthalen-2-yl, 2,3-dihydrobenzofuran-4-yl, 2,3-dihydrobenzofuran-5-yl, 2,3-dihydrobenzofuran-6-yl, 2,3-dihydrobenzofuran-7-yl, benzo[d][1,3]dioxol-4-yl, benzo[d][1,3]dioxol-5-yl, 2H-chromen-2-on-5-yl, 2H-chromen-2-on-6-yl, 2H-chromen-2-on-7-yl, 2H-chromen-2-on-8-yl, isoindoline-1,3-dion-4-yl, isoindoline-1,3-dion-5-yl, inden-1-on-4-yl, inden-1-on-5-yl, inden-1-on-6-yl, inden-1-on-7-yl, 2,3-dihydrobenzo[b][1,4]dioxan-5-yl, 2,3-dihydrobenzo[b][1,4]dioxan-6-yl, 2H-benzo[b][1,4]oxazin3(4H)-on-5-yl, 2H-benzo[b][1,4]oxazin3(4H)-on-6-yl, 2H-benzo[b][1,4]oxazin3(4H)-on-7-yl, 2H-benzo[b][1,4]oxazin3(4H)-on-8-yl, benzo[d]oxazin-2(3H)-on-5-yl, benzo[d]oxazin-2(3H)-on-6-yl, benzo[d]oxazin-2(3H)-on-7-yl, benzo[d]oxazin-2(3H)-on-8-yl, quinazolin-4(3H)-on-5-yl, quinazolin-4(3H)-on-6-yl, quinazolin-4(3H)-on-7-yl, quinazolin-4(3H)-on-8-yl, quinoxalin-2(1H)-on-5-yl, quinoxalin-2(1H)-on-6-yl, quinoxalin-2(1H)-on-7-yl, quinoxalin-2(1H)-on-8-yl, benzo[d]thiazol-2(3H)-on-4-yl, benzo[d]thiazol-2(3H)-on-5-yl, benzo[d]thiazol-2(3H)-on-6-yl, and, benzo[d]thiazol-2(3H)-on-7-yl. In certain embodiments, the bicyclic aryl is (i) naphthyl or (ii) a phenyl ring fused to either a 5 or 6 membered monocyclic cycloalkyl, a 5 or 6 membered monocyclic cycloalkenyl, or a 5 or 6 membered monocyclic heterocyclyl, wherein the fused cycloalkyl, cycloalkenyl, and heterocyclyl groups are optionally substituted with one or two groups which are independently oxo or thia.

The terms "cyano" and "nitrile" as used herein, mean a —CN group.

The term "cycloalkyl" as used herein, means a monocyclic or a bicyclic cycloalkyl ring system. Monocyclic ring systems are cyclic hydrocarbon groups containing from 3 to 8 carbon atoms, where such groups can be saturated or unsaturated, but not aromatic. In certain embodiments, cycloalkyl groups are fully saturated. Examples of monocyclic cycloalkyls include cyclopropyl, cyclobutyl, cyclopentyl, cyclopentenyl, cyclohexyl, cyclohexenyl, cycloheptyl, and cyclooctyl. Bicyclic cycloalkyl ring systems are bridged monocyclic rings or fused bicyclic rings. Bridged monocyclic rings contain a monocyclic cycloalkyl ring where two non-adjacent carbon atoms of the monocyclic ring are linked by an alkylene bridge of between one and three additional carbon atoms (i.e., a bridging group of the form —(CH$_2$)$_w$—, where w is 1, 2, or 3). Representative examples of bicyclic ring systems include, but are not limited to, bicyclo[3.1.1]heptane, bicyclo[2.2.1]heptane, bicyclo[2.2.2]octane, bicyclo[3.2.2]nonane, bicyclo [3.3.1]nonane, and bicyclo[4.2.1]nonane. Fused bicyclic cycloalkyl ring systems contain a monocyclic cycloalkyl ring fused to either a phenyl, a monocyclic cycloalkyl, a monocyclic cycloalkenyl, a monocyclic heterocyclyl, or a monocyclic heteroaryl. The bridged or fused bicyclic cycloalkyl is attached to the parent molecular moiety through any carbon atom contained within the monocyclic cycloalkyl ring. Cycloalkyl groups are optionally substituted with one or two groups which are independently oxo or thia. In certain embodiments, the fused bicyclic cycloalkyl is a 5 or 6 membered monocyclic cycloalkyl ring fused to either a phenyl ring, a 5 or 6 membered monocyclic cycloalkyl, a 5 or 6 membered monocyclic cycloalkenyl, a 5 or 6 membered monocyclic heterocyclyl, or a 5 or 6 membered monocyclic heteroaryl, wherein the fused bicyclic cycloalkyl is optionally substituted by one or two groups which are independently oxo or thia.

The term "halo" or "halogen" as used herein, means —Cl, —Br, —I or —F.

The term "haloalkyl" as used herein, means at least one halogen, as defined herein, appended to the parent molecular moiety through an alkyl group, as defined herein. Representative examples of haloalkyl include, but are not limited to, chloromethyl, 2-fluoroethyl, trifluoromethyl, pentafluoroethyl, and 2-chloro-3-fluoropentyl.

The term "heteroaryl," as used herein, means a monocyclic heteroaryl or a bicyclic ring system containing at least one heteroaromatic ring. The monocyclic heteroaryl can be a 5 or 6 membered ring. The 5 membered ring consists of two double bonds and one, two, three or four nitrogen atoms and optionally one oxygen or sulfur atom. The 6 membered ring consists of three double bonds and one, two, three or four nitrogen atoms. The 5 or 6 membered heteroaryl is connected to the parent molecular moiety through any carbon atom or any nitrogen atom contained within the heteroaryl. Representative examples of monocyclic heteroaryl include, but are not limited to, furyl, imidazolyl, isoxazolyl, isothiazolyl, oxadiazolyl, oxazolyl, pyridinyl, pyridazinyl, pyrimidinyl, pyrazinyl, pyrazolyl, pyrrolyl, tetrazolyl, thiadiazolyl, thiazolyl, thienyl, triazolyl, and triazinyl. The bicyclic heteroaryl consists of a monocyclic heteroaryl fused to a phenyl, a monocyclic cycloalkyl, a monocyclic cycloalkenyl, a monocyclic heterocyclyl, or a monocyclic heteroaryl. The fused cycloalkyl or heterocyclyl portion of the bicyclic heteroaryl group is optionally substituted with one or two groups which are independently oxo or thia. When the bicyclic heteroaryl contains a fused cycloalkyl, cycloalkenyl, or heterocyclyl ring, then the bicyclic heteroaryl group is connected to the parent molecular moiety through any carbon or nitrogen atom contained within the monocyclic heteroaryl portion of the bicyclic ring system. When the bicyclic heteroaryl is a monocyclic heteroaryl fused to a phenyl ring, then the bicyclic heteroaryl group is connected to the parent molecular moiety through any carbon atom or nitrogen atom within the bicyclic ring system. Representative examples of bicyclic heteroaryl include, but are not limited to, benzimidazolyl, benzofuranyl, benzothienyl, benzoxadiazolyl, benzoxathiadiazolyl, benzothiazolyl, cinnolinyl, 5,6-dihydroquinolin-2-yl, 5,6-dihydroisoquinolin-1-yl, furopyridinyl, indazolyl, indolyl, isoquinolinyl, naphthyridinyl, quinolinyl, purinyl, 5,6,7,8-tetrahydroquinolin-2-yl, 5,6,7,8-tetrahydroquinolin-3-yl, 5,6,7,8-tetrahydroquinolin-4-yl, 5,6,7,8-tetrahydroisoquinolin-1-yl, thienopyridinyl, 4,5,6,7-tetrahydrobenzo[c][1,2,5]oxadiazolyl, and 6,7-dihydrobenzo[c][1,2,5]oxadiazol-4 (5H)-onyl. In certain embodiments, the fused bicyclic heteroaryl is a 5 or 6 membered monocyclic heteroaryl ring fused to either a phenyl ring, a 5 or 6 membered monocyclic cycloalkyl, a 5 or 6 membered monocyclic cycloalkenyl, a 5 or 6 membered monocyclic heterocyclyl, or a 5 or 6 membered monocyclic heteroaryl, wherein the fused cycloalkyl, cycloalkenyl, and heterocyclyl groups are optionally substituted with one or two groups which are independently oxo or thia.

The term "heterocyclyl" as used herein, means a monocyclic heterocycle or a bicyclic heterocycle. The monocyclic heterocycle is a 3, 4, 5, 6 or 7 membered ring containing at least one heteroatom independently selected from the group consisting of O, N, and S where the ring is saturated or unsaturated, but not aromatic. The 3 or 4 membered ring contains 1 heteroatom selected from the group consisting of O, N and S. The 5 membered ring can contain zero or one double bond and one, two or three heteroatoms selected from the group consisting of O, N and S. The 6 or 7 membered ring contains zero, one or two double bonds and one, two or three heteroatoms selected from the group consisting of O, N and S. The monocyclic heterocycle is connected to the parent molecular moiety through any carbon atom or any nitrogen atom contained within the monocyclic heterocycle. Representative examples of monocyclic heterocycle include, but are not limited to, azetidinyl, azepanyl, aziridinyl, diazepanyl, 1,3-dioxanyl, 1,3-dioxolanyl, 1,3-dithiolanyl, 1,3-dithianyl, imidazolinyl, imidazolidinyl, isothiazolinyl, isothiazolidinyl, isoxazolinyl, isoxazolidinyl, morpholinyl, oxadiazolinyl, oxadiazolidinyl, oxazolinyl, oxazolidinyl, piperazinyl, piperidinyl, pyranyl, pyrazolinyl, pyrazolidinyl, pyrrolinyl, pyrrolidinyl, tetrahydrofuranyl, tetrahydrothienyl, thiadiazolinyl, thiadiazolidinyl, thiazolinyl, thiazolidinyl, thiomorpholinyl,1,1-dioxidothiomorpholinyl (thiomorpholine sulfone), thiopyranyl, and trithianyl. The bicyclic heterocycle is a monocyclic heterocycle fused to either a phenyl, a monocyclic cycloalkyl, a monocyclic cycloalkenyl, a monocyclic heterocycle, or a monocyclic heteroaryl. The bicyclic heterocycle is connected to the parent molecular moiety through any carbon atom or any nitrogen atom contained within the monocyclic heterocycle portion of the bicyclic ring system. Representative examples of bicyclic heterocyclyls include, but are not limited to, 2,3-dihydrobenzofuran-2-yl, 2,3-dihydrobenzofuran-3-yl, indolin-1-yl, indolin-2-yl, indolin-3-yl, 2,3-dihydrobenzothien-2-yl, decahydroquinolinyl, decahydroisoquinolinyl, octahydro-1H-indolyl, and octahydrobenzofuranyl. Heterocyclyl groups are optionally substituted with one or two groups which are independently oxo or thia. In certain embodiments, the bicyclic heterocyclyl is a 5 or 6 membered monocyclic heterocyclyl ring fused to phenyl ring, a 5 or 6 membered monocyclic cycloalkyl, a 5 or 6 membered monocyclic cycloalkenyl, a 5 or 6 membered monocyclic heterocyclyl, or a 5 or 6 membered monocyclic heteroaryl, wherein the bicyclic heterocyclyl is optionally substituted by one or two groups which are independently oxo or thia.

The term "nitro" as used herein, means a —NO$_2$ group.

The term "oxo" as used herein means a =O group.

The term "saturated" as used herein means the referenced chemical structure does not contain any multiple carbon-carbon bonds. For example, a saturated cycloalkyl group as defined herein includes cyclohexyl, cyclopropyl, and the like.

The term "thia" as used herein means a =S group.

The term "unsaturated" as used herein means the referenced chemical structure contains at least one multiple carbon-carbon bond, but is not aromatic. For example, a unsaturated cycloalkyl group as defined herein includes cyclohexenyl, cyclopentenyl, cyclohexadienyl, and the like.

"Pharmaceutically acceptable" refers to those compounds, materials, compositions, and/or dosage forms which are, within the scope of sound medical judgment, suitable for contact with the tissues of human beings and animals without excessive toxicity, irritation, allergic response, or other problems or complications commensurate with a reasonable benefit/risk ratio or which have otherwise been approved by the United States Food and Drug Administration as being acceptable for use in humans or domestic animals.

"Pharmaceutically acceptable salt" refers to both acid and base addition salts.

"Prodrug" refers to compounds that are transformed (typically rapidly) in vivo to yield the parent compound of the above formulae, for example, by hydrolysis in blood. Common examples include, but are not limited to, ester and amide forms of a compound having an active form bearing a carboxylic acid moiety. Examples of pharmaceutically acceptable esters of the compounds of this invention include, but are not limited to, alkyl esters (for example with between about one and about six carbons) wherein the alkyl group is a straight or branched chain. Acceptable esters also include cycloalkyl esters and arylalkyl esters such as, but not limited to benzyl. Examples of pharmaceutically acceptable amides of the compounds of this invention include, but are not limited to, primary amides, and secondary and tertiary alkyl amides (for example with between about one and about six carbons). Amides and esters of the compounds of the present invention may be prepared according to conventional methods. A thorough discussion of prodrugs is provided in T. Higuchi and V. Stella, "Pro-drugs as Novel Delivery Systems," Vol 14 of the A.C.S. Symposium Series, and in Bioreversible Carriers in Drug Design, ed. Edward B. Roche, American Pharmaceutical Association and Pergamon Press, 1987, both of which are incorporated herein by reference for all purposes.

"Therapeutically effective amount" refers to that amount of a compound which, when administered to a subject, is sufficient to effect treatment for a disease or disorder described herein. The amount of a compound which constitutes a "therapeutically effective amount" will vary depending on the compound, the disorder and its severity, and the age of the subject to be treated, but can be determined routinely by one of ordinary skill in the art.

"Modulating" or "modulate" refers to the treating, prevention, suppression, enhancement or induction of a function, condition or disorder. For example, it is believed that the compounds of the present invention can modulate atherosclerosis by stimulating the removal of cholesterol from atherosclerotic lesions in a human.

"Treating" or "treatment" as used herein covers the treatment of a disease or disorder described herein, in a subject, preferably a human, and includes:
  i. inhibiting a disease or disorder, i.e., arresting its development;
  ii. relieving a disease or disorder, i.e., causing regression of the disorder;
  iii. slowing progression of the disorder; and/or
  iv. inhibiting, relieving, or slowing progression of one or more symptoms of the disease or disorder "Subject" refers to a warm blooded animal such as a mammal, preferably a human, or a human child, which is afflicted with, or has the potential to be afflicted with one or more diseases and disorders described herein.

"$EC_{50}$" refers to a dosage, concentration or amount of a particular test compound that elicits a dose-dependent response at 50% of maximal expression of a particular response that is induced, provoked or potentiated by the particular test compound.

"$IC_{50}$" refers to an amount, concentration or dosage of a particular test compound that achieves a 50% inhibition of a maximal response in an assay that measures such response.

"Respiratory chain lesions" in mitochondria or "Mitochondria with respiratory chain lesions" refers to mitochondria in which the structures of the five complexes responsible for ATP production by oxidative phosphorylation are altered structurally, typically in a way that leads to diminished function.

Methods of Synthesis

Many general references providing commonly known chemical synthetic schemes and conditions useful for synthesizing the disclosed compounds are available (see, e.g., Smith and March, March's Advanced Organic Chemistry: Reactions, Mechanisms, and Structure, Fifth Edition, Wiley-Interscience, 2001; or Vogel, A Textbook of Practical Organic Chemistry, Including Qualitative Organic Analysis, Fourth Edition, New York: Longman, 1978).

Compounds as described herein can be purified by any of the means known in the art, including chromatographic means, such as HPLC, preparative thin layer chromatography, flash column chromatography and ion exchange chromatography. Any suitable stationary phase can be used, including normal and reversed phases as well as ionic resins. Most typically the disclosed compounds are purified via silica gel and/or alumina chromatography. See, e.g., Introduction to Modern Liquid Chromatography, 2nd Edition, ed. L. R. Snyder and J. J. Kirkland, John Wiley and Sons, 1979; and Thin Layer Chromatography, ed E. Stahl, Springer-Verlag, New York, 1969.

During any of the processes for preparation of the subject compounds, it may be necessary and/or desirable to protect sensitive or reactive groups on any of the molecules concerned. This may be achieved by means of conventional protecting groups as described in standard works, such as J. F. W. McOmie, "Protective Groups in Organic Chemistry", Plenum Press, London and New York 1973, in T. W. Greene and P. G. M. Wuts, "Protective Groups in Organic Synthesis", Third edition, Wiley, New York 1999, in "The Peptides"; Volume 3 (editors: E. Gross and J. Meienhofer), Academic Press, London and New York 1981, in "Methoden der organischen Chemie", Houben-Weyl, 4.sup.th edition, Vol. 15/1, Georg Thieme Verlag, Stuttgart 1974, in H.-D. Jakubke and H. Jescheit, "Aminosauren, Peptide, Proteine", Verlag Chemie, Weinheim, Deerfield Beach, and Basel 1982, and/or in Jochen Lehmann, "Chemie der Kohlenhydrate: Monosaccharide and Derivate", Georg Thieme Verlag, Stuttgart 1974. The protecting groups may be removed at a convenient subsequent stage using methods known from the art.

Representative synthetic procedures for the preparation of compounds of the invention are outlined below.

Scheme 1

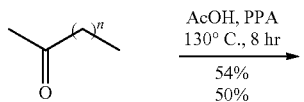

AcOH, PPA
130° C., 8 hr
54%
50%

2-decanone (n = 7)
2-hexadecanone (n = 16)

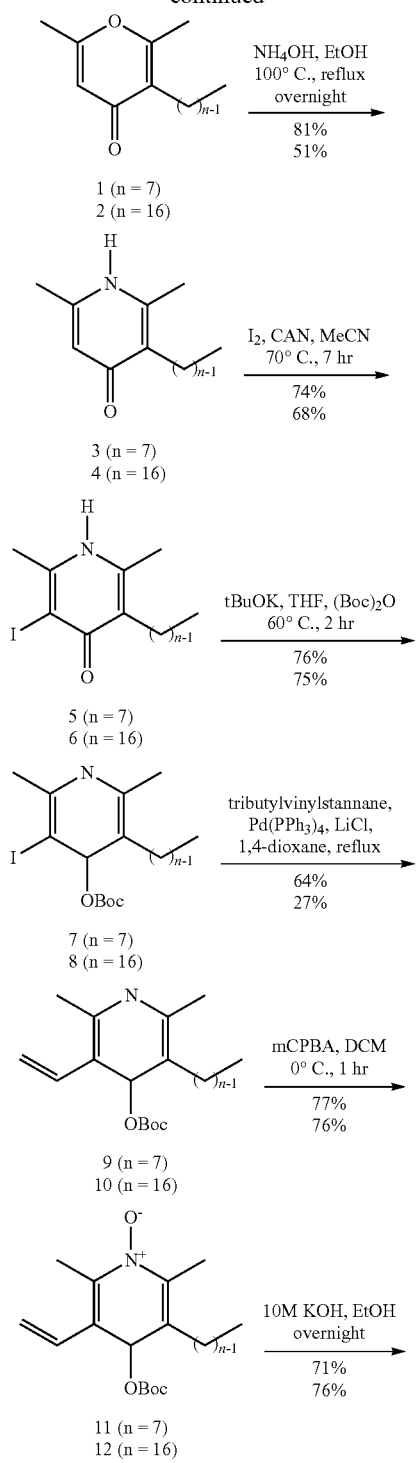
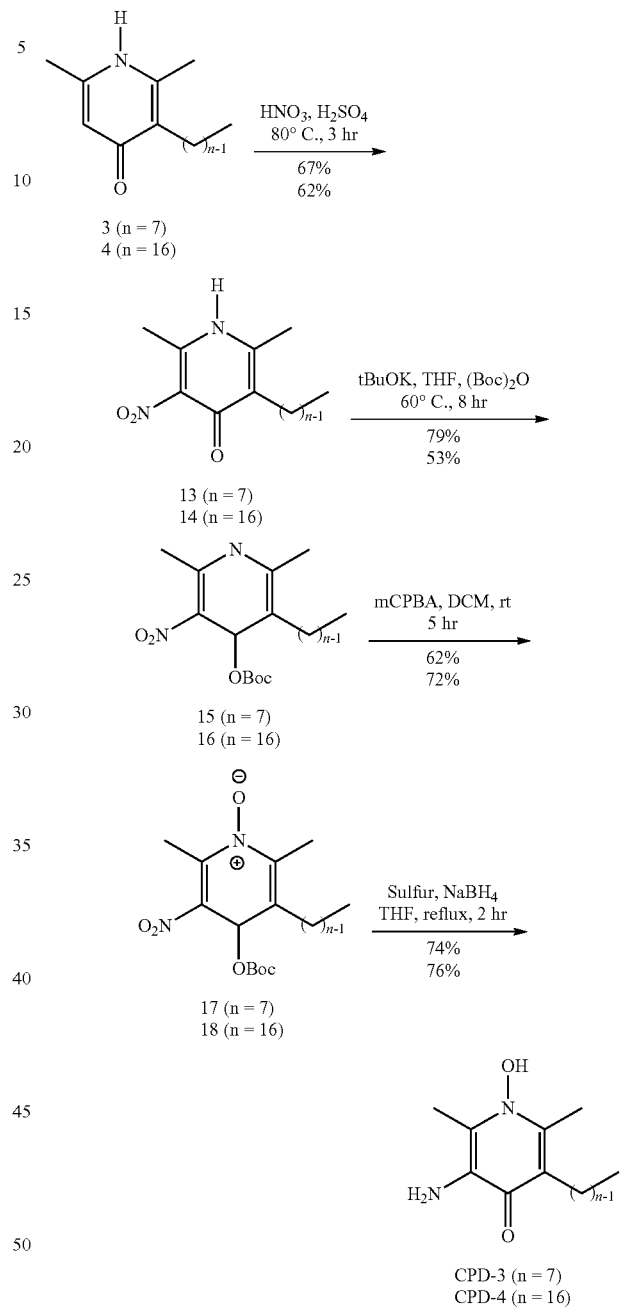
Scheme 2
Scheme 3
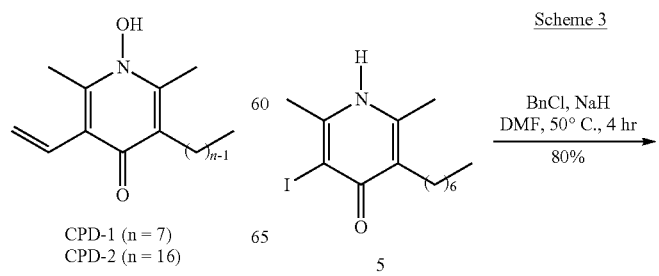

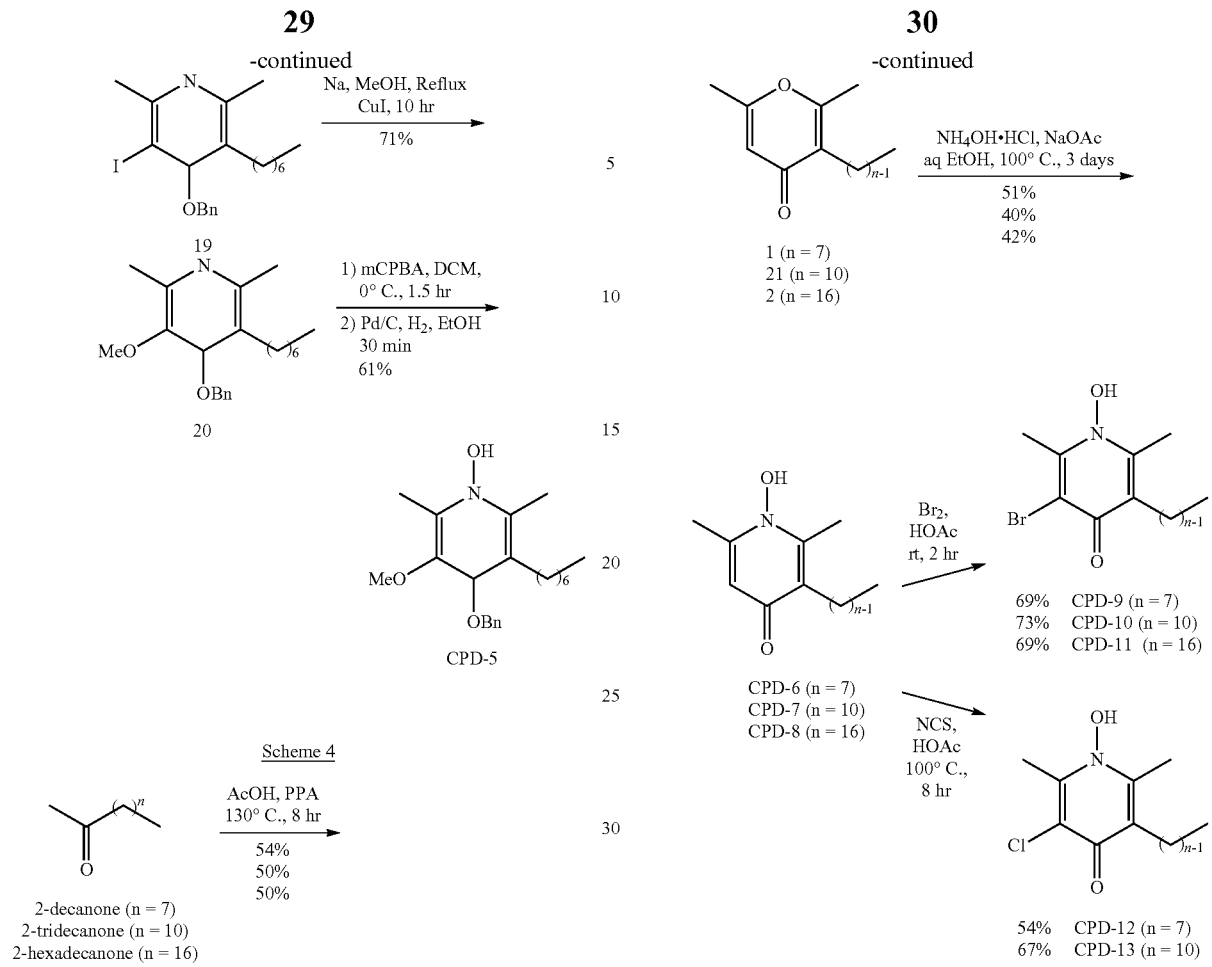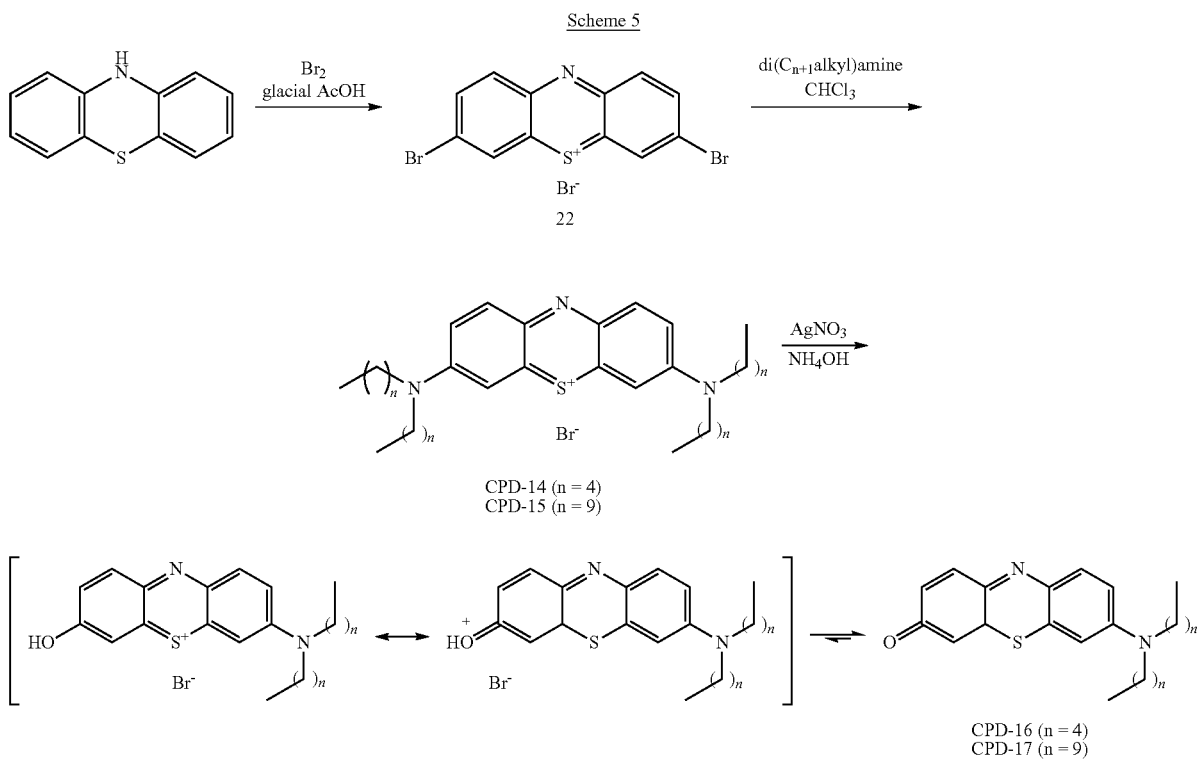

Scheme 6

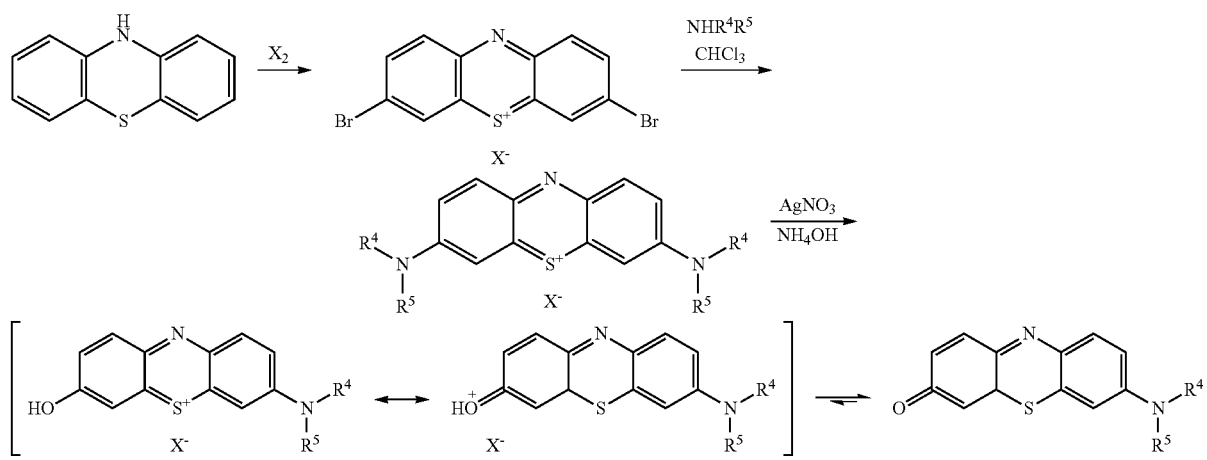

Scheme 7

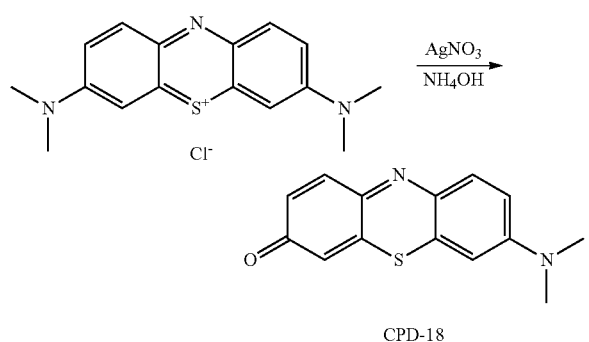

CPD-18

EXAMPLES

The compounds and methods of the disclosure are illustrated further by the following examples, which are provided for illustrative purposes and are not intended to be construed as limiting the disclosure in scope or spirit to the specific compounds and methods described in them.

Example 1

Preparation of 3-heptyl-1-hydroxy-2,6-dimethyl-5-vinylpyridin-4(1H)-one

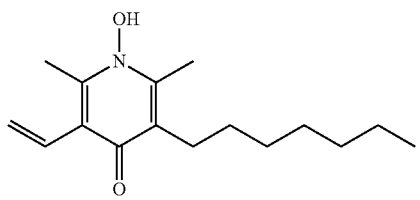 [SMILES: C=Cc1c(C)n(O)c(C)c(CCCCCCC)c1=O]

3-heptyl-1-hydroxy-2,6-dimethyl-5-vinylpyridin-4(1H)-one (CPD-1)

To a mixture of 49 g of polyphosphoric acid and 30 mL of acetic acid was added 0.6 mL (0.5 g, 2.9 mmol) of 2-decanone. The resulting solution was heated at 130° C. with vigorous stirring for 8 h. The resulting dark black solution was cooled to 0° C. and 100 mL of water was added. The mixture was extracted with portions of ethyl ether. The combined organic phase was washed with 10% aqueous KOH, dried over anhydrous $MgSO_4$ and concentrated under diminished pressure to afford a crude residue. The residue was purified by chromatography on a silica gel column. Elution with hexane/ethyl acetate gave 3-heptyl-2,6-dimethyl-4H-pyran-4-one (1) as a light yellow solid: yield 555 mg (54%); silica gel TLC $R_f$ 0.45 (1:1 hexane/ethyl acetate); $^1$H NMR (400 MHz, $CDCl_3$) δ 0.45-0.50 (m, 3H), 0.88-1.04 (m, 10H), 1.82 (s, 3H), 1.89 (s, 3H), 1.98 (t, 2H, J=7.6 Hz), and 5.62 (s, 1H); $^{13}C$ NMR ($CDCl_3$) δ 13.3, 16.6, 18.9, 21.9, 23.6, 27.8, 28.5, 28.9, 31.1, 112.1, 124.0, 160.6, 163.5, and 178.4.

Compound 1 (0.01 g, 30.6 mmol) was heated at 100° C. with aqueous ammonia in a high pressure tube for 18 h. After the mixture was cooled to room temperature, the crude was concentrated under diminished pressure. The residue was purified by chromatography on a silica gel column. Elution with 5:1 ethyl acetate/methanol gave 3-heptyl-2,6-dimethylpyridin-4(1H)-one (3) as a brown solid: yield 0.083 g (81%); silica gel TLC $R_f$ 0.25 (3:1 ethyl acetate/methanol); $^1$H NMR ($CD_3OD$) δ 0.68-0.71 (m, 3H), 1.09-1.28 (m, 10H), 2.20 (s, 3H), 2.27 (s, 3H), 2.34-2.36 (m, 2H) and 6.29 (s, 1H).

To a solution of 3 (100 mg, 0.45 mmol) in acetonitrile (2.5 mL) was added ceric ammonium nitrate (25 mg, 0.045 mmol) followed by iodine (126 mg, 0.495 mmol). The reaction mixture was stirred at 70° C. under nitrogen for 7 h. After completion of the reaction, the mixture was cooled to room temperature and treated with an ice-cold aqueous solution of sodium thiosulfate with stirring. The mixture was extracted with portions of ethyl ether. The combined organic phase was dried over anhydrous $MgSO_4$ and concentrated under diminished pressure to afford a crude residue. The residue was purified by chromatography on a silica gel column. Elution with hexane/ethyl acetate gave 3-heptyl-5-iodo-2,6-dimethylpyridin-4(1H)-one (5) as a light yellow solid: yield 119 mg (74%); silica gel TLC $R_f$ 0.45 (1:1 hexane/ethyl acetate); $^1$H NMR (400 MHz, $CDCl_3$) δ 0.88-0.91 (m, 3H), 1.29-1.35 (m, 10H), 2.33 (s, 3H) and 2.54-2.56 (m, 5H).

A mixture of t-BuOK (102 mg, 0.912 mmol) and 5 (0.06 g, 0.73 mmol) in anhydrous THF was stirred for 1 hr at room temperature $Boc_2O$ (175 mg, 0.80 mmol) was added and the mixture was heated at 60° C. for 1 h. After the mixture was cooled to room temperature, the crude was concentrated under diminished pressure to afford a yellow oil. The residue was purified by chromatography on a silica gel column. Elution with 1:1 hexane/ethyl acetate gave 3-iodo-5-heptyl-2,6-dimethylpyridin-4-yl tert-butyl carbonate (7) as a light yellow oil: yield 61 mg (76%); silica gel TLC $R_f$ 0.7 (1:1 hexane/ethyl acetate); $^1$H NMR (CDCl$_3$) δ 0.83-0.86 (m, 3H), 1.22-1.32 (m, 10H), 1.52 (s, 9H), 2.35 (s, 3H) and 2.51-2.54 (m, 5H).

To a solution of 7 (60 mg, 0.864 mmol) in 1,4-dioxane (4 ml) were added lithium chloride (73.2 mg, 1.73 mmol), tetrakis(triphenylphosphine)palladium (99.8 mg, 10 mol %) and tributyl(vinyl)tin (0.327 ml, 1.12 mmol). The mixture was heated at reflux for 3 h then cooled and diluted with CHCl$_3$. The mixture was washed with brine, dried over Na$_2$SO$_4$, filtered, and concentrated in under diminished pressure. The residue was purified by column chromatography on silica gel [AcOEt/MeOH (20:1)] to afford tert-butyl 3-heptyl-2,6-dimethyl-5-vinylpyridin-4-yl carbonate (9) (30 mg, 64%). $^1$H NMR (CDCl$_3$) δ 0.85-0.88 (m, 3H), 1.27-1.32 (m, 10H), 1.47 (s, 9H), 2.40 (s, 3H), 2.43 (s, 3H), 2.47-2.50 (m, 2H), 5.50 (dd, 2H, J=18 Hz, 11.2 Hz) and 6.45 (dd, 1H, J=11.6 Hz, 11.6 Hz).

A solution of 9 (30 mg, 0.66 mmol) and mCPBA (125 mg, 0.72 mmol) in anhydrous CH$_2$Cl$_2$ (2 mL) was stirred at 0° C. for 1 hr under argon atmosphere. The crude was concentrated under diminished pressure. The residue was purified by chromatography on a silica gel column. Elution with 1:1 hexane/ethyl acetate gave tert-butyl-3-heptyl-2,6-dimethyl-5-vinylpyridin-4-yl-carbonate-N-oxide (11) as a light yellow oil: yield 24 mg (77%); silica gel TLC $R_f$ 0.25 (ethyl acetate); $^1$H NMR (CDCl$_3$) δ 0.85-0.88 (m, 3H), 1.26-1.32 (m, 10H), 1.50 (s, 9H), 2.50 (s, 3H), 2.52 (s, 3H), 2.55-2.57 (m, 2H), 5.56 (dd, 2H, J=18 Hz, 11.2 Hz) and 6.54 (dd, 1H, J=11.6 Hz, 11.6 Hz).

Aqueous 10 M KOH was added to a solution of 11 (138 mg, 0.54 mmol) in EtOH (1.5 mL). After 12 hr at room temperature water (3 mL) was added and pH was brought to 1-2 using concentrated HCl, The mixture was extracted with portions of ethyl ether. The combined organic phase was dried over anhydrous MgSO$_4$ and concentrated under diminished pressure to afford a crude residue. Elution with 5:1 chloroform/methanol gave 3-heptyl-1-hydroxy-2,6-dimethyl-5-vinylpyridin-4(1H)-one (CPD-1) as a light yellow oil: yield 12 mg (71%); silica gel TLC $R_f$ 0.35 (1:1 ethyl acetate/methanol); $^1$H NMR (CDCl$_3$) δ 0.87 (m, 3H), 1.26-1.39 (m, 10H), 2.39 (s, 3H), 2.47 (s, 3H), 2.60 (m, 2H), 5.57 (dd, 2H, J=18 Hz, 11.6 Hz) and 6.54 (dd, 1H, J=11.6 Hz, 11.2 Hz).

Example 2

Preparation of 3-hexadecyl-1-hydroxy-2,6-dimethyl-5-vinylpyridin-4(1H)-one

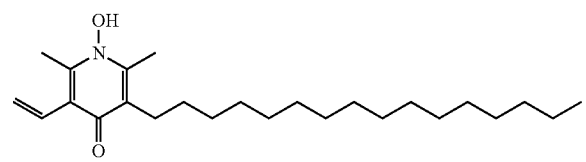 [SMILES: C=Cc1c(C)n(O)c(C)c(CCCCCCCCCCCCCCCC)c1=O]

3-hexadecyl-1-hydroxy-2,6-dimethyl-5-vinylpyridin-4(1H)-one (CPD-2)

To a mixture of 49 g of polyphosphoric acid and 30 mL of acetic acid was added 0.6 mL (0.5 g, 1.77 mmol) of 2-nonadecanone. The resulting solution was heated at 130° C. with vigorous stirring for 8 h. The resulting dark black solution was cooled to 0° C. and 100 mL of water was added. The mixture was extracted with portions of ethyl ether. The combined organic phase was washed with 10% aqueous KOH, dried over anhydrous MgSO$_4$ and concentrated under diminished pressure to afford a crude residue. The residue was purified by chromatography on a silica gel column. Elution with chloroform gave 3-hexadecyl-2,6-dimethyl-4H-pyran-4-one (2) as a light yellow solid: yield 331 mg (50%); silica gel TLC $R_f$ 0.6 (1:1 hexane/ethyl acetate); $^1$H NMR (CDCl$_3$, 400 MHz) δ 0.78-0.82 (m, 3H), 1.18-1.24 (m, 28H), 2.14 (s, 3H), 2.21 (s, 3H), 2.30 (t, 2H, J=8 Hz) and 6.06 (s, 1H).

Compound 2 (0.02 g, 30.6 mmol) was heated at 100° C. with aqueous ammonia in a high pressure tube for 18 h. After the mixture was cooled to room temperature, the crude was concentrated under diminished pressure. The residue was purified by chromatography on a silica gel column. Elution with 5:1 ethyl acetate/methanol gave 3-hexadecyl-2,6-dimethylpyridin-4(1H)-one (4) as a brown solid; yield 0.01 g (51%); silica gel TLC $R_f$ 0.25 (3:1 ethyl acetate/methanol); $^1$H NMR (CDCl$_3$, 400 MHz) δ 0.88-0.89 (m, 3H), 1.28-1.32 (m, 28H), 2.28 (s, 3H), 2.34 (s, 3H), 2.44-2.47 (m, 2H) and 6.18 (s, 1H).

To a solution of 4 (100 mg, 4.52 mmol) in acetonitrile (25 mL) was added ceric ammonium nitrate (0.248 g, 0.45 mmol) followed by iodine (0.631 g, 4.97 mmol). The mixture was stirred at 70° C. under nitrogen for 7 h. After completion of the reaction, the mixture was cooled to room temperature and treated with an ice-cold aqueous solution of sodium thiosulfate with stirring. The mixture was extracted with portions of ethyl ether. The combined organic phase was dried over anhydrous MgSO$_4$ and concentrated under diminished pressure to afford a crude residue. The residue was purified by chromatography on a silica gel column. Elution with hexane/ethyl acetate gave 3-hexadecyl-5-iodo-2,6-dimethylpyridin-4(1H)-one (6) as a light yellow solid: yield 93 mg (68%); silica gel TLC $R_f$ 0.60 (1:1 hexane/ethyl acetate); $^1$H NMR (400 MHz, CDCl$_3$) δ 0.86-0.89 (m, 3H), 1.24-1.28 (m, 28H), 2.20 (s, 3H), 2.26 (s, 3H) and 2.32-2.39 (m, 2H).

A mixture of t-BuOK (102 mg, 0.912 mmol) and 2,3,6-trimethylpyridin-4(1H)-one(1) (0.1 g, 0.73 mmol) in anhydrous THF was stirred for 1 hr at room temperature Boc$_2$O (175 mg, 0.80 mmol) was added and the mixture was heated at 60° C. for 1 h. After the mixture was cooled to room temperature, the crude was concentrated under diminished pressure to a yellow oil. The residue was purified by chromatography on a silica gel column. Elution with 1:1 hexane/ethyl acetate gave tert-butyl 3-hexadecyl-5-iodo-2,6-dimethylpyridin-4-yl carbonate (8) as a light yellow oil: yield 85 mg (75%); silica gel TLC $R_f$ 0.85 (1:1 hexane/ethyl acetate); $^1$H NMR (CDCl$_3$) δ 0.85-0.89 (m, 3H), 1.25-1.31 (m, 28H), 1.57 (s, 9H), 2.50 (s, 3H), 2.52-2.56 (m, 2H) and 2.72 (s, 3H)

To a solution of 8 (85 mg, 0.864 mmol) in 1,4-dioxane (4 ml) were added lithium chloride (73.2 mg, 1.73 mmol), tetrakis(triphenylphosphine)palladium (99.8 mg, 10 mol %) and tributyl(vinyl)tin (0.327 ml, 1.12 mmol). The mixture was heated at reflux for 3 h then cooled and diluted with CHCl$_3$. The mixture was washed with brine, dried over Na$_2$SO$_4$, filtered, and concentrated in under diminished pressure. The residue was purified by column chromatography on silica gel [AcOEt/MeOH (20:1)] to afford tert-butyl 3-hexadecyl-2,6-dimethyl-5-vinylpyridin-4-yl carbonate (10) (19 mg, 27%). $^1$H NMR (CDCl$_3$) δ 0.02-0.03 (m, 3H), 1.20-1.27 (m, 28H), 1.46 (s, 9H), 2.45 (s, 3H), 2.48 (s, 3H), 2.54-2.56 (m, 2H), 5.55 (dd, 2H, J=17.6 Hz, 11.6 Hz) and 6.50 (dd, 1H, J=11.2 Hz, 11.2 Hz).

A solution of 10 (30 mg, 0.66 mmol) and mCPBA (125 mg, 0.72 mmol) in anhydrous $CH_2Cl_2$ (2 mL) was stirred at 0° C. for 1 h under argon atmosphere. The crude product was concentrated under diminished pressure. The residue was purified by chromatography on a silica gel column. Elution with 1:1 hexane/ethyl acetate gave tert-butyl-3-hexadecyl-2,6-dimethyl-5-vinylpyridin-4-yl-carbonate-N-oxide (12) as a light yellow oil: yield 23 mg (76%); silica gel TLC $R_f$ 0.45 (ethyl acetate); $^1$H NMR ($CDCl_3$) δ 0.015-0.03 (m, 3H), 1.17-1.20 (m, 28H), 1.48 (s, 9H), 2.55 (s, 3H), 2.58 (s, 3H), 2.60-2.62 (m, 2H), 5.62 (dd, 2H, J=17.6 Hz, 11.6 Hz) and 6.568 (dd, 1H, J=11.2 Hz, 11.2 Hz).

Aqueous 10 M KOH was added to a solution of 12 (23 mg, 0.54 mmol) in EtOH (1.5 mL). After 12 hr at room temperature, water (3 mL) was added and pH was brought to 1-2 using concentrated HCl, The mixture was extracted with portions of ethyl ether. The combined organic phase was dried over anhydrous $MgSO_4$ and concentrated under diminished pressure to afford a crude residue. Elution with 5:1 chloroform/methanol gave 3-hexadecyl-1-hydroxy-2,6-dimethyl-5-vinylpyridin-4 (1H)-one (CPD-2) as a light yellow oil: yield 13 mg (76%); silica gel TLC $R_f$ 0.25 (3:1 ethyl acetate/methanol); $^1$H NMR ($CDCl_3$) δ 0.02-0.04 (m, 3H), 1.17-1.24 (m, 28H), 2.45 (s, 3H), 2.52 (s, 3H), 2.61-2.65 (m, 2H), 5.64 (dd, 2H, J=17.6 Hz, 11.2 Hz) and 6.57 (dd, 1H, J=11.6 Hz, 11.2 Hz).

Example 3

Preparation of 3-amino-5-heptyl-1-hydroxy-2,6-dimethylpyridin-4(1H)-one

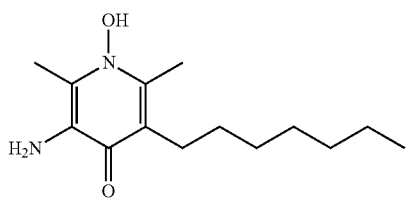 [SMILES: CCCCCCCc1c(C)n(O)c(C)c(N)c1=O]

3-amino-5-heptyl-1-hydroxy-2,6-dimethylpyridin-4 (1H)-one (CPD-3)

Premixed nitric acid (d 1.5, 0.15 g) and sulfuric acid (0.05 g) was added dropwise at 5-10° C. to 3 (94 mg) in sulfuric acid (d 1.64, 0.5 g). The mixture was heated at 80° C. for 1 hr then cooled and added to ice. Saturated aqueous sodium carbonate was added until effervescence ceased. The mixture was extracted with portions of ethyl ether. The combined organic phase was dried over anhydrous $MgSO_4$ and concentrated under diminished pressure to afford a crude residue. Elution with hexane/ethyl acetate gave 3-heptyl-2,6-dimethyl-5-nitropyridin-4(1H)-one (13) as a yellow oil: yield 76 mg (67%); silica gel TLC $R_f$ 0.45 (1:1 hexane/ethyl acetate); $^1$H NMR (400 MHz, $CDCl_3$) δ 0.77-0.81 (m, 3H), 1.19-1.27 (m, 10H), 2.29 (s, 3H), 2.35 (s, 3H) and 2.44-2.47 (m, 2H).

A mixture of t-BuOK (40 mg, 0.36 mmol, 1.25) and 13 (76 mg, 0.29 mmol) in anhydrous THF was stirred for 1 hr at room temperature $Boc_2O$ (63 mg, 0.32 mmol) was added and the mixture was heated at 60° C. for 5 h. After the mixture was cooled to room temperature, the crude product was concentrated under diminished pressure to afford a yellow oil. The residue was purified by chromatography on a silica gel column. Elution with 1:1 hexane/ethyl acetate gave tert-butyl 3-heptyl-2,6-dimethyl-5-nitropyridin-4-yl carbonate (15) as a light yellow oil; yield 81 mg (79%); silica gel TLC $R_f$ 0.7 (1:1 hexane/ethyl acetate); $^1$H NMR (400 MHz, CDCl3) δ 0.79-0.83 (m, 3H), 1.18-1.28 (m, 10H), 1.48 (s, 9H) and 2.48-2.51 (m, 8H).

A solution of 15 (28 mg, 0.077 mmol) and mCPBA (15 mg, 0.084 mmol) in anhydrous $CH_2Cl_2$ (2 mL) was stirred at 0° C. for 1 hr under argon atmosphere. The crude product was concentrated under diminished pressure. The residue was purified by chromatography on a silica gel column. Elution with 1:1 hexane/ethyl acetate gave tert-butyl 3-heptyl-2,6-dimethyl-5-nitropyridin-4-yl carbonate-N-oxide (17) as a light brown solid; yield 18 mg (62%); silica gel TLC $R_f$ 0.40 (ethyl acetate); $^1$H NMR ($CDCl_3$) δ 1.12 (s, 9H), 1.74 (s, 3H), 2.06 (s, 3H), 2.10 (s, 3H) and 6.63 (s, 1H).

To a mixture of 15 mg of solid $NaBH_4$ (11 mg, 0.29 mmol) and 45 mg of sulfur (32 mg, 1.012 mmol) was added 3 mL of anhydrous THF dropwise. After the mixture was stirred for 5 min, 18 mg of compound 17 (0.047 mmol) was added in 1 mL of THF. The reaction mixture was heated at reflux for 1 h, the reaction mixture was cooled to room temperature, the crude product was concentrated under diminished pressure to a afford yellow oil. The residue was purified by chromatography on a silica gel column. Elution with 10:1 ethyl acetate/methanol gave 3-amino-5-heptyl-1-hydroxy-2,6-dimethylpyridin-4(1H)-one (CPD-3) as a light yellow oil: yield 8 mg (74%); silica gel TLC $R_f$ 0.25 (1:1 ethyl acetate/methanol); $^1$H NMR ($CDCl_3$) δ 0.86-0.90 (m, 3H), 1.25-1.32 (m, 10H) and 2.35-2.45 (m, 8H).

Example 4

Preparation of 3-amino-5-hexadecyl-1-hydroxy-2,6-dimethylpyridin-4(1H)-one

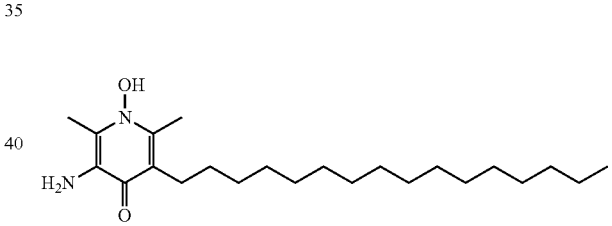

3-amino-5-hexadecyl-1-hydroxy-2,6-dimethylpyridin-4(1H)-one (CPD-4)

Premixed nitric acid (d 1.5, 0.15 g) and sulfuric acid (0.05 g) was added dropwise at 5-10° C. to 4 (58 mg) in sulphuric acid (d 1.64, 0.5 g). The reaction mixture was heated at 80° C. for 1 hr then cooled and added to ice. Saturated aqueous sodium carbonate was added until effervescence ceased. The reaction mixture was extracted with portions of ethyl ether. The combined organic phase was dried over anhydrous $MgSO_4$ and concentrated under diminished pressure to afford a crude residue Elution with hexane/ethyl acetate gave 3-hexadecyl-2,6-dimethyl-5-nitropyridin-4(1H)-one (14) as a yellow oil: yield 41 mg (62%); silica gel TLC $R_f$ 0.60 (1:1 hexane/ethyl acetate); $^1$H NMR (400 MHz, CDCl3) δ 0.82-0.85 (m, 3H), 1.21-1.29 (m, 28H), 2.33 (s, 3H), 2.39 (s, 3H) and 2.46-2.52 (m, 2H).

A mixture of t-BuOK (13 mg, 0.113 mmol) and 14 (41 g, 0.08 mmol) in anhydrous THF was stirred for 1 hr at room temperature $Boc_2O$ (20 mg, 0.09 mmol) was added and the reaction mixture was heated at 60° C. for 5 hr. After the mixture was cooled to room temperature, the crude product was concentrated under diminished pressure to afford a yellow oil. The residue was purified by chromatography on a silica gel column. Elution with 1:1 hexane/ethyl acetate gave tert-butyl 3-hexadecyl-2,6-dimethyl-5-nitropyridin-4-yl carbonate (16) as a light yellow oil: yield 27 mg (53%); silica gel TLC $R_f$ 0.85 (1:1 hexane/ethyl acetate); $^1$H NMR (CDCl$_3$) δ 0.84-0.87 (m, 3H), 1.23-1.34 (m, 28H), 1.52 (s, 9H), 2.44-2.50 (m, 2H) and 2.53-2.56 (s, 6H).

A solution of 16 (27 mg, 0.05 mmol) and mCPBA (10 mg, 0.06 mmol) in anhydrous CH$_2$Cl$_2$ (2 mL) was stirred at 0° C. for 1 hr under argon atmosphere. The crude product was concentrated under diminished pressure. The residue was purified by chromatography on a silica gel column. Elution with 1:1 hexane/ethyl acetate gave tert-butyl 3-hexadecyl-2,6-dimethyl-5-nitropyridin-4-yl carbonate-N-oxide (18) as a light brown solid; yield 20 mg (72%); silica gel TLC $R_f$ 0.50 (ethyl acetate); $^1$H NMR (CDCl$_3$) δ 0.84-0.88 (m, 3H), 1.22-1.30 (m, 28H), 1.54 (s, 9H), 2.56-2.60 (m, 5H) and 2.62 (s, 3H).

To a mixture of 9.0 mg of solid NaBH$_4$ (0.24 mmol) and 21 mg of sulfur (0.646 mmol) was added 3 mL of anhydrous THF dropwise. After the reaction mixture was stirred for 5 min, 20 mg of 18 (0.03 mmol) was added in 1 mL of THF. The reaction mixture was heated at reflux for 1 h, the reaction mixture was cooled to room temperature, the crude product was concentrated under diminished pressure to afford a yellow oil. The residue was purified by chromatography on a silica gel column. Elution with 10:1 ethyl acetate/methanol gave 3-amino-5-hexadecyl-1-hydroxy-2,6-dimethylpyridin-4(1H)-one (CPD-4) as a light yellow oil: yield 11 mg (76%); silica gel TLC $R_f$ 0.35 (1:1 ethyl acetate/methanol); $^1$H NMR (CDCl$_3$) δ 0.85-0.90 (m, 3H), 1.20-1.32 (m, 28H) and 2.22-2.52 (m, 8H)

Example 5

Preparation of 3-heptyl-1-hydroxy-5-methoxy-2,6-dimethylpyridin-4(1H)-one

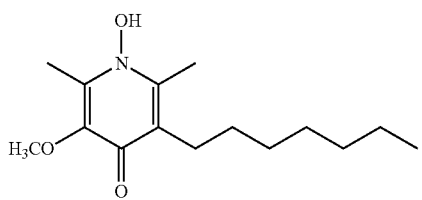 [SMILES: CCCCCCCc1c(C)n(O)c(C)c(OC)c1=O]

3-heptyl-1-hydroxy-5-methoxy-2,6-dimethylpyridin-4(1H)-one (CPD-5)

Compound 5 (38 mg, 0.11 mmol) was added to a stirred suspension of oil-free NaH (5 mg, 0.11 mmol) in DMF (5 mL). When evolution of hydrogen ceased, benzyl chloride (14 mg, 0.11 mmol) was added and the mixture was heated at 50° C. for 4 h. The reaction mixture was added to water (5 mL), extracted with portions of ethyl ether. The combined organic phase was dried over anhydrous MgSO$_4$ and concentrated under diminished pressure to afford a crude residue. Elution with 1:1 hexane/ethyl acetate gave 4-(benzyloxy)-3-heptyl-5-iodo-2,6-dimethylpyridine (19) as a light yellow oil: yield 38 mg (80%); silica gel TLC $R_f$ 0.7 (1:1 hexane/ethyl acetate); $^1$H NMR (CDCl$_3$) δ 0.61-0.89 (m, 3H), 1.26-1.31 (m, 10H), 2.504 (s, 3H), 2.62-2.65 (m, 2H) 2.75 (s, 3H), 4.95 (s, 2H), 7.38-7.43 (m, 4H) and 7.55-7.57 (m, 1H).

To a solution of sodium methoxide prepared from sodium (5.0 mg, 0.23 mmol) and MeOH (1 mL) were added the iodo derivative 19 (27 mg, 0.06 mmol) and CuI (1.66 mg, 0.009 mmol). The reaction mixture was heated at 110° C. for 18 h and cooled, and 1 M aqueous NH4Cl was added. The mixture was extracted with portions of ethyl ether. The combined organic phase was dried over anhydrous MgSO$_4$ and concentrated under diminished pressure to afford a crude residue. Elution with ethyl acetate gave 4-(benzyloxy)-3-heptyl-5-methoxy-2,6-dimethylpyridine (20) as a light yellow oil: yield 19 mg (71%); silica gel TLC $R_f$ 0.3 (1:1 hexane/ethyl acetate); $^1$H NMR (CDCl$_3$) δ 0.60-0.89 (m, 3H), 1.26-1.30 (m, 10H), 2.48 (s, 3H), 2.60-2.62 (m, 2H) 2.74 (s, 3H), 3.70 (s, 3H). 4.95 (s, 2H), 7.38-7.42 (m, 4H) and 7.53-7.56 (m, 1H).

A solution of 20 (19 mg, 0.66 mmol) and mCPBA (125 mg, 0.72 mmol) in anhydrous CH$_2$Cl$_2$ (2 mL) was stirred at 0° C. for 1 hr under argon atmosphere, the solution was washed with aqueous NaHCO$_3$ dried over anhydrous MgSO$_4$ and concentrated under diminished pressure to afford a crude residue. The residue was dissolved in EtOH, Pd/C was added and after applying an H$_2$ atmosphere (1 bar), the solution was stirred at room temp for 30 min, After filtration through celite, which was thoroughly washed with EtOH, the filtrate was concentrated under diminished pressure and purified by chromatography on a silica gel column. Elution with 20:1 ethyl acetate/methanol gave 3-heptyl-1-hydroxy-5-methoxy-2,6-dimethylpyridin-4(1H)-one (CPD-5) as a light yellow oil; yield 9 mg (61%); silica gel TLC $R_f$ 0.25 (3:1 ethyl acetate/methanol); $^1$H NMR (CDCl$_3$) δ 0.84-0.89 (m, 3H), 1.24-1.35 (m, 10H), 2.45 (s, 3H), 2.50 (s, 3H) 2.63-2.67 (m, 2H) and 3.74 (s, 3H).

Example 6

Preparation of 3-heptyl-1-hydroxy-2,6-dimethylpyridin-4(1H)-one

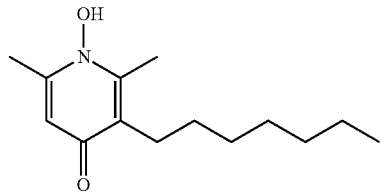 [SMILES: CCCCCCCc1c(C)n(O)c(C)cc1=O]

3-heptyl-1-hydroxy-2,6-dimethylpyridin-4(1H)-one (CPD-6)

A mixture of trimethyl pyrone 1 (113 mg, 0.51 mmol), hydroxylamine hydrochloride (707 mg, 10.2 mmol), sodium acetate (835 mg, 10.2 mmol), water (1 mL), and ethanol (2 mL) was heated to reflux for 8 hr. After the reaction mixture was cooled to room temperature, filtered, and the filtrate was concentrated under diminished pressure. The residue was purified by chromatography on a silica gel column. Elution with 5:1 ethyl acetate/methanol gave 3-heptyl-1-hydroxy-2,6-dimethylpyridin-4(1H)-one (CPD-6): yield 63 mg (51%); silica gel TLC $R_f$ 0.35 (3:1 ethyl acetate/methanol); $^1$H NMR (400 MHz, CDCl3) δ 0.84-0.88 (m, 3H), 1.24-1.45 (m, 10H), 2.36 (s, 3H), 2.47 (s, 3H), 2.60 (t, 2H, J=7.6 Hz) and 6.73 (s, 1H).

Example 7

Preparation of 3-decyl-1-hydroxy-2,6-dimethylpyridin-4(1H)-one

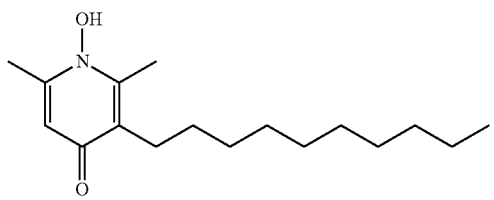 [SMILES: CCCCCCCCCCc1c(C)n(O)c(C)cc1=O]

3-decyl-1-hydroxy-2,6-dimethylpyridin-4(1H)-one (CPD-7)

To a mixture of 49 g of polyphosphoric acid and 30 mL of acetic acid was added 0.6 mL (0.5 g, 2.53 mmol) of 2-tridecanone. The resulting solution was heated at 130° C. with vigorous stirring for 8 h. The resulting dark black solution was cooled to 0° C. and 100 mL of water was added. The mixture was extracted with portions of ethyl ether. The combined organic phase was washed with 10% aqueous KOH, dried over anhydrous $MgSO_4$ and concentrated under diminished pressure to afford a crude residue. The residue was purified by chromatography on a silica gel column. Elution with chloroform gave 3-decyl-2,6-dimethyl-4H-pyran-4-one (21) as a light yellow solid: yield 331 mg (50%); silica gel TLC $R_f$ 0.52 (1:1 hexane/ethyl acetate); $^1$H NMR ($CDCl_3$, 400 MHz) δ 0.52-0.55 (m, 3H), 0.92-0.96 (m, 10H), 1.87 (s, 3H), 1.94 (s, 3H), 2.03 (t, 2H, J=7.2 Hz) and 5.73 (s, 1H); $^{13C}$ NMR ($CDCl_3$) δ 13.7, 16.9, 19.2, 22.3, 23.9, 28.2, 28.9, 29.1, 29.2, 29.3, 31.6, 112.3, 124.3, 161.2, 164.1, and 178.9.

A mixture of 21 (200 mg, 0.75 mmol), hydroxylamine hydrochloride (1.05 g, 15.2 mmol), sodium acetate (1.24 g, 15.2 mmol), water (1 mL), and ethanol (2 mL) was heated at reflux for 3 days. After the reaction mixture was cooled to room temperature, the crude was concentrated under diminished pressure to afford a yellow oil. The residue was purified by chromatography on a silica gel column. Elution with 5:1 chloroform/methanol gave 3-decyl-1-hydroxy-2,6-dimethylpyridin-4(1H)-one (CPD-7) as a light yellow oil: yield 0.08 g (40%); silica gel TLC $R_f$ 0.4 (3:1 ethyl acetate/methanol); $^1$H NMR ($CDCl_3$, 400 MHz) δ 0.84-0.88 (m, 3H), 1.24-1.44 (m, 16H), 2.27 (s, 3H), 2.48 (s, 3H), 2.57-2.61 (m, 2H) and 6.65 (s, 1H).

Example 8

Preparation of 3-hexadecyl-1-hydroxy-2,6-dimethylpyridin-4(1H)-one

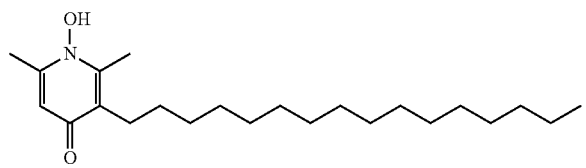 [SMILES: CCCCCCCCCCCCCCCCc1c(C)n(O)c(C)cc1=O]

3-hexadecyl-1-hydroxy-2,6-dimethylpyridin-4(1H)-one (CPD-8)

A mixture of 2 (200 mg, 0.57 mmol), hydroxylamine hydrochloride (399 mg, 5.7 mmol), sodium acetate (471 mg, 5.7 mmol), water (1 mL), and ethanol (2 mL) was heated at reflux for 3 days. After the reaction mixture was cooled to room temperature, the crude product was concentrated under diminished pressure to a yellow oil. The residue was purified by chromatography on a silica gel column. Elution with 5:1 chloroform/methanol gave 3-hexadecyl-1-hydroxy-2,6-dimethylpyridin-4(1H)-one (CPD-8) as a white solid: yield 0.088 g (42%); silica gel TLC $R_f$ 0.5 (3:1 ethyl acetate/methanol); $^1$H NMR ($CDCl_3$, 400 MHz) δ 0.83-0.85 (m, 3H), 1.22-1.27 (m, 28H), 2.32 (s, 3H), 2.46 (s, 3H), 2.55 (t, 2H, J=8 Hz) and 6.7 (s, 1H).

Example 9

Preparation of 3-bromo-5-heptyl-1-hydroxy-2,6-dimethylpyridin-4(1H)-one

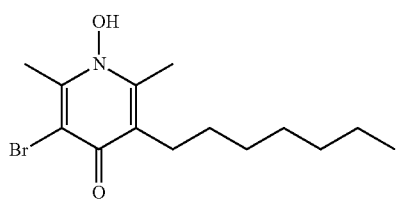

3-bromo-5-heptyl-1-hydroxy-2,6-dimethylpyridin-4 (1H)-one (CPD-9)

To a stirred solution of CPD-6 (63 mg, 0.266 mmol) in acetic acid (2 M) was added dropwise a solution of bromine (0.04 mL, 0.266 mmol) in acetic acid (1 mL) at 10-15° C. After 1.5 h a few drops of a saturated aqueous sodium sulfite solution was added to discharge excess bromine. The reaction mixture was diluted with water and extracted with portions of ethyl ether. The combined organic phase was dried over anhydrous $MgSO_4$ and concentrated under diminished pressure to afford a crude residue. The residue was purified by chromatography on a silica gel column to afford compound 3-bromo-5-heptyl-1-hydroxy-2,6-dimethylpyridin-4(1H)-one (CPD-9): yield 57 mg (69%); silica gel TLC $R_f$ 0.68 (5:1 ethyl acetate/methanol); $^1$H NMR ($CDCl_3$) δ 0.82-0.86 (m, 3H), 1.23-1.36 (m, 10H), 2.42 (s, 3H), 2.51-2.54 (m, 5H).

Example 10

Preparation of 3-bromo-5-decyl-1-hydroxy-2,6-dimethylpyridin-4(1H)-one

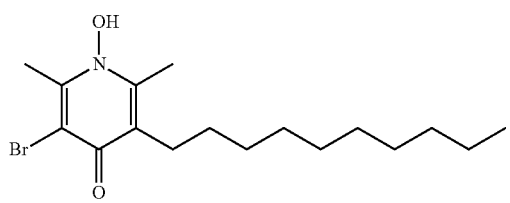

3-bromo-5-decyl-1-hydroxy-2,6-dimethylpyridin-4 (1H)-one (CPD-10)

To a stirred solution of CPD-7 (40 mg, 0.143 mmol) in acetic acid (2 M) was added dropwise a solution of bromine (0.02 mL, 0.143 mmol) in acetic acid (1 mL) at 10-15° C. After 1.5 h a few drops of a saturated aqueous sodium sulfite solution was added to discharge excess bromine. The reaction mixture was diluted with water and extracted with portions of ethyl ether. The combined organic phase was dried over anhydrous $MgSO_4$ and concentrated under diminished pressure to afford a crude residue. The residue was purified by chromatography on a silica gel column to afford compound 3-bromo-5-decyl-1-hydroxy-2,6-dimethylpyridin-4(1H)-one (CPD-10): yield 37 mg (73%); silica gel TLC $R_f$ 0.75 (5:1 ethyl acetate/methanol); $^1$H NMR ($CDCl_3$, 400 MHz) δ 0.84-0.88 (m, 3H), 1.24-1.44 (m, 16H), 2.36 (s, 3H) and 2.51-2.54 (m, 5H).

Example 11

Preparation of 3-bromo-5-hexadecyl-1-hydroxy-2,6-dimethylpyridin-4(1H)-one

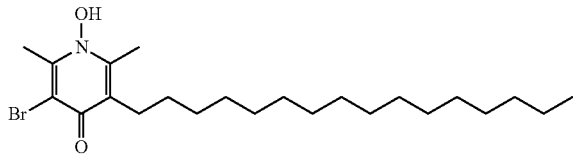 [SMILES: CCCCCCCCCCCCCCCCc1c(C)n(O)c(C)c(Br)c1=O]

3-bromo-5-hexadecyl-1-hydroxy-2,6-dimethylpyridin-4(1H)-one (CPD-11)

To a stirred solution of CPD-8 (44 mg, 0.12 mmol) in acetic acid (2 M) was added dropwise a solution of bromine (0.006 mL, 0.12 mmol) in acetic acid (1 mL) at 10-15° C. After 1.5 h a few drops of a saturated aqueous sodium sulfite solution was added to discharge excess bromine. The reaction mixture was diluted with water and extracted with portions of ethyl ether. The combined organic phase was dried over anhydrous $MgSO_4$ and concentrated under diminished pressure to afford a crude residue. The residue was purified by chromatography on a silica gel column to afford compound 3-bromo-5-hexadecyl-1-hydroxy-2,6-dimethylpyridin-4(1H)-one (CPD-11): yield 37 mg (69%); silica gel TLC $R_f$ 0.80 (5:1 ethyl acetate/methanol); $^1$H NMR ($CDCl_3$, 400 MHz) δ 0.81-0.84 (m, 3H), 1.21-1.29 (m, 28H), 2.37 (s, 3H) and 2.47-2.50 (m, 5H).

Example 12

Preparation of 3-chloro-5-heptyl-1-hydroxy-2,6-dimethylpyridin-4(1H)-one

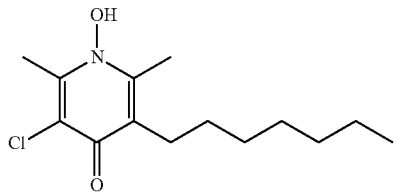 [SMILES: CCCCCCCc1c(C)n(O)c(C)c(Cl)c1=O]

3-chloro-5-heptyl-1-hydroxy-2,6-dimethylpyridin-4(1H)-one (CPD-12)

To a stirred solution of CPD-6 (11 mg, 0.046 mmol) in acetic acid (10 mL) was added N-chlorosuccinimide (6.7 g, 0.05 mmol). The mixture was heated at 100° C. for 8 hr and cooled to room temperature. The reaction mixture was diluted with water and extracted with portions of ethyl ether. The combined organic phase was dried over anhydrous $MgSO_4$ and concentrated under diminished pressure to afford a crude residue. The residue was purified by chromatography on a silica gel column to afford compound 3-chloro-5-heptyl-1-hydroxy-2,6-dimethylpyridin-4(1H)-one (CPD-12): yield 7 mg (54%); silica gel TLC $R_f$ 0.66 (5:1 ethyl acetate/methanol); $^1$H NMR (400 MHz, $CDCl_3$) δ 0.77-0.81 (m, 3H), 1.18-1.26 (m, 10H), 2.28 (s, 3H), 2.35 (s, 3H) and 2.44-2.47 (m, 2H).

Example 13

Preparation of 3-chloro-5-decyl-1-hydroxy-2,6-dimethylpyridin-4(1H)-one

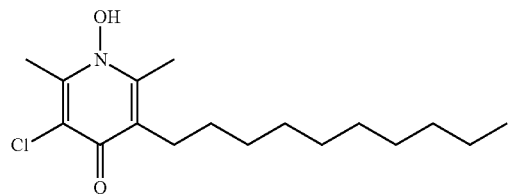 [SMILES: CCCCCCCCCCc1c(C)n(O)c(C)c(Cl)c1=O]

3-chloro-5-decyl-1-hydroxy-2,6-dimethylpyridin-4(1H)-one (CPD-13)

To a stirred solution of CPD-7 (40 mg, 0.143 mmol) in acetic acid (10 mL) was added N-chlorosuccinimide (19 mg, 0.143 mmol). The reaction mixture was heated at 100° C. for 8 hr and cooled to room temperature. The reaction mixture was diluted with water and extracted with portions of ethyl ether. The combined organic phase was dried over anhydrous $MgSO_4$ and concentrated under diminished pressure to afford a crude residue. The residue was purified by chromatography on a silica gel column to afford compound 3-chloro-5-decyl-1-hydroxy-2,6-dimethylpyridin-4(1H)-one (CPD-13): yield 30 mg (67%); silica gel TLC $R_f$ 0.7 (7:1 ethyl acetate/methanol); $^1$H NMR (400 MHz, $CDCl_3$) δ 0.73-0.78 (m, 3H), 1.15-1.20 (m, 16H), 2.25 (s, 3H), 2.30 (s, 3H) and 2.37-2.40 (m, 2H).

Example 14

Preparation of 3,7-bis(didecylamino)phenothiazin-5-ium bromide

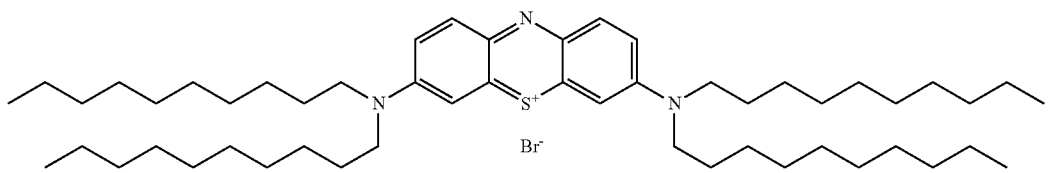 [SMILES: CCCCCCCCCCN(CCCCCCCCCC)c1ccc2nc3ccc(N(CCCCCCCCCC)CCCCCCCCCC)cc3[s+]c2c1 ; [Br-]]

3,7-bis(didecylamino)phenothiazin-5-ium bromide (CPD-14)

To a solution of 1.0 g (5.03 mmol) of phenothiazine in 60 mL of glacial acetic acid was added a solution 16.08 g (100.6 mmol) of bromine in 40 mL of glacial acetic acid with vigorous stirring. After stirring for three minutes, 400 mL of water was added to the reaction mixture. The resulting red precipitate was filtered, washed with diethyl ether and dried under vacuum to give 3,7-dibromophenothiazin-5-ium bromide (22): yield 2.19 g (100%); mp 90° C. (dec.).

To a solution of 1.7 g (5.72 mmol) of didecylamine in 20 mL of $CHCl_3$ was added 0.63 g (1.43 mmol) of 22. The reaction mixture was stirred at room temperature for 2 h under argon and concentrated under diminished pressure to give 3,7-bis(didecylamino)phenothiazin-5-ium bromide (CPD-14): mass spectrum (MALDI-TOF), m/z 788.69 ($M^+$).

Example 15

Preparation of 3,7-bis(dipentylamino)phenothiazin-5-ium bromide

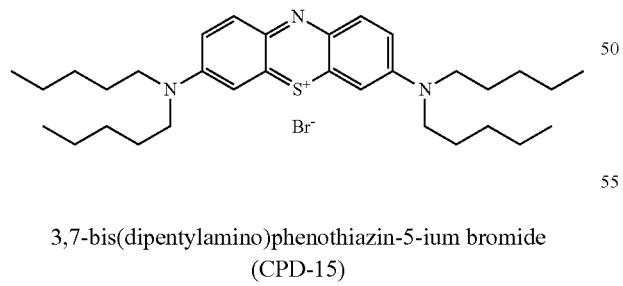

3,7-bis(dipentylamino)phenothiazin-5-ium bromide (CPD-15)

To a solution of 3.2 g (20.1 mmol) of dipentylamine in 60 mL of $CHCl_3$ was added 4.37 g (10.03 mmol) of 22. The reaction mixture was stirred at r.t for 2 h under argon and concentrated under reduced pressure to give 3,7-bis(dipentylamino)phenothiazin-5-ium bromide (CPD-15): mass spectrum (MALDI-TOF), m/z 509.38 $(M+H)^+$.

Example 16

Preparation of 7-(didecylamino)-3H-phenothiazine-3-one

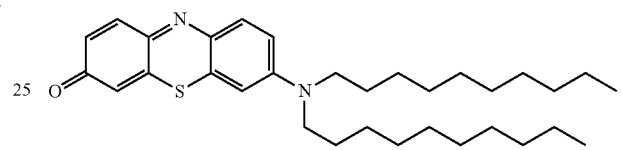

7-(didecylamino)-3H-phenothiazine-3-one (CPD-16)

To a solution of 0.13 g of CPD-14 in 5 mL of water and 5 mL of THF was added 0.034 g (0.2 mmol) of $AgNO_3$ dissolved in excess $NH_4OH$. The reaction mixture was heated to reflux for an hour, filtered and extracted with two 10-mL portions of EtOAc. The violet organic layer was washed with brine, dried over anhydrous $Na_2SO_4$, concentrated under diminished pressure. The dark solid was purified on a silica gel column (30×1.25 cm). Elution with 1:1 hexanes/EtOAc gave CPD-16 as a dark solid: yield 2 mg (2.5%); silica gel TLC $R_f$ 0.5 (1:1 hexanes/EtOAc); mass spectrum (MALDI-TOF), m/z 509.35 $(M+H)^+$.

Example 17

Preparation of 7-(dipentylamino)-3H-phenothiazin-3-one

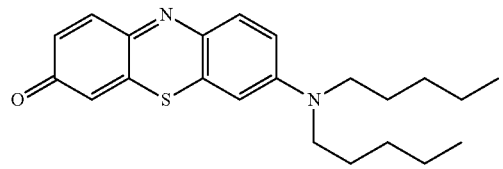 [SMILES: CCCCCN(CCCCC)c1ccc2nc3ccc(=O)cc-3sc2c1]

7-(dipentylamino)-3H-phenothiazin-3-one (CPD-17)

To a solution of 5.1 g of CPD-15 in 100 mL of water was added 1.9 g (11.2 mmol) of $AgNO_3$ dissolved in excess $NH_4OH$. The reaction mixture was refluxed for an hour, filtered and extracted with five 20-mL portions of EtOAc. The violet organic layer was washed with brine, dried over anhydrous Na₂SO₄, concentrated under diminished pressure. The dark solid was purified on a silica gel column (30×1.25 cm). Elution with EtOAc gave CPD-17 as a dark solid: yield 40 mg (<1%); silica gel TLC $R_f$ 0.57 (EtOAc); mass spectrum (MALDI-TOF), m/z 369.55 (M+H)⁺.

Example 18

Preparation of 7-(dimethylamino)-3H-phenothiazin-3-one

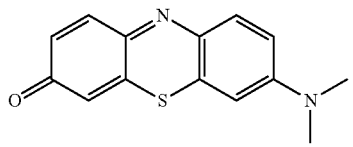 [SMILES: CN(C)c1ccc2nc3ccc(=O)cc-3sc2c1]

7-(dimethylamino)-3H-phenothiazin-3-one
(CPD-18)

To a solution of 0.5 g (1.56 mmol) of Methylene blue in 50 mL of water was added 0.53 g (3.12 mmol) of AgNO₃ dissolved in excess NH₄OH. The reaction mixture was heated to reflux for an hour, filtered and extracted with EtOAc (20×5 mL). The organic layer was washed with brine, dried over anhydrous Na₂SO₄, concentrated under diminished pressure. The dark solid was purified on a silica gel column. Elution with 9:1 EtOAc/MeOH gave CPD-18 as a dark solid: yield-25 mg (6%); silica gel TLC $R_f$ 0.27 (9:1 EtOAc/MeOH); ¹H NMR (CDCl₃) δ 3.16 (s, 1H), 6.60 (d, 1H, J 2.8 Hz), 6.69 (d, 1H, J 2.4 Hz), 6.83 (d, 1H, J 2 Hz), 6.86 (d, 1H, J 2.8 Hz), 7.67 (d, 1H, J 10 Hz), 7.71 (d, 1H, J 9.2 Hz); mass spectrum (MALDI-TOF), m/z 257.07 (M+H)⁺.

Example 19

Compounds of formula (I)

The following compounds may be prepared essentially according to the procedures set forth above, with modifications where necessary of the starting materials to provide the desired product:

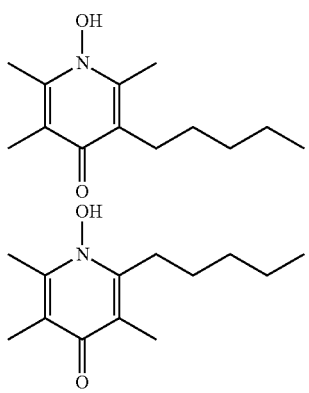

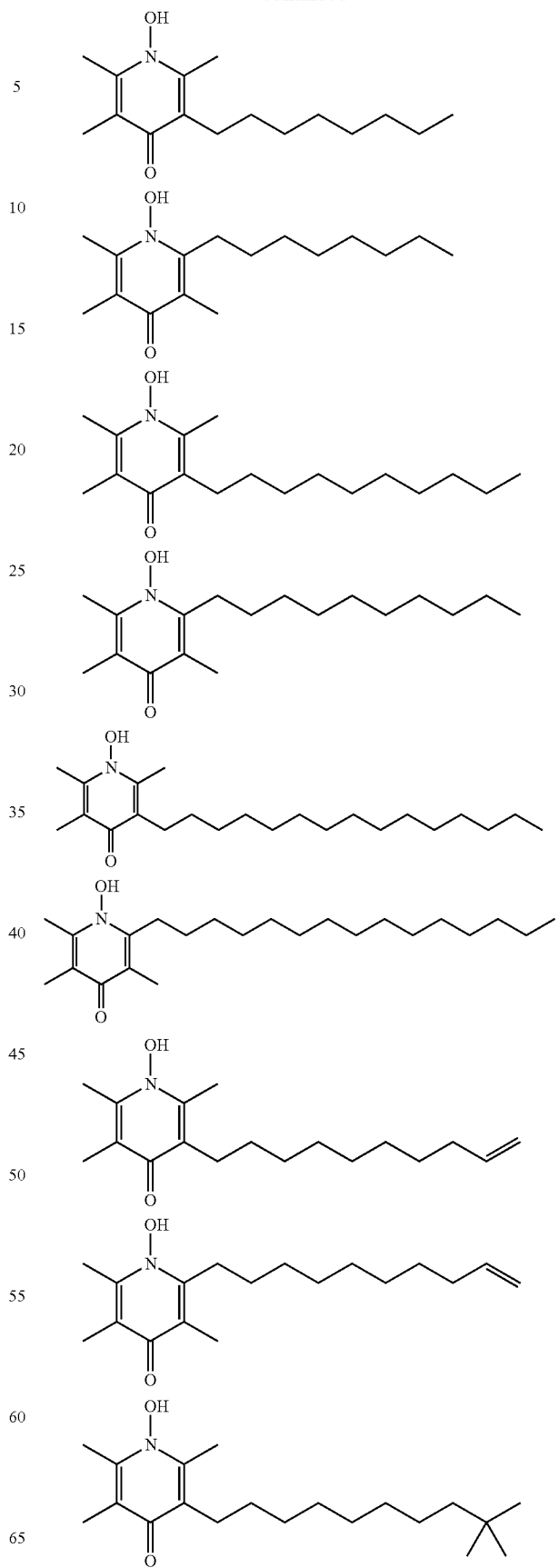

47
-continued
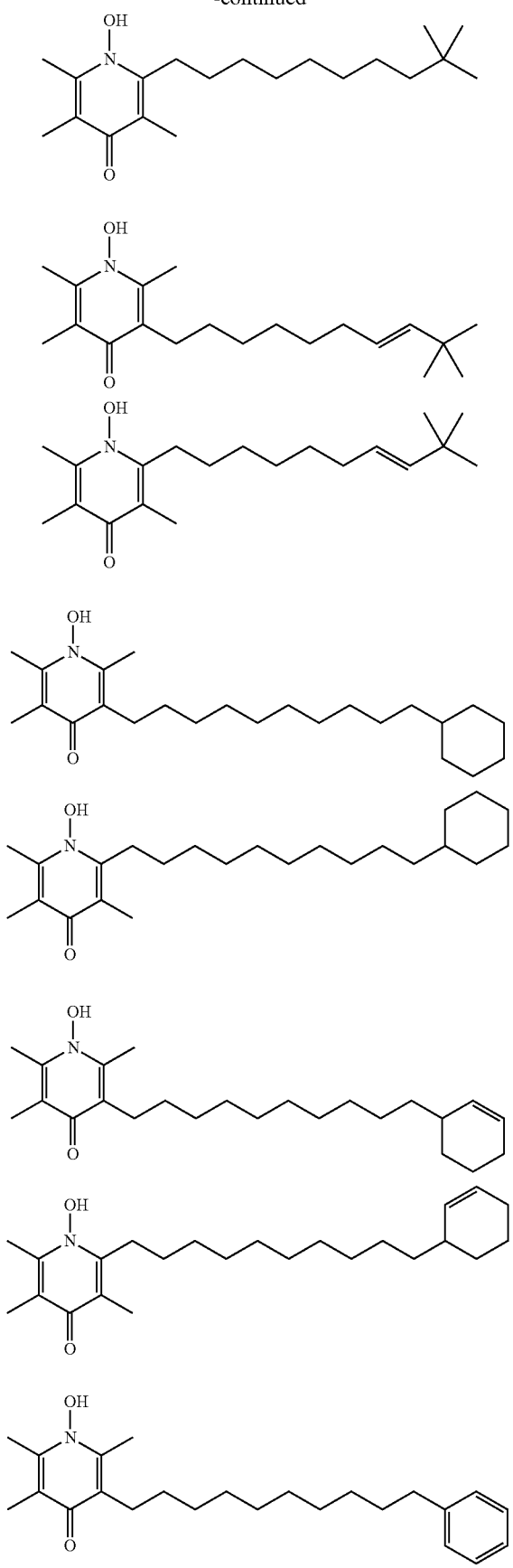
48
-continued
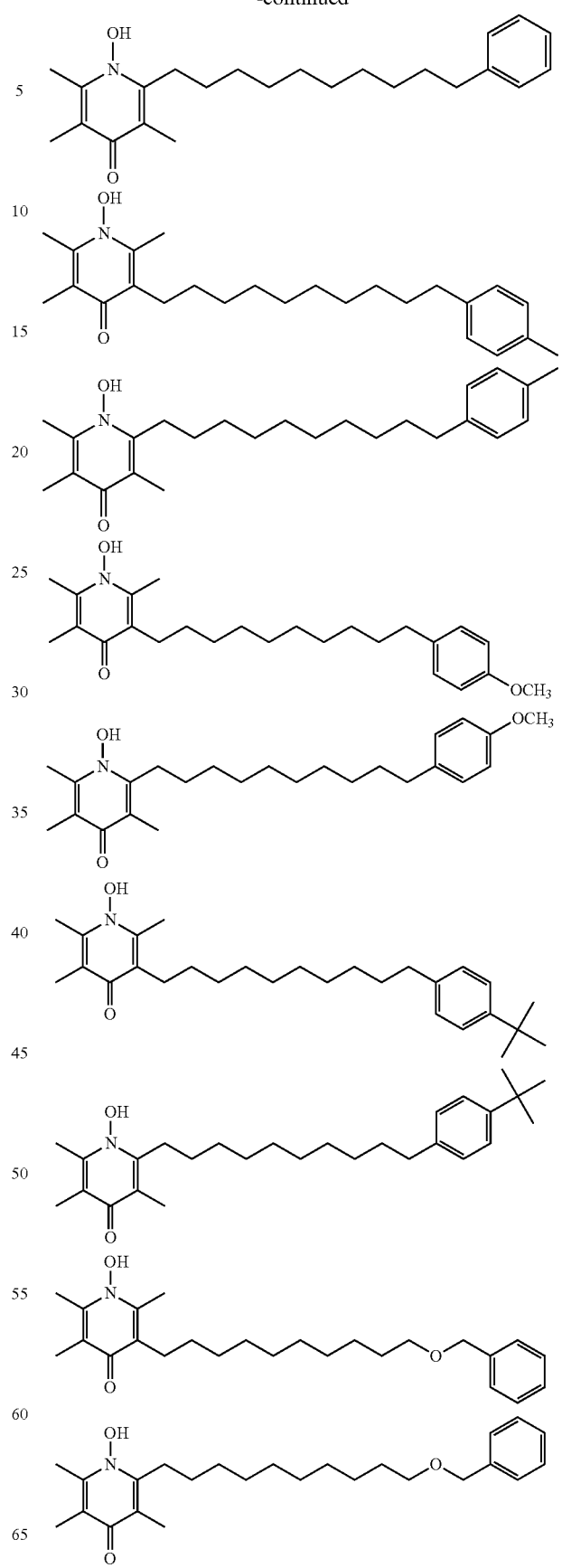

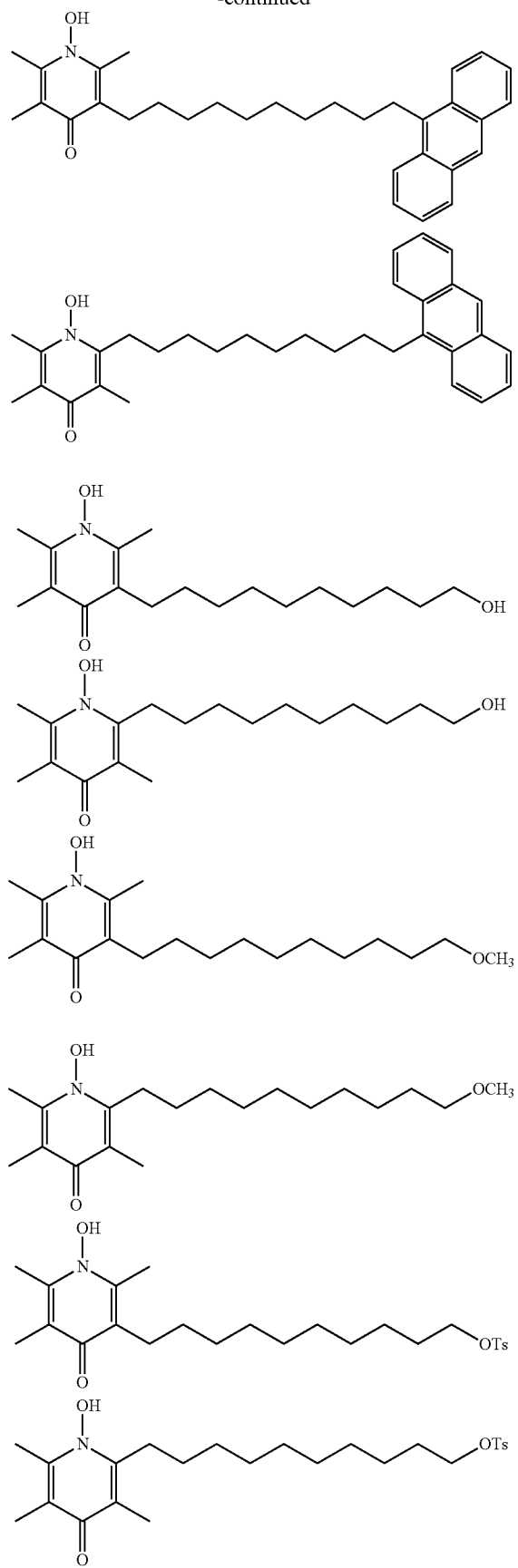
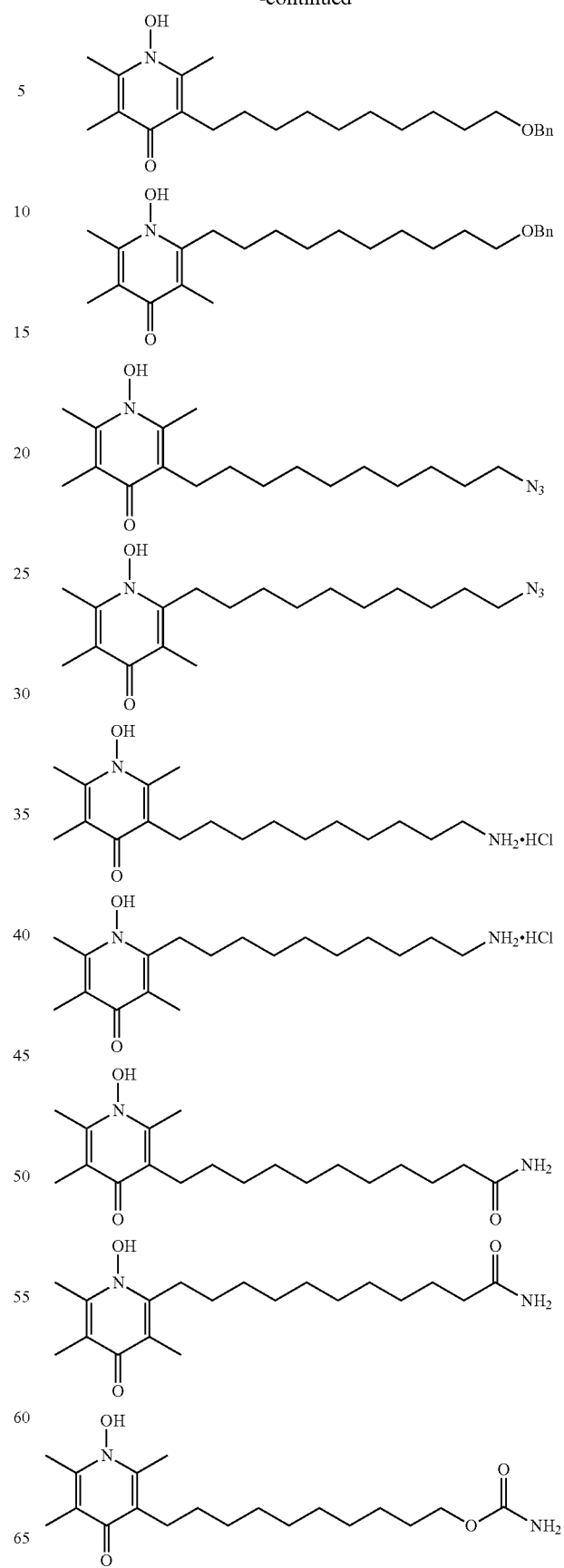

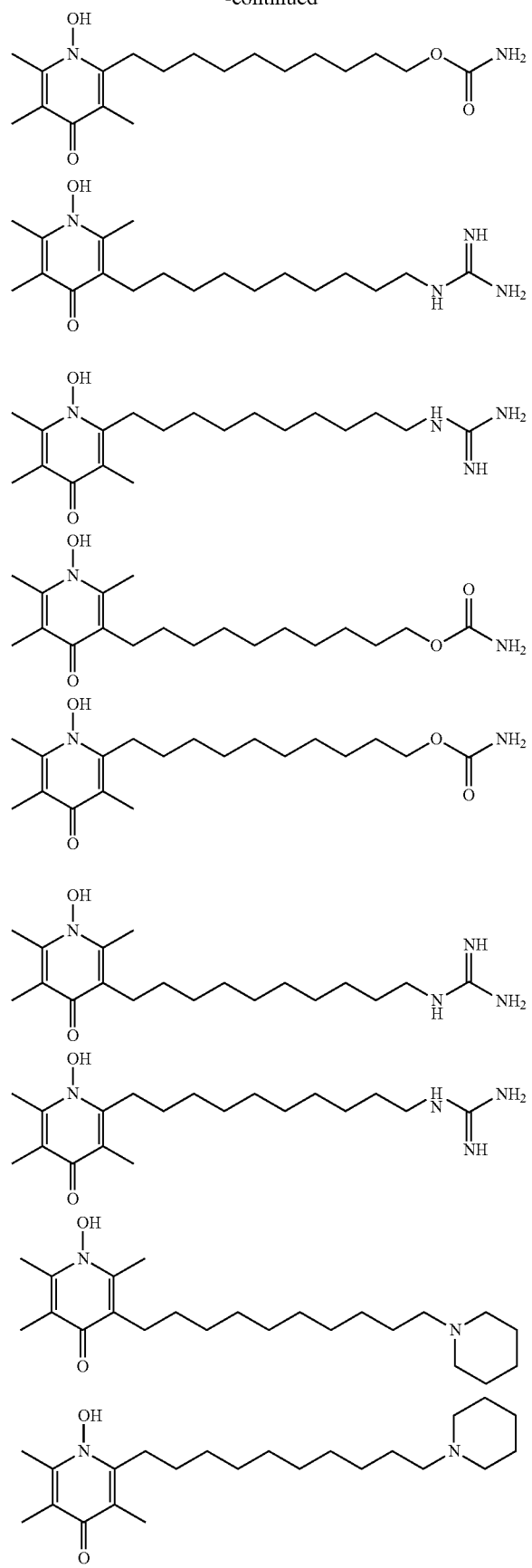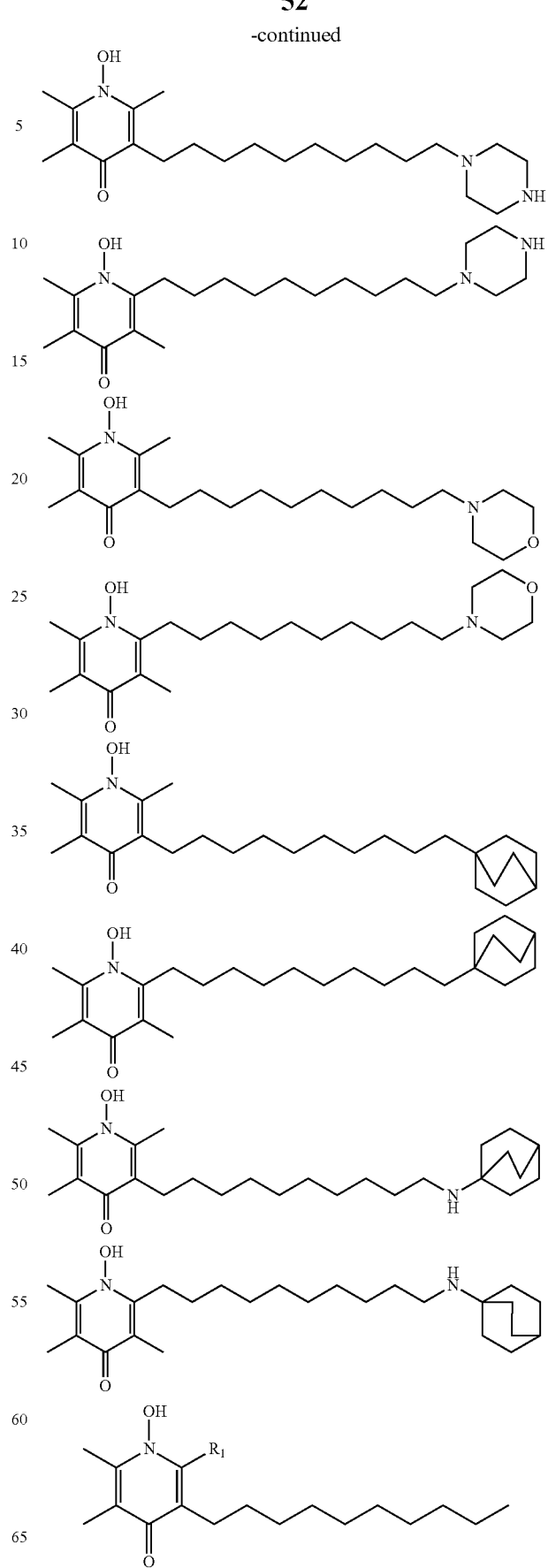

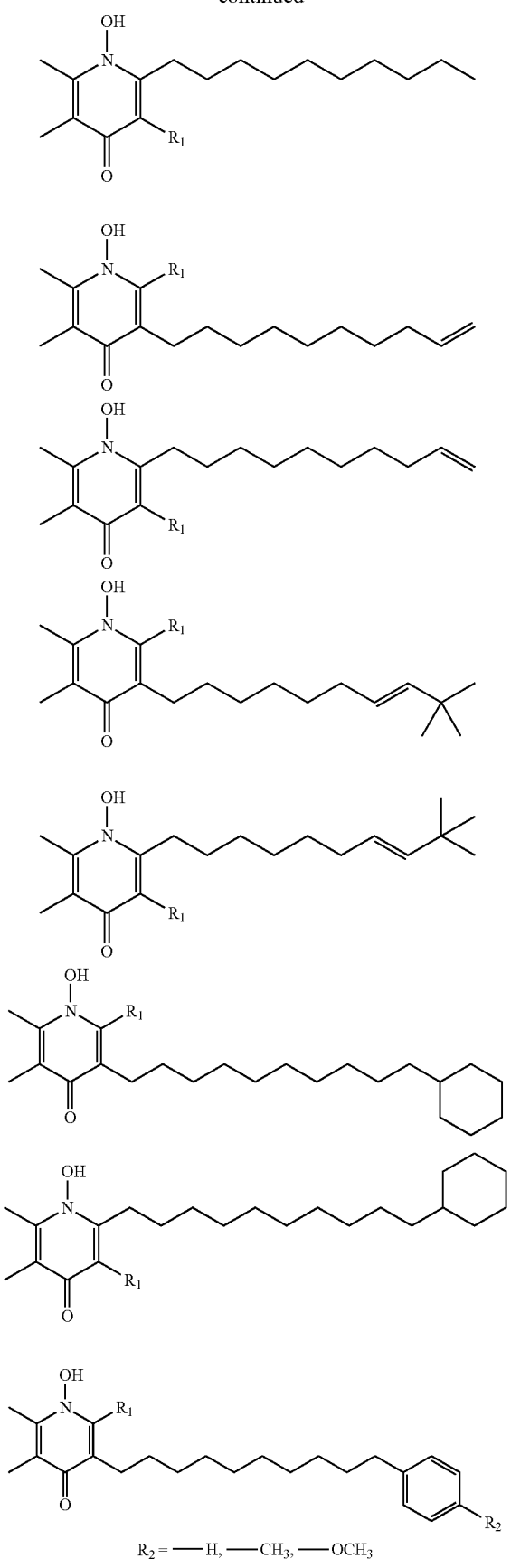
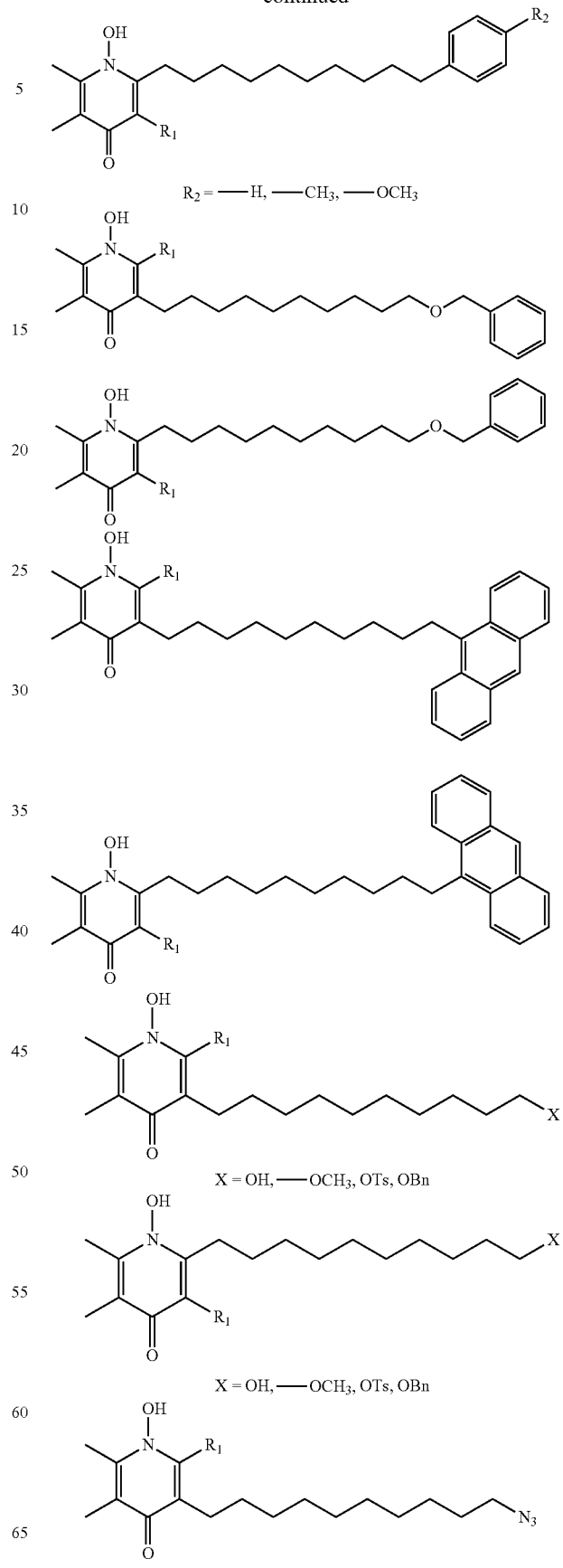

55
-continued
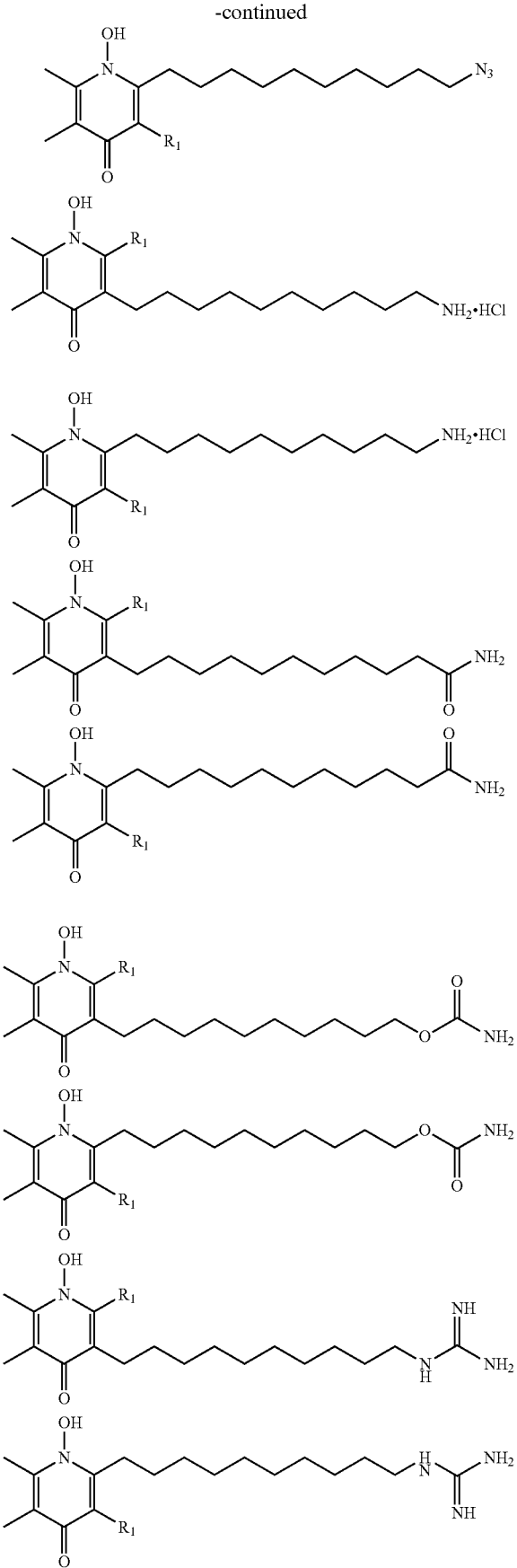
56
-continued
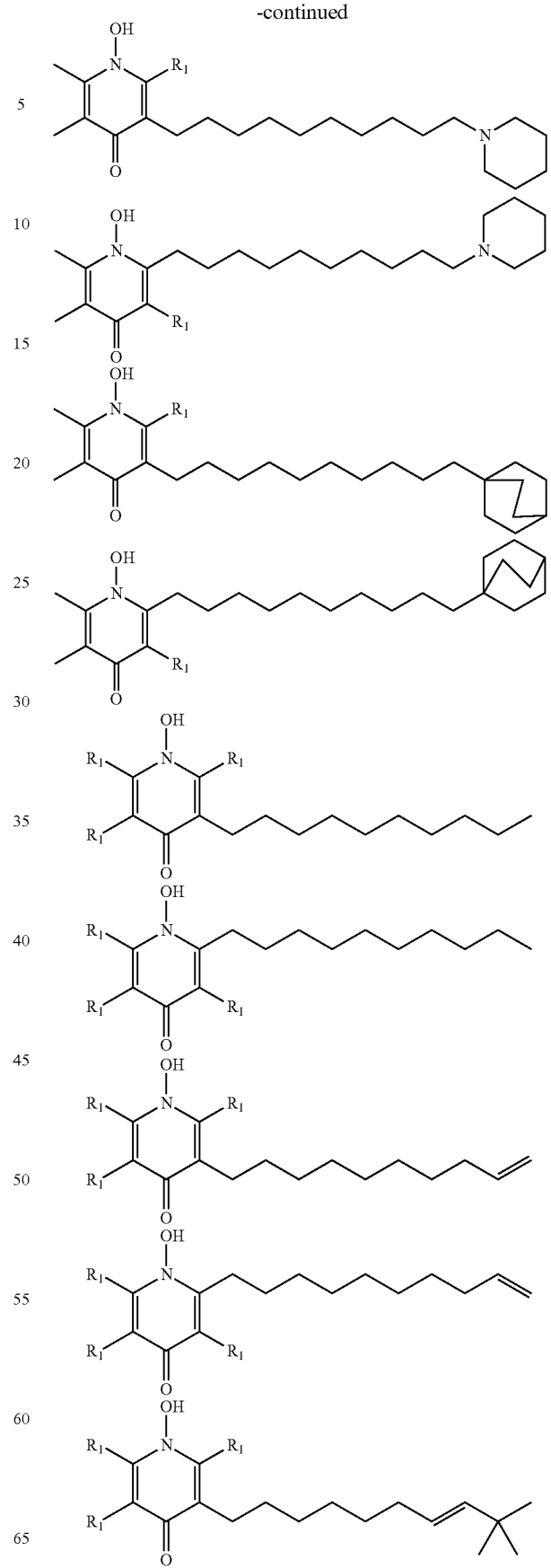

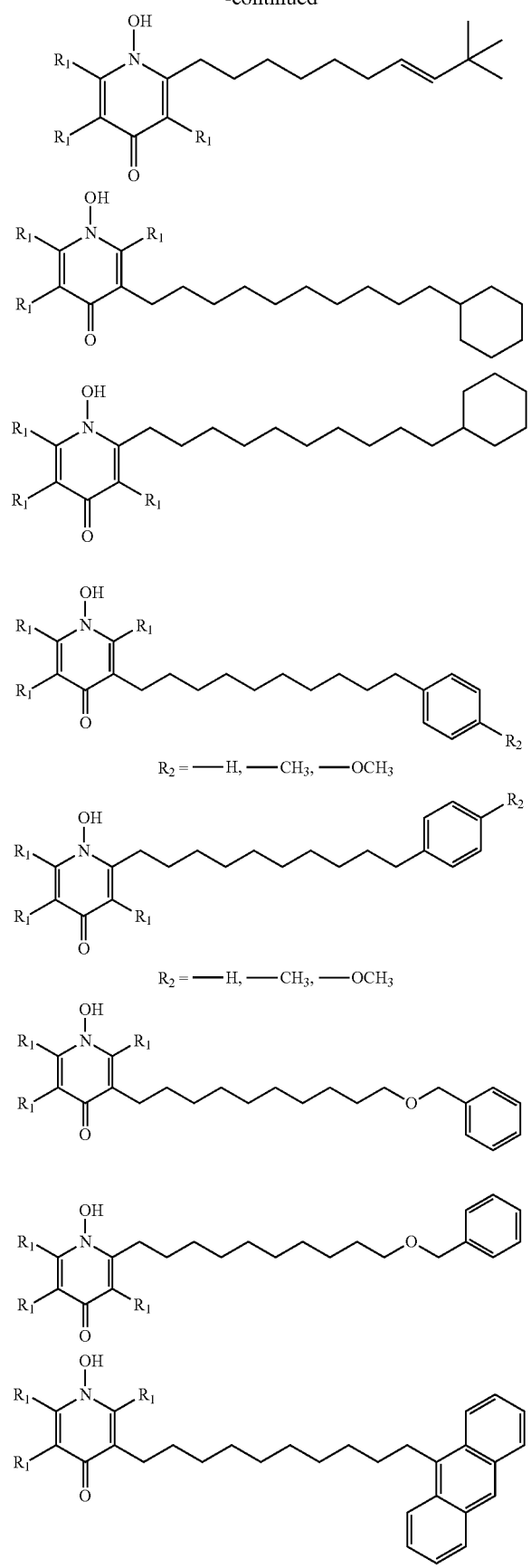
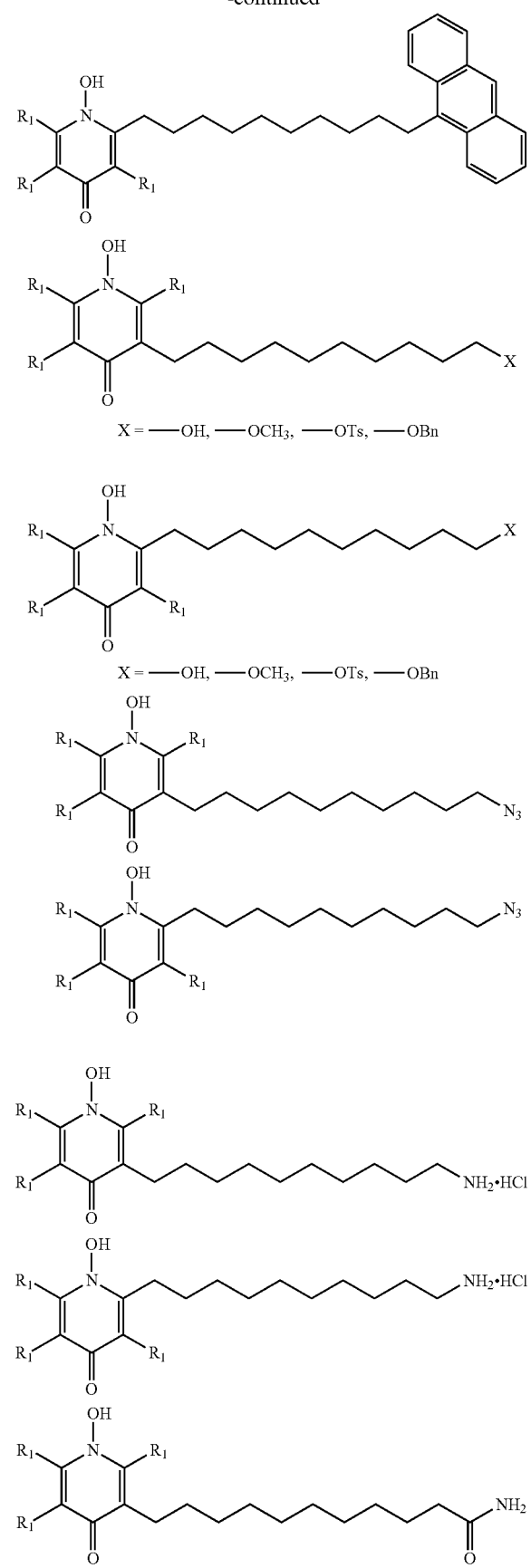

-continued
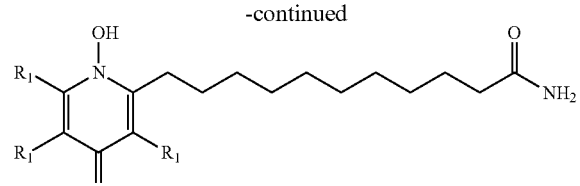
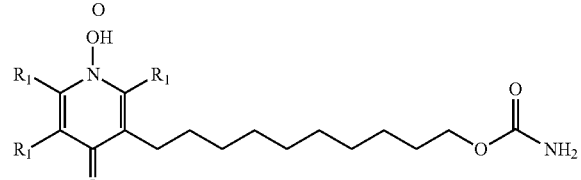
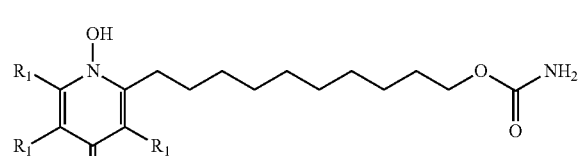
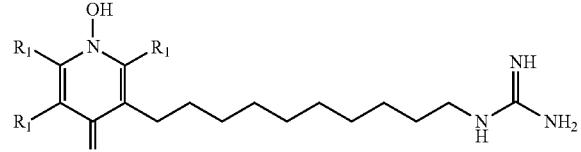
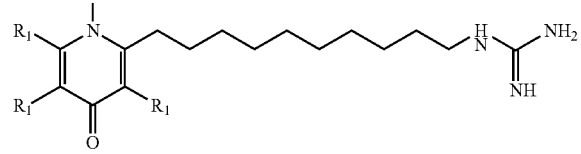
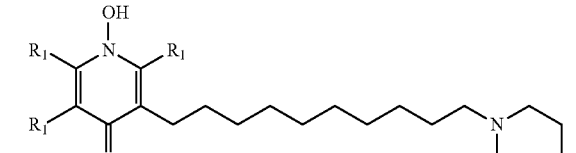
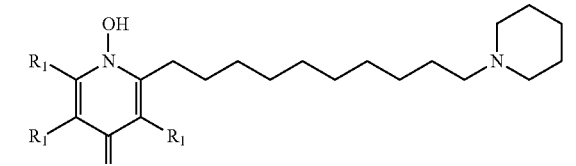
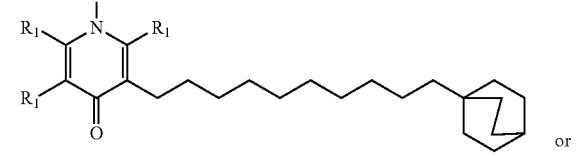
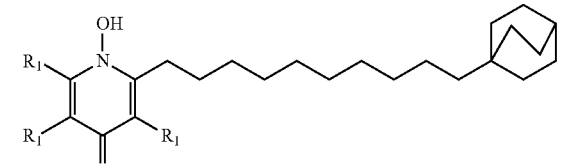
$R_1$ = —$OCH_3$, —$NHCH_3$, —$SCH_3$
Example 20
Compounds of Formula (II)
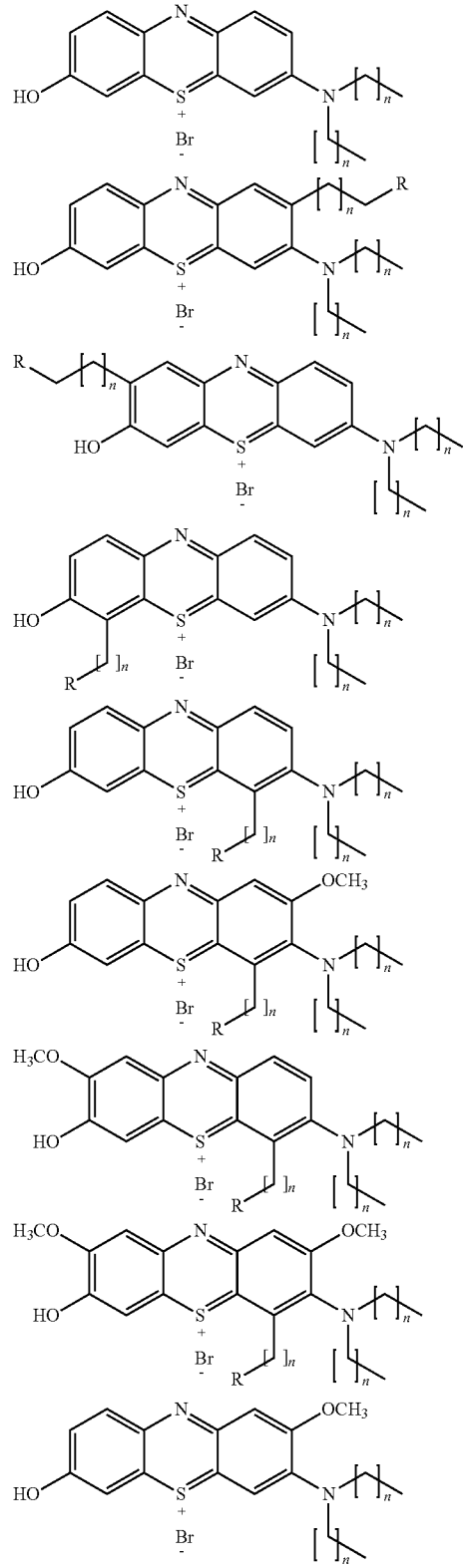

-continued

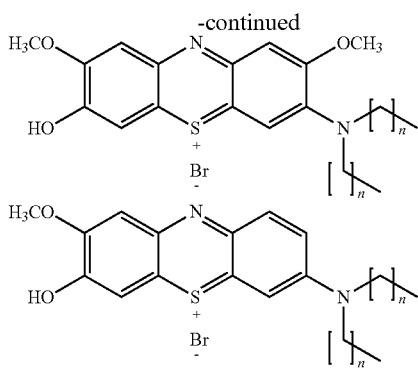

wherein:
n=0, 1, 2, 3, 4, 5, 6, 7, 8, 9, 10, 11, 12, 13, or 14; and

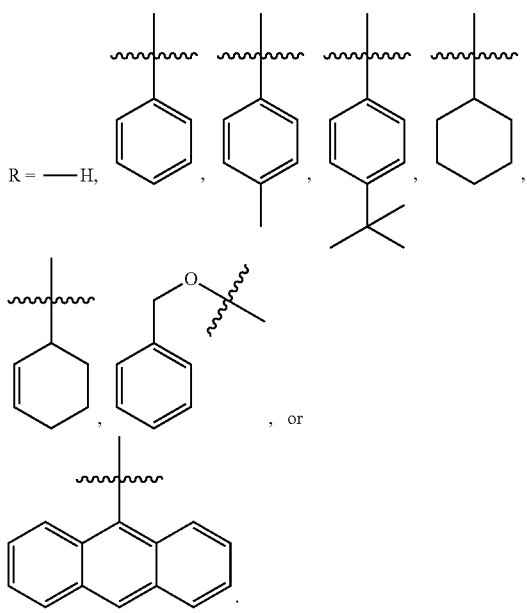

Example 21

Cell Culture

Leukemic CEM cells (ATCC®, catalogue number CRL-2264) were cultured in RPMI (GIBCO, Grand island, NY, USA) with 10% FBS (Fisher Scientific, TX, USA), 2 mM glutamine (HyClone, South Logan, Utah, USA) and 1% penicillin-streptomycin mix antibiotics (Cellgro, Manassas, Va., USA) supplements. Cells were maintained in the log phase at a concentration of between $1 \times 10^5$ and $1 \times 10^6$ cells/mL.

Friedreich's Ataxia lymphocytes and control cells (Coriell, catalogue number GM158150, and GM158151, respectively) were cultured in RPMI (GIBCO, Grand island, NY, USA) with 15% FBS (Fisher Scientific, TX, USA), 2 mM glutamine (HyClone, South Logan, Utah, USA) and 1% penicillin-streptomycin mix antibiotics (Cellgro, Manassas, Va., USA) supplements. Cells were maintained in the log phase at a concentration of between $1 \times 10^5$ and $1 \times 10^6$ cells/mL.

Friedreich's Ataxia fibroblasts, and control cells ((Coriell, catalog numbers GM04078 and GM08402, respectively). Fibroblasts were cultured in 64% (v/v) Eagle's Minimal Essential Medium (MEM), no phenol red with Eagle's balanced salt (EBS) and 25% M199 with EBS (GIBCO, Grand island, NY, USA) supplemented with 10% (v/v) Fetal Calf Serum (HyClone, South Logan, Utah, USA), 1% penicillin-streptomycin mix antibiotics (Cellgro, Manassas, Va., USA), 10 ng/mL insulin (Sigma, St. Louis, Mo., USA), 10 ng/mL basic fibroblast growth factor βFGF (Lonza, Walkersville, Md., USA) and 2 mM glutamine (HyClone, South Logan, Utah, USA).

$CoQ_{10}$ deficient lymphocyte and normal lymphocyte cell lines (Coriell Cell Repositories, catalog number GM-17932, GM-158151, respectively). $CoQ_{10}$ deficient lymphocytes were cultured under glucose-free media supplemented with galactose for two weeks to force energy production predominantly through oxidative phosphorylation rather than glycolysis (Quinzii et al.; Robinson B H, Petrova-Benedict R, Buncic J R, Wallace D C. Nonviability of cells with oxidative defects in galactose medium: A screening test for affected patient fibroblast. Biochem. Med. Metab. Biol. 1992; 48:122-126). Lymphocytes were cultured in RPMI 1640 medium glucose-free (Gibco, Grand Island, N.Y.) supplemented with 25 mM galactose, 2 mM glutamine and 1% penicillin-streptomycin (Cellgro), and 10%, dialyzed fetal bovine serum FBS (<0.5 µg/mL) (GEMINI, Bio-Product).

Leber's cells (Coriell, catalogue number GM10744) were cultured in RPMI (GIBCO, Grand island, NY, USA) with 15% FBS (Fisher Scientific, TX, USA), 2 mM glutamine (HyClone, South Logan, Utah, USA) and 1% penicillin-streptomycin mix antibiotics (Cellgro, Manassas, Va., USA) supplements. Cells were maintained in the log phase at a concentration of between $1 \times 10^5$ and $1 \times 10^6$ cells/mL.

Alzheimer's fibroblasts (Coriell, catalogue number AG06848) were cultured in Eagle's Minimum Essential Medium with Earle's salts (GIBCO, Grand island, NY, USA) and non-essential amino acids (Invitrogen, N.Y., USA) with 15% FBS (Fisher Scientific, TX, USA), 2 mM glutamine (HyClone, South Logan, Utah, USA) and 1% penicillin-streptomycin mix antibiotics (Cellgro, Manassas, Va., USA) supplements. Cells were cultured in 75 ml flaks and were maintained at confluency.

Alzheimer's lymphoblasts (Coriell, catalogue number AG06849) were cultured in RPMI (GIBCO, Grand island, NY, USA) with 15% FBS (Fisher Scientific, TX, USA), 2 mM glutamine (HyClone, South Logan, Utah, USA) and 1% penicillin-streptomycin mix antibiotics (Cellgro, Manassas, Va., USA) supplements. Cells were maintained in the log phase at a concentration of between $1 \times 10^5$ and $1 \times 10^6$ cells/mL.

Leigh syndrome cells (Coriell, catalogue number GM13740) were cultured in RPMI (GIBCO, Grand island, NY, USA) with 15% FBS (Fisher Scientific, TX, USA), 2 mM glutamine (HyClone, South Logan, Utah, USA) and 1% penicillin-streptomycin mix antibiotics (Cellgro, Manassas, Va., USA) supplements. Cells were maintained in the log phase at a concentration of between $1 \times 10^5$ and $1 \times 10^6$ cells/mL.

I. Lipid Peroxidation Assay

Cis-Parinaric Acid Oxidation to Measure Lipid Peroxidation Several methods for assaying lipid peroxidation in vitro have been developed (Kuypers et al. (1987) *Biochim Biophys Acta.* 25, 266-274; Pap et al. (1999) *FEBS Lett* 453, 278-282; Drummen et al. (2002) *Free Radic Biol Med.* 33, 473-490). Almost all of these methods are based on inhibition of free radical-induced oxidation reactions. A widely used fluorescence assay for lipid peroxidation uses lipid soluble cis-parinaric acid as a probe. cis-parinaric acid loses its fluorescence ($\lambda_{exc/em}$: 320/432 nm) upon interaction with peroxyl radicals and retains its fluorescence in the presence of radical quenchers. cis-parinaric acid is, however, air sensitive, photolabile and absorbs light in the UV region of the spectrum (at ~320 nm). However, this region of the spectrum is where most compounds have also been found to absorb and emit light. In practical terms, the results obtained using cis-parinaric as a probe for lipid peroxidationare confounded due to the overlapping of the compounds emission spectra with the cis-parinaric emission spectrum.

$C_{11}$-BODIPY$^{581/591}$ Oxidation to Measure Lipid Peroxidation

To overcome the problem of spectral overlap using cis-parinaric acid, a fluorescence assay for lipid peroxidation using a lipophilic probe belonging to the BODIPY class of fluorescent dyes was used. $C_{11}$-BODIPY$^{581/591}$ (4,4-difluoro-5(4-phenyl-1,3-butadienyl)-4-bora-3a, 4a-diaza-s-indacene-3-propionic acid) fluorescence shifts from red to green upon oxidation. $C_{11}$-BODIPY$^{581/591}$ (Molecular Probes, Eugene, Oreg., USA) stock solution concentrations were determined by measuring the absorption of $C_{11}$-BODIPY$^{581/591}$ at 582 nm using a molar extinction coefficient of 140,000 mol$^{-1}$ cm$^{-1}$ (R. P. Haugland, (1999) Handbook of Fluorescent Probes and Research Chemicals, Molecular Probes, Inc., Eugene, Oreg.). The lipid peroxidation inducer 2,2'-Azobis(2-amidino-propane dihydrochloride) (AAPH) and the antioxidant compound α-tocopherol were obtained from Sigma (St. Louis, Mo., USA). Phospholipid bilayers were prepared from 1-stearoyl-2-oleoyl-phosphatidylcholine (SOPC) and 1,2-dilinoleoyl-phosphatidylcholine (DLPC) and were purchased from Avanti® polar lipids, INC (Alabaster, Ala., USA).

Preparation of Liposomes

Phosphotidylcholine (PC) liposomes were prepared as described before (Guey-Shuang et al. (1982) *Lipids*. 17, 403-413). Briefly, DLPC (25 mg) and SOPC (25 mg) were dissolved in chloroform and the solvent was removed by nitrogen evaporation (~2 hours to give a thin film of PC in a round bottom flask. The lipid film was hydrated with 50 mL of 10 mM Tris-HCl (pH 7.4), 100 mM KCl, shaken and sonicated for 15 seconds. The liposomes obtained were filtered several times through 0.2 μM membrane filter.

Measurement of $C_{11}$-BODIPY$^{581/591}$ Oxidation $C_{11}$ BODIPY$^{581/591}$ was incorporated into liposomes and oxidized by peroxyl radicals derived from the decomposition of AAPH in presence and absence of the compounds. Liposomes (1 mg/mL), suspended in 10 mM Tris-HCl (pH 7.4), 100 mM KCl, were transferred to a quartz 1 mL cuvette and placed in a Varian Cary Eclipse fluorometer (Varian, Cary, N.C.) equipped with a thermostatted cuvette holder at 40° C. Liposomes were pre-incubated for 10 min with 200 nM $C_{11}$ BODIPY$^{581/591}$ to allow their incorporation into the lipid phase of the liposomes. After the addition of AAPH (10 mM) the decay of red fluorescence was followed at $\lambda_{exc}$=570 nm, $\lambda_{em}$=600 nm. Relative fluorescence units were normalized to 100% intensity. Results obtained were verified by repeating experiments N=3 independent experiments.

Measurement of $C_{11}$-BODIPY$^{581/591}$ Oxidation in Cell Culture

Lipid peroxidation in cells was detected by utilizing the oxidant-sensitive lipophilic probe $C_{11}$ BODIPY$^{581/591}$. Briefly, cells (5×10$^5$ cell/mL) were treated with the test compounds at final concentrations of 1 and 2.5 μM, and incubated at 37° C. for 4 or 24 h in a humidified atmosphere containing 5% $CO_2$ in air. Cells were treated with 500 nM $C_{11}$ BODIPY$^{581/591}$ in phenol red-free RPMI-1640 media and incubated at 37° C. in the dark for 30 minutes. The cells were washed twice with phosphate buffered saline and oxidative stress was induced with 5 mM DEM in phenol red-free RPMI-1640 media for 90 minutes. Treated cells were collected by centrifugation at 300×g for 3 minutes and then washed twice with phosphate buffered saline. Cells were re-suspended in 250 μL of phosphate buffered saline and were analyzed by FACS (FACS Calibur flow cytometer, Becton Dickinson) to monitor the change in intensity of the $C_{11}$ BODIPY$^{581/591}$ green (oxidized) fluorescence signal.

Assay for Thiobarbituric Acid Reactive Species (TBARS)

Lipid peroxidation by hydrogen peroxide in bovine heart mitochondrial membranes was determined by measuring the amount of thiobarbituric acid reactive substances released. Bovine heart mitochondria (1 mg protein) prepared as described by Smith (38) were added to 800 μL of 50 mM phosphate buffer, pH 8.0, and subjected to oxidative stress by the addition of 25 mM glucose and 1 U/mL glucose oxidase from *Aspergillus niger*. Samples were incubated with or without test compounds at 37° C. for 30 minutes. Two hundred μL each of 1% (w/v) thiobarbituric acid and 35% (v/v) perchloric acid, as well as 0.1% (w/v) butylated hydroxytoluene (from a 2% stock solution in DMSO) were added. Samples were heated at 100° C. for 15 minutes. One-mL aliquots of each sample were taken and diluted in 2 mL of water, then extracted once with 2 mL of n-butanol. Triplicate 500-μL aliquots were taken from the butanol phase and transferred to a quartz cuvette. TBARS were determined fluorometrically from the emission spectrum ($\lambda_{ex}$ 515 nm; $\lambda_{em}$ 550 nm) using a Varian fluorimeter. The malondialdehyde concentration was determined based on a standard curve created using serial dilutions of 10 mM 1,1,3,3-tetraethoxypropane hydrolyzed in 1% (v/v) $H_2SO_4$ at 4° C. overnight. The malondialdehyde concentration was expressed as nmoles manoldialdehyde per mg protein. Protein in aliquots of the homogenates was determined by the bicinchoninic acid method.

II. Reactive Oxygen Species (ROS) Assay

Cellular ROS production can be monitored using 2',7'-dichlorodihydrofluorescein diacetate (DCFH-DA) (LeBel et al. (1992) *Chem. Res. Toxicol.* 5, 227-231) (Molecular Probes, Eugene, Oreg., USA), a membrane permeable and oxidant-sensitive fluorescent dye. DCFH-DA is a non-fluorescent derivative of fluorescein that emits fluorescence after being oxidized by hydrogen peroxide and other ROS. The emitted fluorescence is directly proportional to the concentration of hydrogen peroxide. DCFH-DA is nonionic and nonpolar and is easily taken up by cells. Once inside the cell, DCFH-DA is hydrolyzed by cellular esterases to non-fluorescent DCFH which traps the dye in the cell. In the presence of ROS including hydrogen peroxide, DCFH is oxidized to the highly fluorescent compound dichlorofluorescein (DCF). The intracellular DCF fluorescence is used as an index of cellular ROS production.

Cellular oxidative stress was induced by pharmacological depletion of glutathione (GSH) using the chemical diethylmaleate (DEM). Cells (1×10$^6$ cell/mL) were plated (1 mL) in twelve well plate and treated with the invention compounds (final concentration 1, 2.5, 5 or 10 μM), and incubated for fifteen hours at 37° C., 5% $CO_2$. The compounds tested were prepared by first making stock solutions (1 mM) in dimethylsulfoxide (DMSO). Cells were treated with 5 mM DEM for 30 minutes and collected by centrifugation at 300×g for 3 min and then washed twice with Phosphate Buffer Saline (PBS) (Invitrogen, N.Y., USA). Cells were re-suspended in PBS buffer+10 mM glucose and incubated at 37° C. in the dark for 20 min with 10 μM DCFH-DA. Cells were collected by centrifugation at 300×g for 3 min and then washed twice with PBS buffer. The samples were analyzed immediately by flow cytometry (Becton-Dickinson FACS Caliber), (Cell Quest software, BD Biosciences) using 488 nm excitation laser and FL1-H channel 538 nm emission filter. In each analysis, 10,000 events were recorded after cell debris were electronically gated out. Results obtained were verified by running duplicates and repeating experiments N=3 independent experiments. Authentic hydrogen peroxide was used as a positive control.

III. Superoxide ($O_2^-$) Assay

Cellular Superoxide production can be monitored using Dihydroethidium (DHE), a fluorogenic probe that is highly selective for Superoxide among ROS (Bindokas V P, J Neurosci 16: 1324-1336, 1996) (Invitrogen, USA). The emitted fluorescence is directly proportional to the concentration of superoxide radical. It is cell-permeable and reacts with superoxide anion to form ethidium, which in turn intercalates in the deoxyribonucleic acid, thereby exhibiting a red fluorescence (Hwan H Y, Oncology Reports 21: 253-261, 2009). Cellular Superoxide generation was induced by pharmacological inhibition of the mitochondrial electron transport between cytochrome b and c, using Antimycin A (Alexander A. Biochim Biophys Acta 767:120-129, 1984) (Sigma-Aldrich).

Cells ($1 \times 10^6$ cell/mL) were plated (1 mL) in twenty four well plate and treated with the invention compounds (final concentration 1, 2.5, 5 or 10 μM), and incubated for fifteen hours at 37° C., 5% $CO_2$. The compounds tested were prepared by first making stock solutions (1 mM) in dimethylsulfoxide (DMSO). Cells were treated with 50 μM Antimycin A for two hours and then, with 60 μM DHE. The samples were analyzed immediately by flow cytometry (Becton-Dickinson FACS Caliber), (Cell Quest software, BD Biosciences) using 488 nm excitation laser and FL2-H channel 585 nm emission filter. In each analysis, 10,000 events were recorded after cell debris were electronically gated out. Results obtained were verified by running duplicates and repeating experiments N=3 independent experiments. Mn(III)tetrakis(4-benzoic acid)porphyrin Chloride (MnTBAP) (Sigma-Aldrich, Mo., USA) was used as a positive control.

IV. Mitochondrial Membrane Potential ($\Delta\psi_n$) Assay

Measurement of Mitochondrial Membrane Potential ($\Delta\omega_m$)(FACS). For the determination of $\Delta\psi_m$, cells were pretreated with or without the test compounds. The cells were treated with 5 mM DEM for 120 minutes, collected by centrifugation at 300×g for 3 minutes and then washed twice with phosphate buffered saline. The cells were re-suspended in PBS buffer and incubated at 37° C. in the dark for 15 minutes with 250 nM TMRM (a cationic dye which accumulates within mitochondria in accordance with the $\Delta_{\psi_m}$Nernst potential). Cells were collected by centrifugation at 300×g for 3 minutes and then washed twice with phosphate buffered saline. The samples were analyzed immediately by flow cytometry using 488 nm excitation laser and the FL2-H channel. The results obtained were verified in three independent experiments. The protonophore FCCP (30 μM) was used to dissipate the chemiosmotic proton gradient ($\Delta\mu H^+$) and served as a control for loss of $\Delta\omega_m$. In each analysis, 10,000 events were recorded.

V. Trypan Blue Cell Viability Assay

Cell viability determined by trypan blue exclusion assay: This technique was used to assess the cytoprotective effects of the invention compounds in cultured cells pharmacologically treated to induce cell death by GSH depletion. DEM was used to deplete cellular GSH and induce oxidative stress. The viability of DEM-treated cells was determined by their ability to exclude the dye trypan blue. Viable cells exclude trypan blue; whereas, non-viable cells take up the dye and stain blue. Briefly, cells were seeded at a density of $1 \times 10^6$ cells/mL and treated with different concentrations of the invention compounds. Cells were incubated at 37° C. in a humidified atmosphere of 5% $CO_2$ in air for three hours with 5 mM DEM. Cell viability was determined by staining cells with 0.4% trypan blue using a hemocytometer. At least 500 cells were counted for each experimental group. At the time of assay, >95% of DEM-treated cells were trypan blue positive; whereas, in non-DEM treated control cell cultures >95% cells were viable. Cell viability was expressed as the percentage of control. Data are expressed as means±S.E.M (n=3).

VI. Cell Viability Assays (FACS)

Cell viability and cytotoxicity were determined by simultaneous staining live and dead cells using a two-color fluorescence assay, the Live/Dead® Viability/Cytotoxicity Kit (Molecular Probes). This assay is used to measure two recognized parameters of cell viability, intracellular esterase activity and plasma integrity. The membrane-impermeant DNA dye ethidium homodimer-1 (EthD-1) was used to identify dead cells whose plasma membrane integrity was disrupted. The membrane-permeant dye calcein-AM was used to label live cells. It penetrates into the cells where it is metabolized by cytoplasmic esterases and becomes a fluorescent but membrane-impermeant probe which is retained in viable cells. Cells were incubated overnight in RPMI medium (control) and in the presence of test compound and then treated with DEM for 3 to 6 hours. Cells were stained with 0.2 μM calcein-AM and 0.4 μM EthD-1. After 15 minutes, flow cytometry analysis was carried out using excitation at 488 nm. The green-fluorescent (539 nm) FL1-H channel, live-cell population appears in the lower right quadrant and the red-fluorescent (585 nm) FL2-H channel dead-cell population appears in the upper left quadrant. In each analysis, 10,000 events were recorded. Results obtained were verified in three independent experiments.

VII. Calcein-AM Cell Viability Assay

A cell viability assay using the dye calcein acetoxymethyl (AM) was used to determine the effects of invention compounds on GSH-mediated cell death in primary FRDA patient derived fibroblasts (Jauslin et al. (2002) *Human Molecular Genetics*. 11, 3055-3063) FRDA fibroblasts were treated with L-buthionine (S,R)-sulfoximine (BSO) to inhibit de novo synthesis of GSH (Griffith et al. (1979) *J. Biol. Chem.* 254, 7558-7560) causing oxidative stress, plasma membrane damage and cell death. Fibroblasts from Friedreich Ataxia patients, but not control cells, die after GSH depletion on incubation with BSO (Jauslin et al. (2002) *Human Molecular Genetics*. 11, 3055-3063). Cell viability was determined using calcein-AM (Molecular Probe, Eugene, Oreg.). In live cells, non-fluorescent calcein AM is hydrolyzed by intracellular esterases to produce the strongly green fluorescent anion calcein.

BSO (L-buthionine (S,R)-sulfoximine) and (+)-alpha-tocopherol were purchased from Sigma Chemicals and calcein AM was purchased from Molecular Probes. Cell were grown in 75 cm² culture flasks (T75) and incubated at 37° C. in a humidified atmosphere of 5% $CO_2$ in air. Cells were fed twice a week and split every third day at a ratio of 1:3 upon reaching confluency. The invention compounds and reduced and oxidized forms of idebenone and alpha-tocopherol were reconstituted in DMSO or ethanol to provide 2.5 mM stock solutions.

The compounds were screened according to the previous protocol (Jauslin et al. (2002) *Human Molecular Genetics*. 11, 3055-3063): Fibroblasts were seeded in 96 well microtiter black-walled cell culture plates (Costar, Corning, N.Y., USA) at a density of 3000 cells per well (100 μL). The plates were incubated overnight at 37° C. in a humidified atmosphere of 5% $CO_2$ in air to allow attachment of the cells to the culture plate. Serial dilutions of intervention and references compounds were made from their respective stock solutions to give a total volume of 150 µL in each well. Plates were incubated overnight in cell culture. The following day, 50 µL of a 4 mM BSO solution (in culture media) was added to each well to provide a final BSO concentration of 1 mM. Cell viability was assessed after first signs of toxicity appeared in BSO-treated cells (typically after 24-30 hours) by examining cultures under phase-contrast microscopy. The cell culture medium was discarded by aspiration and each well of the cell culture plate washed with pre-warmed HSSB to remove serum esterase activity. Cells were then treated in with 200 µL of 1.2 µM calcein-AM in HSSB for 60 min at 37° C. in the dark to allow the dye to enter the cell and be cleaved by esterases. The negative control/background was 200 µL of HSSB buffer. Fluorescence intensities were measured with a Spectramax M5 spectrofluorometer (Molecular Devices, Sunnyvale, Calif., USA) using excitation and emission of 485 nm and 525 nm respectively. The intervention compounds were assayed in triplicate. The solvent vehicles used either DMSO or ethanol did not affect cell viability at the concentrations (0.5-1%) used in the assay. The viability of non-BSO treated fibroblasts was set as 100%, and the viability of the BSO-treated and sample-treated cells was calculated relative to this value. Cell viability was expressed as the percentage of control. Data are expressed as means±S.E.M (n=3).

VIII. Cytochrome c Reduction Assay

The rate of cytochrome c (10 µM) reduction was measured by monitoring the change in absorbance at 550 nm. Briefly the reaction was initiated by addition of 100 µM of the invention compounds to a mixture containing 50 mM phosphate buffer, 0.1 mM EDTA, pH 7.8, and 10 µM cytochrome c (Sigma, St. Louis, Mo. USA). For cytochrome c reduction by superoxide, xanthine oxidase (0.01 IU/mL) (Sigma, St. Louis, Mo. USA) was used in presence of xanthine (50 µM).

IX. Total Intercellular ATP Concentration Assay

The reductions of mitochondrial respiratory chain activity in $CoQ_{10}$ deficient patients have been reported (Quinzii G M, Lopez L C, Von-Moltke J, Naini A, Krishna S, Schuelke M, Salviati L, Navas P, DiMauro S, and Hirano, M. Respiratory chain dysfunction and oxidative stress correlate with severity of primary CoQ10 deficiency. FASEB J. 2008; 22:1874-1885). The use of $CoQ_{10}$ analogues to normalize and restore the respiratory chain activities could provide valuable therapeutic approach. We have evaluated the efficiency of oxidative phosphorylation in $CoQ_{10}$ deficient lymphocyte (GM17932) in presence of tested $CoQ_{10}$ analogues by measuring total cellular ATP content using (ViaLight® Plus ATP monitoring reagent kit, Lonza).

Briefly, lymphocytes ($2 \times 10^5$ cell/mL), were plated (1 mL in 12-well plates) and treated with the test compounds at final concentrations of 5, 10 µM, and 25 µM and incubated at 37° C. for 48 h in a humidified atmosphere containing 5% $CO_2$ in air. The test compounds were prepared by first making 20 mM stock solutions in DMSO. Cells were transferred (100 µL) to 96-well microtiter black-walled cell culture plates (Costar, Corning, N.Y.). The total intracellular ATP level was measured in a luminator (Clarity™ luminescence microplate reader) with the ATP Bioluminescence Assay Kit (ViaLight® Plus ATP monitoring reagent kit, Lonza) following the manufacturer's instructions. The standard curve of ATP was obtained by serial dilution of 1 mM ATP solution. After calibration against the ATP standard, the ATP content of the cell extract was determined and normalized for protein content in the cell. FIG. 1 shows that the cellular content of ATP are significantly lower in $CoQ_{10}$ deficient than normal lymphocyte.

X. NADH Oxidase Inhibition Assay

Beef heart mitochondria were obtained by a large-scale procedure. Inverted submitochondrial particles (SMP) were prepared by the method of Matsuno-Yagi and Hatefi (J. Biol. Chem. 260 (1985), p. 14424), and stored in a buffer containing 0.25 M sucrose and 10 mM Tris-HCl (pH 7.4) at −80° C. Inhibitory effects of compounds on bovine heart mitochondrial complex (I, III, IV) were evaluated. Maximal dimethyl sulfoxide concentration never exceeded 2% and had no influence on the control enzymatic activity. Beef heart SMP were diluted to 0.5 mg/mL. The enzymatic activities were assayed at 30° C. and monitored spectrophotometrically with a Beckman Coulter DU-530 (340 nm, $\epsilon$=6.22 $mM^{-1}$ $cm^{-1}$). NADH oxidase activity was determined in a reaction medium (2.5 mL) containing 50 mM Hepes, pH 7.5, containing 5 mM $MgCl_2$. The final mitochondrial protein concentration was 30 µg/mL. After the pre-equilibration of SMP with inhibitor for 5 min, the initial rates were calculated from the linear portion of the traces.

XI. Mitochondrial Bioenergetics Assessment

The use of $CoQ_{10}$ analogues and methylene blue analogues to normalize and restore the respiratory chain activities provides valuable therapeutic approach for mitochondrial diseases. The reductions of mitochondrial respiratory chain activity in Friedreich ataxia (FRDA) patients have been reported. The efficiency of oxidative phosphorylation was evaluated in FRDA lymphocyte (GM15850) in presence of tested $CoQ_{10}$ analogues and methylene blue analogues by measuring total cellular ATP content using (ViaLight®-Plus ATP monitoring reagent kit, Lonza).

FRDA lymphocyte cell lines were obtained from Coriell Cell Repositories. FRDA lymphocytes were cultured under glucose-free media supplemented with galactose for two weeks to force energy production predominantly through oxidative phosphorylation rather than glycolysis. Lymphocytes were cultured in RPMI 1640 medium glucose-free supplemented with 25 mM galactose, 2 mM glutamine and 1% penicillin-streptomycin, and 10%, dialyzed fetal bovine serum FBS (<0.5 µg/mL). Briefly, lymphocytes ($2 \times 10^5$ cell/mL), were plated (1 mL in 12-well plates) and treated with the test compounds at final concentrations of 50, 125. 250, 1000, and 5000 nM, and incubated at 37° C. for 48 h in a humidified atmosphere containing 5% $CO_2$ in air. Cells were transferred (100 µL) to 96-well microtiter black-walled cell culture plates. The total intracellular ATP level was measured in a luminator (Clarity™ luminescence microplate reader) with the ATP Bioluminescence Assay Kit (ViaLight®-Plus ATP monitoring reagent kit, Lonza) following the manufacturer's instructions. Carbonyl cyanide-p-trifluormethoxy-phenylhydrazone (FCCP) and oligomycin were used as control for inhibition of ATP synthesis.

Results

The compounds of the disclosure were assayed for NADH oxidase inhibition activity. The results, expressed as % activity, are shown in Table 1, below.

TABLE 1

| | NADH oxidase (complex I, III, IV) activity (%) | | |
|---|---|---|---|
| | 10 µM | 5 µM | 1 µM |
| CPD-2 | 11.9 ± 1.6 | 12 ± 0.8 | 20.1 ± 1.4 |
| CPD-3 | 70.4 ± 5.5 | 76.7 ± 6.9 | 92.9 ± 10.9 |
| CPD-5 | 33.5 ± 2.2 | 44.5 ± 3.6 | 74.5 ± 6.9 |
| CPD-4 | 10.7 ± 1.3 | 12.7 ± 1.7 | 17.1 ± 1 |
| CPD-1 | 13.2 ± 1 | 20.7 ± 2.2 | 29.7 ± 3.8 |

The compounds of the disclosure were assayed for suppression of Reactive Oxygen Species (ROS) production in cultured CEM leukemia cells pretreated with DEM. The results, shown in Table 2, are expressed as % of scavenging activity. "Untreated control" represents no DEM treatment, while the "treated control" represents DEM treatment alone.

TABLE 2

| Compounds | 10 µM | 2.5 µM | 0.25 µM |
|---|---|---|---|
| Untreated Control | 100 | 100 | 100 |
| Treated Control | 0 | 0 | 0 |
| CPD-3 | 67.0 ± 5.9 | 42.2 ± 2.9 | 4.6 ± 5.4 |
| CPD-5 | 0 ± 10 | 26.4 ± 4.4 | 21.0 ± 5.5 |
| CPD-4 | 91.0 ± 1.5 | 81.8 ± 3.7 | 41.4 ± 14.9 |
| CPD-1 | 20.0 ± 4.4 | 22.2 ± 3.5 | 23.4 ± 1.6 |
| CPD-2 | 35.2 ± 3.9 | 25.3 ± 5.2 | 31.1 ± 1.3 |

Cell viability after the treatment with the compounds of the disclosure was assayed using an FRDA cell line and a trypan blue exclusion assay (as described above). The results are expressed as % viability, and shown in Table 3. "Untreated" means control cells grown without any stress challenge; "Treated" means cells stressed with DEM, but not treated with the test compound.

TABLE 3

| Compound | 2.5 µM | 0.5 µM | 0.1 µM | Untreated | Treated |
|---|---|---|---|---|---|
| CPD-1 | 30 ± 6 | 42 ± 3 | 25 ± 6 | 93 ± 7 | 21 ± 8 |
| CPD-3 | 25 ± 5 | 19 ± 3 | 19 ± 6 | 96 ± 2 | 12 ± 3 |
| CPD-5 | 14 ± 3 | 17 ± 7 | 12 ± 6 | 96 ± 2 | 12 ± 3 |
| CPD-4 | 35 ± 9 | 21 ± 9 | 17 ± 5 | 96 ± 2 | 12 ± 3 |
| CPD-2 | 15 ± 4 | 14 ± 5 | 10 ± 3 | 96 ± 2 | 12 ± 3 |
|  | 0.1 µM | 0.5 µM | 2.5 µM | Untreated | Treated |
| CPD-6 | 27 ± 7 | 30 ± 13 | 24 ± 6 | 93 ± 7 | 21 ± 8 |
| CPD-9 | 31 ± 12 | 28 ± 7 | 32 ± 5 | 97 ± 5 | 18 ± 3 |
| CPD-12 | 15 ± 6 | 29 ± 3 | 39 ± 3 | 97 ± 5 | 18 ± 3 |
| CPD-7 | 36 ± 6 | 14 ± 5 | 20 ± 3 | 97 ± 9 | 17 ± 2 |
| CPD-10 | 19 ± 6 | 20 ± 13 | 32 ± 8 | 97 ± 9 | 17 ± 2 |
| CPD-13 | 17 ± 3 | 14 ± 2 | 19 ± 5 | 97 ± 9 | 17 ± 2 |
| CPD-8 | 19 ± 6 | 15 ± 5 | 18 ± 2 | 97 ± 9 | 17 ± 2 |
| CPD-11 | 12 ± 5 | 6 ± 3 | 8 ± 3 | 96 ± 2 | 12 ± 3 |

The compounds of the disclosure were also assayed for the lipid peroxidation suppression. The results of the suppression of lipid peroxidation in cultured leukemia CEM lymphocytes treated with diethyl maleate (DEM) is shown in Tables 4 and 5 below. Values have been calculated as (100−% mean)× 100/(% mean of the treated control). "Untreated control" represents no DEM treatment, while the "treated control" represents DEM treatment

TABLE 4

| | Scavenging activity (%) | | |
|---|---|---|---|
| Compound | 1 µM | 2.5 µM | 5 µM |
| untreated control | 100 | 100 | 100 |
| treated control | 0 | 0 | 0 |
| CPD-3 | 14 ± 4.1 | 20 ± 5.4 | 9.6 ± 2.8 |
| CPD-5 | 11 ± 1.8 | 16 ± 1.8 | 2.2 ± 2.3 |
| CPD-4 | 18 ± 2.2 | 52 ± 1.5 | 94 ± 0.2 |
| CPD-1 | 0 | 0 | 0 |
| CPD-2 | 7 ± 2.8 | 13 ± 4.2 | 0 |

TABLE 5

| | Scavenging activity (%) | |
|---|---|---|
| Compound | 1 µM | 5 µM |
| untreated control | 100 | 100 |
| treated control | 0 | 0 |
| CPD-6 | 0 | 0 |
| CPD-9 | 0 | 0 |
| CPD-12 | 0 | 0 |
| CPD-7 | 0 | 0 |
| CPD-10 | 0 | 0 |
| CPD-13 | 0 | 0 |
| CPD-8 | 10 ± 4.3 | 20 ± 3.4 |
| CPD-11 | 7 ± 2.3 | 15 ± 3.3 |

Figure 2:
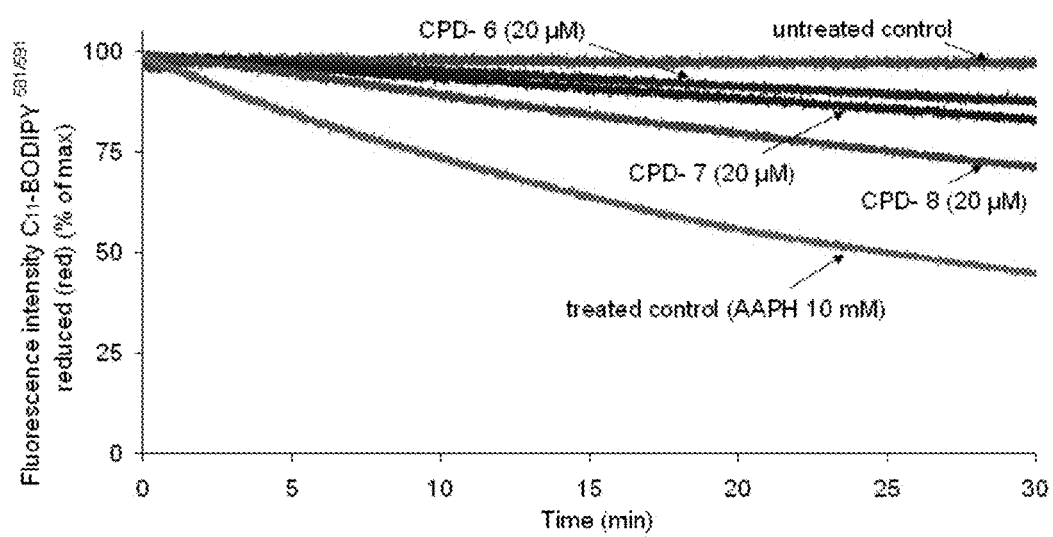
FIG. 2 shows effect of the compounds of the disclosure on lipid peroxidation induced by oxygen radicals generated from thermal decomposition of AAPH in phospholipid liposomes in phosphate buffer at 40° C. A protection against lipid peroxidation was measured by their ability to preserve the fluorescence of $C_{11}$-BODIPY$^{581/591}$ in presence of 10 mM AAPH. Relative fluorescence units are normalized to 100% intensity.

In addition, effect of the compounds of the invention on lipid peroxidation induced by oxygen radicals is illustrated in FIGS. 1 and 2. Oxygen radicals were generated from thermal decomposition of AAPH (10 mM) in phospholipids liposomes in Tris-HCl buffer containing $C_{11}$-BODIPY$^{581/591}$ (200 nM) at 40° C. The red fluorescence decay of the probe was monitored ($\lambda_{ex}$=570, $\lambda_{em}$=600 nm) over 30 minutes.

Figure 3:
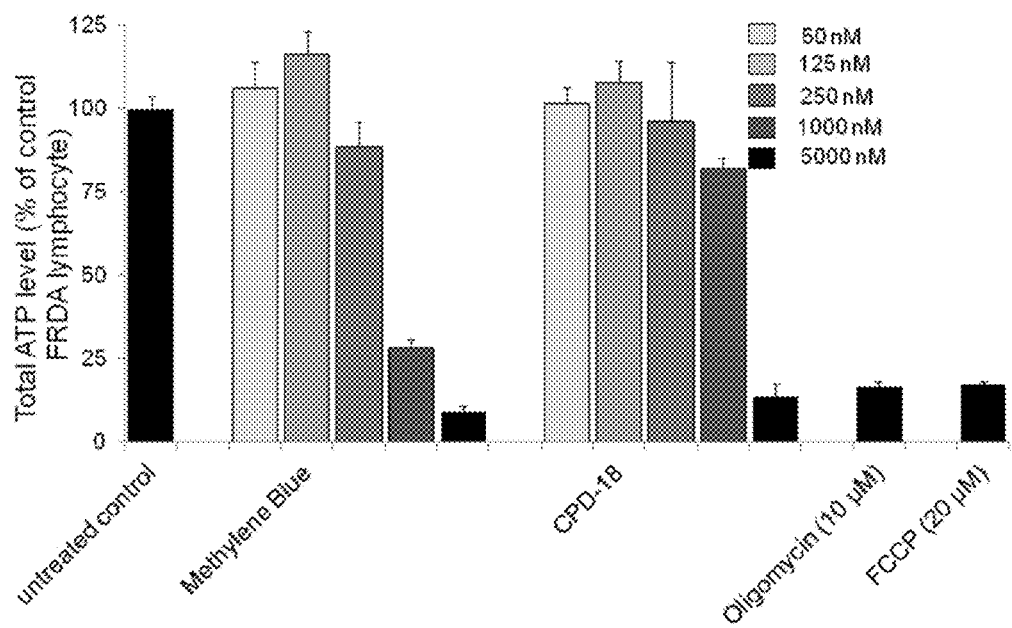
FIG. 3 shows effect of methylene blue on cellular ATP levels. Shown is representative assay of intracellular ATP level in FRDA lymphocyte cells treated with the indicated concentration of methylene blue and the compound of disclosure.

The efficiency of oxidative phosphorylation was evaluated in FRDA lymphocyte in presence of methylene blue and the compounds of the disclosure. After forty hours, methylene blue and the compound of the disclosure (CPD-18) significantly increased cellular ATP levels in FRDA lymphocyte at lower concentration (FIG. 3). CPD-18 was superior to methylene blue in maintaining ATP levels when used at higher concentrations.

It is understood that the examples and embodiments described herein are for illustrative purposes only and that various modifications or changes in light thereof will be suggested to persons skilled in the art and are to be incorporated within the spirit and purview of this application and scope of the appended claims. All publications, patents, and patent applications cited herein are hereby incorporated herein by reference for all purposes.

We claim:

1. A compound of formula:

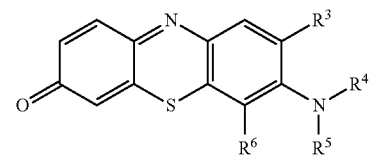

wherein
$R^3$ is hydrogen, $C_1$-$C_{20}$ alkyl, $C_2$-$C_{20}$ alkenyl, $C_2$-$C_{20}$ alkynyl, or —$OR^7$, each optionally substituted with one to four substituents selected from halogen, —CN, —$NO_2$, $C_1$-$C_6$ alkyl, halo($C_1$-$C_6$ alkyl), —$OR^8$, —$NR^8_2$, —$CO_2R^8$, —$CONR^8_2$, $C_3$-$C_8$ cycloalkyl, $C_3$-$C_8$ cycloalkenyl, aryl, heteroaryl, and heterocyclyl, wherein each cycloalkyl, cycloalkenyl, aryl, heteroaryl, and heterocyclyl are optionally substituted with $R^9$;
where each $R^7$ independently is hydrogen, $C_1$-$C_6$ alkyl, or halo($C_1$-$C_6$ alkyl);
where each $R^8$ independently is hydrogen, $C_1$-$C_6$ alkyl, halo($C_1$-$C_6$ alkyl), $C_3$-$C_8$ cycloalkyl, aryl, heteroaryl, heterocyclyl, aryl($C_1$-$C_6$ alkyl), $C_3$-$C_8$ cycloalkyl($C_1$-$C_6$ alkyl), aryl($C_1$-$C_6$ alkyl), heteroaryl($C_1$-$C_6$ alkyl), or heterocycle($C_1$-$C_6$ alkyl), wherein each cycloalkyl, aryl, heteroaryl, and heterocyclyl are optionally substituted with $R^9$;

where each $R^9$ independently is halogen, —CN, —NO$_2$, —N$_3$, C$_1$-C$_6$ alkyl, halo(C$_1$-C$_6$ alkyl), C$_1$-C$_6$ alkoxy, amino, C$_1$-C$_6$alkylamino, or diC$_1$-C$_6$alkylamino;

$R^4$ and $R^5$ are independently C$_4$-C$_{20}$ alkyl, C$_4$-C$_{20}$ alkenyl, or C$_4$-C$_{20}$ alkynyl, each optionally substituted with one to four substituents selected from halogen, —CN, —NO$_2$, C$_1$-C$_6$ alkyl, halo(C$_1$-C$_6$ alkyl), —OR$^8$, —NR$^8{}_2$, —CO$_2$R$^8$, —CONR$^8{}_2$, C$_3$-C$_8$ cycloalkyl, C$_3$-C$_8$ cycloalkenyl, aryl, heteroaryl, and heterocycle, wherein each cycloalkyl, cycloalkenyl, aryl, heteroaryl, and heterocyclyl are optionally substituted with $R^9$;

each $R^6$ is hydrogen, C$_1$-C$_{20}$ alkyl, C$_2$-C$_{20}$ alkenyl, C$_2$-C$_{20}$ alkynyl, C$_3$-C$_8$ cycloalkyl, C$_3$-C$_8$ cycloalkenyl, aryl, heteroaryl, heterocycle, or —OR$^{10}$, wherein each alkyl, alkenyl, and alkynyl are optionally substituted with one to four substituents selected from halogen, —CN, —NO$_2$, C$_1$-C$_6$ alkyl, halo(C$_1$-C$_6$ alkyl), —OR$^8$, —NR$^8{}_2$, —CO$_2$R$^8$, —CONR$^8{}_2$, C$_3$-C$_8$ cycloalkyl optionally substituted with $R^9$, C$_3$-C$_8$ cycloalkenyl optionally substituted with $R^9$, aryl optionally substituted with $R^9$, heteroaryl optionally substituted with $R^9$, and heterocyclyl optionally substituted with $R^9$;

where $R^{10}$ is C$_1$-C$_6$ alkyl, halo(C$_1$-C$_6$ alkyl), C$_3$-C$_8$ cycloalkyl, aryl, heteroaryl, heterocycle, aryl(C$_1$-C$_6$ alkyl), C$_3$-C$_8$cycloalkyl(C$_1$-C$_6$ alkyl), aryl(C$_1$-C$_6$ alkyl), heteroaryl(C$_1$-C$_6$ alkyl), or heterocycle(C$_1$-C$_6$ alkyl), wherein each cycloalkyl, aryl, heteroaryl, and heterocycles are optionally substituted with $R^9$.

2. The compound according to claim 1, wherein $R^3$ is hydrogen, optionally substituted C$_1$-C$_{20}$ alkyl, or —OR$^7$.

3. The compound according to claim 2, wherein $R^3$ is hydrogen.

4. The compound according to claim 2, wherein $R^3$ is optionally substituted C$_1$-C$_{20}$ alkyl.

5. The compound according to claim 1, wherein $R^3$ is C$_1$-C$_{20}$ alkyl optionally substituted with —OR$^8$, C$_3$-C$_8$ cycloalkyl, C$_3$-C$_8$cycloalkenyl, or aryl, wherein each cycloalkyl, cycloalkenyl, and aryl are optionally substituted with $R^9$.

6. The compound according to claim 5, wherein $R^3$ is C$_1$-C$_{20}$ alkyl optionally substituted with C$_3$-C$_8$ cycloalkyl, C$_3$-C$_8$ cycloalkenyl, or aryl, wherein each cycloalkyl, cycloalkenyl, and aryl are optionally substituted with $R^9$.

7. The compound according to claim 1, wherein $R^3$ is —OR$^7$ and $R^7$ is C$_1$-C$_6$ alkyl.

8. The compound according to claim 1, wherein $R^4$ is optionally substituted C$_4$-C$_{20}$ alkyl.

9. The compound according to claim 8, wherein $R^4$ is C$_4$-C$_{20}$ alkyl.

10. The compound according to claim 1, wherein $R^5$ is optionally substituted C$_4$-C$_{20}$ alkyl.

11. The compound according to claim 10, wherein $R^5$ is C$_4$-C$_{20}$ alkyl.

12. The compound according to claim 1, wherein $R^6$ is hydrogen or optionally substituted C$_1$-C$_{20}$ alkyl.

13. The compound according to claim 12, wherein $R^6$ is hydrogen.

14. The compound according to claim 12, wherein $R^6$ is C$_1$-C$_{20}$ alkyl optionally substituted with —OR$^8$, C$_3$-C$_8$ cycloalkyl, C$_3$-C$_8$cycloalkenyl, or aryl, wherein each cycloalkyl, cycloalkenyl, and aryl are optionally substituted with $R^9$.

15. The compound according to claim 14, wherein $R^6$ is C$_1$-C$_{20}$ alkyl optionally substituted with C$_3$-C$_8$ cycloalkyl, C$_3$-C$_8$cycloalkenyl, or aryl, wherein each cycloalkyl, cycloalkenyl, and aryl are optionally substituted with $R^9$.

16. A pharmaceutical composition comprising a compound or a pharmaceutically acceptable salt according to claim 1 and an acceptable carrier, excipient and/or diluent.

17. A method of treating or suppressing diseases associated with decreased mitochondrial function resulting in diminished ATP production and/or oxidative stress and/or lipid peroxidation, comprising administering an effective amount of a compound or a pharmaceutically acceptable salt according to claim 1, wherein the disease is selected from the group consisting of Friedreich's ataxia, Leber's Hereditary Optic Neuropathy, Kearns-Sayre Syndrome, Mitochondrial Encephalomyopathy with Lactic Acidosis and Stroke-Like Episodes, Leigh syndrome, amyotrophic lateral sclerosis, Huntington's disease, Alzheimer's disease and Parkinson's disease.

18. A method according to claim 17, wherein the disease is Friedreich's ataxia.

19. The compound of claim 1, which is:

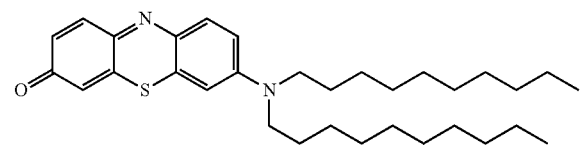 [SMILES: CCCCCCCCCCN(CCCCCCCCCC)c1ccc2nc3ccc(=O)cc-3sc2c1]

7-(didecylamino)-3H-phenothiazine-3-one; or

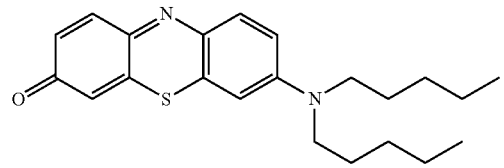 [SMILES: CCCCCN(CCCCC)c1ccc2nc3ccc(=O)cc-3sc2c1]

7-(dipentylamino)-3H-phenothiazin-3-one.

* * * * *